United States Patent
Engelhardt et al.

(10) Patent No.: US 6,992,180 B1
(45) Date of Patent: Jan. 31, 2006

(54) OLIGO- OR POLYNUCLEOTIDES COMPRISING PHOSPHATE-MOIETY LABELED NUCLEOTIDES

(75) Inventors: Dean Engelhardt, New York, NY (US); Elazar Rabbani, New York, NY (US); Stanley Kline, Brooklyn, NY (US); Janes G. Stavrianopoulos, New York, NY (US); Dollie Kirtikar, Elmhurst, NY (US)

(73) Assignee: Enzo Life Sciences, Inc. c/o Enzo Biochem, Inc., Farmingdale, NY (US)

( * ) Notice: Subject to any disclaimer, the term of this patent is extended or adjusted under 35 U.S.C. 154(b) by 0 days.

(21) Appl. No.: 08/479,997

(22) Filed: Jun. 7, 1995

Related U.S. Application Data

(60) Continuation of application No. 08/046,004, filed on Apr. 9, 1993, now abandoned, which is a continuation of application No. 07/532,461, filed on May 31, 1990, now abandoned, which is a division of application No. 07/140,980, filed on Jan. 1, 1988, now abandoned, which is a continuation of application No. 06/674,352, filed on Nov. 21, 1984, now abandoned, which is a continuation of application No. 06/391,440, filed on Jun. 23, 1982, now abandoned.

(51) Int. Cl.
*C12N 15/11* (2006.01)
(52) U.S. Cl. .................. 536/23.1; 536/25.32
(58) Field of Classification Search .............. 435/6, 435/7.1; 536/26.6, 25.31, 25.32, 23.1
See application file for complete search history.

(56) References Cited

U.S. PATENT DOCUMENTS 4,224,408 A * 9/1980 Hung et al. ............. 435/91
4,260,737 A   4/1981 Scherberg
4,358,535 A * 11/1982 Falkow et al. .......... 435/5

(Continued)

FOREIGN PATENT DOCUMENTS

DE   2507901   11/1970

(Continued)

OTHER PUBLICATIONS

Mackey et al., Biochemistry 16(20):4478-4482, 1977.*

(Continued)

*Primary Examiner*—John S. Brusca
(74) *Attorney, Agent, or Firm*—Ronald C. Fedus; Natalie Bogdanos

(57) ABSTRACT

The present invention provides a nucleotide having the formula,

Sig-PM-SM-BASE wherein PM is a phosphate moiety, SM is a sugar moiety and BASE is a pyrimidine, purine or 7-deazapurine moiety. PM is attached to the 3' or the 5' position of the sugar moiety when the nucleotide is a deoxyribonucleotide and at the 2', 3' or 5' position when the nucleotide is a ribonucleotide. BASE is attached to the 1' position of SM from the $N^1$ position when BASE is a pyrmidine or the $N^9$ position when BASE is a purine or 7-deazapurine. Sig is covalently attached to PM directly or via a chemical linkage, and represents a detectable moiety covalently attached to SM directly or through a linkage group. Also provided are an oligo- or polynucleotide comprising at least one such phosphate-moiety labeled nucleotide, and other compositions including those wherein a polypeptide is terminally ligated or attached to the oligo- or polynucleotide. The phosphate-moiety labeled nucleotide, and the oligo- or polynucleotides and other compositions comprising such phosphate-moiety labeled nucleotides, are useful as diagnostic tools for detecting analytes and as therapeutic agents.

116 Claims, 4 Drawing Sheets

U.S. PATENT DOCUMENTS

| | | | |
|---|---|---|---|
| 4,378,458 A * | 3/1983 | Gohlke et al. ............... | 536/29 |
| 4,711,955 A * | 12/1987 | Ward et al. ................. | 536/29 |
| 4,847,240 A | 7/1989 | Ryser et al. | |
| 5,212,059 A | 5/1993 | Schwartz et al. | |
| 5,242,906 A | 9/1993 | Pagano et al. | |
| 5,591,600 A | 1/1997 | Ecker, et al | |
| 5,591,720 A | 1/1997 | Anderson et al. | |
| 5,614,617 A | 3/1997 | Cook et al. | |
| 5,643,730 A | 7/1997 | Banker et al. | |
| 5,643,780 A | 7/1997 | Baker | |
| 5,652,094 A | 7/1997 | Usman et al. | |
| 5,665,710 A | 9/1997 | Rahman et al. | |
| 5,706,498 A | 1/1998 | Fujimiya et al. | |
| 5,736,294 A | 4/1998 | Ecker, et al. | |
| 5,807,677 A | 9/1998 | Eigen et al. | |
| 5,811,232 A | 9/1998 | Crooke et al. | |
| 5,874,564 A | 2/1999 | Ecker, et al. | |
| 5,891,468 A | 4/1999 | Martin et al. | |
| 5,914,230 A | 6/1999 | Liu et al. | |
| 5,953,727 A | 9/1999 | Maslyn et al. | |
| 5,966,712 A | 10/1999 | Sabatini et al. | |
| 5,980,096 A | 11/1999 | Thalhammer-Reyero | |
| 5,998,383 A | 12/1999 | Wright et al. | |
| 6,189,013 B1 | 2/2001 | Maslyn et al. | |
| 6,303,297 B1 | 10/2001 | Lincoln et al. | |
| 6,308,170 B1 | 10/2001 | Balaban | |

FOREIGN PATENT DOCUMENTS

| | | |
|---|---|---|
| EP | 0061761 A1 | 10/1982 |
| GB | 2040943 A | 9/1980 |
| JP | 5742632 | 3/1986 |
| JP | 61103824 | 5/1986 |
| WO | 8302276 | 7/1983 |

OTHER PUBLICATIONS

Sokja et al. Nucleic Acids Res, 5(2):385-401, 1978.*
Roychoundhury et al., Nucleic Acids Res, 3(1):101-116, 1976.*
Halloran et al. (J. of Immun. (1966), 96(3): 379-385).*
Lehninger, Biochemistry [Published by Worth Publishers, Inc., 70 Fifth Ave., New York, New York, USA] (1970) pp. 638-639.*
Dunn et al., Cell, vol. 12, pp. 23-36 (1977).*
Hartman et al., Biopolymers, vol. 20, pp. 2635-2648 (1981).*
Torrence et al., *J. Med. Chem.* 21:228-231 (1978).
Michelson, *Biochem. Biophys., Acta* 91:1-13 (1964)
Cech et al., *Nucleic Acids Research* 2:2183-2192 (1979).
Bleackley et al., *Nucleic Acids Research* 2:683-690 (1975).
Roberts et al, *J. Am. Chem. Soc.* 74:668-669 (1952).
Bauman et al., *Chromosoma* 84:1-18 (1982).
Bauman et al., *Exp. Cell Res.* 126:485-490 (1980).
Gerherd et al., *PNAS (USA)* 78:3755-3759 (1981).
Miller J., *Experiments in Molecular Genetics.* Cold Spring Harbor Laboratory pp. 367-370 (1972).
Ueda et al. *J. Carbohydr., Nucleosides, Nucleotides* 5:261-271(1978).
Brunngraber et al., *J. Biol. Chem.* 242:4834-4840 (1967).
Wilchek et al., *Biochemistry* 6:247-252 (1967).
Monod et al., *J. Mol. Biol.* 12:88-118 (1965).
Pastan et al., *Science* 169:339-334 (1969).
Gilbert et al., *PNAS (USA)* 70:3581-3584 (1973).
Salam et al., *Carbohydrate Research* 102:139-146 (1982)).
Pollack, S. E. and Auld, D. S., "Fluorescent Nucleotide Triphosphate Substrates for Snake Venom and Phosphodiesterase," Analytical Biochemistry 127: 81-88 (1982).
Scopes, D. I. C., et al., "Defined Dimensional Changes in Enzyme Cofactors: Fluorescent "Stretched-Out" Analogs o Adenine Nucleotides," Science 195: 296-298 (1977).
Onodera, M. and Yagi, K., "Synthesis of 2-(Dansylamino) Ethyl Triphosphate and its Properties as a Fluorescent Substrate of Heavy Meromyosin-ATPase," *Biochimica Et Biophysica* 253: 254-265 (1971).
Yarbrough, L. R., "Synthesis and Properties of a New Flourescent Analog of ATP: Adenosine-5'-Triphosphoro-γ-1-(5-Sulfonic Acid) Napthylamidate," *Biochemical and Biophysical Research Communications* 81(1): 35-41 1978).
Silver, M. S. and Fersht, A. R., "Direct Observation of Complexes Formed between recA Protein and a Fluorescent Single-Stranded Deoxyribonucleic Acid Derivative," *Biochemistry* 21: 6066-6072 (Received Apr. 16, 1982).
Crane, L. J. and Miller, D. L., "Guanosine Triphosphate and Guanosine Diphosphate as Conformation-Determining Molecules. Differential Interaction of a Fluorescent Probe with the Guanosine Nucleotide Complexes of Bacterial Elongation Factor Tu," *Biochemistry* 13(5): 933-938 (1974).
Hertz, H. S. and Zachau, H. G., "Kinetic Properties of Phenylalanyl-tRNA and Seryl-tRNA Synthetases for Normal Substrates and Flourescent Analogs," *Eur. Journal of Biochemistry* 37: 203-213 (1973).
Wu, F. Y. H. and Wu, C. W., "Flourescent Affinity Labeling of Initiation Site on Ribonucleic Acid Polymerase of *Escherichia coli,* " Biochemistry 13(12): 2562-2566 (1974).
McKenzie, R. L., et al., "Flourescent Conjugates of Natural and Biosynthetic Polynucleotides," *Biochemica Et Biophysica ACTA* 277: 306-322 (1972).
Tournon, J., "Fluorescence Probing of Nucleic Acids: I. singly and doubly labeled dithymidine phosphate: fluorescence and energy transfer studies," *Nucleic Acids Research* 2(8): 1261-1273 (1975).
Erlanger, B. F., et al., "Use of Antibodies to Nucleosides and Nucleotides in Studies of Nucleic Acids in Cells," *Methods in Enzymology* 60: 302-307 (1975).
Yarbrough, L. R., et al., "Synthesis and Properties of Flourescent Nucleotide Substrates for DNA-dependent RNA Polymerases," *The Journal of Biological Chemistry* 254 (23): 12069-12073 (1979).
Wintermeyer, W. and Zachau, H. G., "Flourescent Derivatives of Yeast tRNA$^{Phe}$," *Eur. Journal of Biochem* 98: 465-475 (1979).
Reines, S. A. and Schulman, L. H., "A New Method for Attachment of Fluorescent Probes to tRNA," Methods in Enzymology 61: 146-157 (1979).
Barrio, J. R. et al., "Synthesis of Modified Nucleoside 3', 5'-Bisphosphates and Their Incorporation into Oligoribonucleotides with T4 RNA Ligase," *Biochemistry* 17(11): 2077-2081 (1978).
Koenig, P., et al., "Pyrene Derivatives as Fluorescent Probes of Conformation Near the 3' Termini of Polyribonucleotides," *Biopolymers* 16: 2231-2242 (1977).
Menzel, H. M., "On the Phe-tRNA induced binding of fluorescent oligonucleotides to the ribosomal decoding site," Nucleic Acids Research 4(8): 2881-2892 (1977).
Leonard, N. J. and Tolman, G. L., "Fluorescent Nucleosides and Nucleotides," *Annals of the New York Academy of Sciences* 255: 43-58 (1975).
Gavrilovskaya, I. N., et al., "Immunofluorescent Demonstration of Double-Stranded RNA and Virus Antigen in RNA Virus-Infected Cells," *Virology* 62: 276-279 (1974).

Kukhavova, M. K., et al., "Peptidyl-tRNA With A Fluorescent Label: Ribosome Substrates in Peptide Bond Formation," Molecular Biology Reports 1: 397-400 (1974).

Lynch, D. C. and Schimmel, P. R., "Effects of Abnormal Base Ionizations on Mg2 + Binding to Transfer Ribonucleic Acid as Studied by Fluorescent Probe," *Biochemisgry* 13(9): 1852-1861 (1974).

Bergstrom, D. E. and Leonard N. J., "Structure of the Borohydride Reduction Product of Photolinked 4-Thiouracil and Cytosine. Fluorescent Probe of Transfer Ribonucleic Acid Tertiary Structure," Journal of the American Chemical Society 94(17): 6178-6182 (1972).

Mundry, K. W. and Priess, H., "A Quantitative Technique for Mapping Oligonucleotides on Thin Layers of Cellulose," *Biochimica Et Biophysica ACTA* 269: 225-236 (1972).

Munniger, K. O. and Chang, S. H., "A Fluorescent Nucleoside from Glutamic Acid tRNA of *Escherichia coli* K12," *Biochemical and Biophysical Research Communications* 46(5): 1837-1842 (1972).

Erlanger, B. F., et al., "Nucleic Acid-Reactive Antibodies Specific for Nucleosides and Nucleotides," Acta endocrinologic 71: 206-221 (1972).

Yoshikami, D. and Keller, E. B., "Chemical Modification of the Fluorescent Base in Phenylalanine Transfer Ribonucleic Acid," *Biochemistry* 10(15): 2969-2976 (1971).

Rudkin G. T. and Siollar, B. D., "High Resolution Detection of DNA-RNA Hybrids in situ by indirect Immunofluorescence," Nature 265: 472-473 (1977).

Rozovskaya, T. A., et al., "Introduction of a Fluorescent Label at the 3'-OH End of DNA and the 3'-OH End of the Growing RNA Chain," *Molekulyama Biologiya* 11(3): 598-610 (1977).

Kossel, H. and Seliger, H., "Recent Advances in Polynucleotide Synthesis," *Progress in the Chemistry of Organic Natural Products* 32: 297-508 (1975).

Adams, P. L. et al., *Davidson's The Biochemistry of the Nucleic Acids,* 8th Edition, Academic Press, New York, pp. 298-299 (1976).

Birch, G.G., et al., "Structural Functions and Taste in the Sugar Series; The Structural Basis of Bitterness in Sugar Analogues," *J. of Food Science* 41:1403-1407 (1976).

Chladek, S., et al., "Synthesis and Properties of Nucleoside 5'-Phosphoazidates Derived from Guanosine and Adenosine Nucleotides: Effect on Elongation Factors G and Tu Dependent Reactions," Biochemistry 16:4312-4319 (1977).

Darlix, J.L., et al., "Analysis of Transcription in Vitro Using Purine Nucleotide Analogs," Biochemistry 10:1525-1531 (1971).

Darlix, J.L., et al., "Restriction of gene transcription by nucleotide analogs," *Biochimie* 56:703-710 (1974).

Geider, K., "DNA Synthesis in Nucleotide-Permeable *Excherichia coli* Cells," *Eur. J. Biochem.* 27:554-563 (1972).

Keppler, D.O.R., et al., "Uridylate trapping, induction of UTP deficiency, and stimulation of pyrimidine synthesis de novo by D-galactosone," Biochem J. 206:139-146 (1982).

Kornberg, A., *DNA Replication,* W.H. Freeman & Company, San Francisco, Chapter 12, pp. 415-441, "Inhibtors of Replication" (1980).

Kornberg, A., *DNA Synthesis,* W.H. Freeman & Company, San Francisco, Chapter 7, pp. 227-228, "Replication" (1974).

Korytnyk, W., et al, "CMP and CMP-sugar analogs as inhibitors of sialic acid incorporation into glycoconjugates,"

Eur. J. Med. Chem. —Chimica Therapeutica 15:77-84 (1980).

Langen, P., *Antimetabolites of Nucleic Acid Metabolism,* Gordon and Breach, New York, translated from German by Dr. Thomas A. Scott, pp. 143-187 (1975).

Lartey, P.A., et al., "Preparation and Study of a Fluorescent Sugar Analog Competitive Inhibitor of Yeast Hexikinase," Preparative Biochemistry 9:85-95 (1979).

Marcus, F., "Inhibition of Fructose 1,6-Bisphosphatase by 9-B-D-Arabinofuranosyladenine 5'- Monophosphate," Cancer Research 36:1847 (1976).

Piperno, J.R., et al., "An ATP Stimulation of T4 DNA Polymerase Mediated via T4 Gene 44/62 and 45 Proteins," Journal of Biological Chemistry 253:5174-5179 (1978).

Reha-Krantz, L.J., et al., "Bacteriophage T4 DNA Polymerase Mutations That Confer Sensitivity to the PPi Analog Phosphonoacetic Acid," J. of Virology 67:60-66 (1993).

Roberts, K.R., et al., "Effects of 2-deoxy D-glucose and other sugar analogues on acid production from sugars by human dental plaque bacteria," *Scandinavian Journal of Dental Research* 88:201-209 (1980).

Scheit, K.H., *Nucleotide Analogs: Synthesis and Biological Function,* John Wiley & Sons, New York, 280 pages (1980).

Simoncsits, A., et al., "A New Type of Nucleoside 5'-Triphosphate Analogue: P1-(Nucleoside 5"-) P1-Amino-Triphosphates," Tetrahedron Letters 44:3995-3998 (1976).

Stoeckler, J.D., et al., "Human Erythrocytic Purine Nucleoside Phosphorylase: Reaction with Sugar-Modified Nucleoside Substrates," Biochemistry 19: 102-107 (1980).

Stridh, S., et al., "The Effect of Pyrophosphate Analogues on Influenza Virus RNA Polymerase and Influenza Virus Multiplication," Archive of Virology 61:245-250 (1979).

Yang, B.I-Y, et al., "Pyridoxal 5'-Phosphate and Analogs as Probes of Coenzyme-Protein Interaction," Methods of Enzymology 62:528-551 (1979).

*Organic Chemistry of Nucleic Acids, Part B.,* Kochetkov, N.K. and Budovskii, E.I., Editors, Chapter 9, pp. 449-477, Plenum Press, London & NY (1972).

Rozovskaya, T.A. et al., *Molkulyamaya Biologiya* 11(3): 598-610 (1977).

Petrov, A. I. And Sukhorukov, B.I., *Nucleic Acids Research* 8(18):4221-4234 (1980).

Hiratsuka, T. and Uchida, K., *Biochimica et Biophysica Acta* 320:635-647 (1973).

Bauman, J.G.G., *H. Histochem. Cytochem* 29:227-237 (1981).

Sodja, A. and Davidson, N., *Nucleic Acids Research* 5(2): 385-401 (1978).

Daniel F.B. and Behrman, *Biochemistry* 15(3):565-568 (1976(.

Eberhard, W. et al., *Nucleic Acids Research* 9:15-19 (1981).

Saffhill R. and Hall, J.J., *Carbohydrates Nucleosides Nucleotides* 8:573-583 (1981).

Erlanger B.F. and Beiser, S.M., *Proc. Natl. Acad. Sci.* 52:68-74 (1964).

Suzuki S. et al., *BioInorganic Chemistry* 3:281-293 (1974).

Jeng et al., *J. Supramolecular Structure* 3:448-468 (1975).

Gottikh et al., *Tetrahedron* 26:4419-4433 (1970).

*Biochemistry, Third Edition,* Stryer, L., Editor, pp. 96-97, W.H. Freeman and Co., New York (1988).

\* cited by examiner

FIG. 3A DNA BINDING TO CON A SEPHAROSE EFFECT ON MANNOSE

OLIGO- OR POLYNUCLEOTIDES COMPRISING PHOSPHATE-MOIETY LABELED NUCLEOTIDES

CROSS-REFERENCE TO OTHER RELATED APPLICATIONS

This application is a continuation of U.S. patent application Ser. No. 08/046,004, filed on Apr. 9, 1993, now abandoned, which application is a continuation of U.S. patent application Ser. No. 07/532,461, filed on May 31, 1990, also abandoned, which is a division of U.S. patent application Ser. No. 07/140,980, filed on Jan. 1, 1988, abandoned, which is a continuation of U.S. application Ser. No. 06/674,352, filed on Nov. 21, 1984, abandoned, which in turn was a continuation of U.S. application Ser. No. 06/391,440, filed on Jun. 23, 1982, abandoned. From the aforementioned Ser. No. 07/140,980, two divisional applications, U.S. patent application Ser. No. 07/532,704 (filed on Jun. 4, 1990) for "Base Moiety Labeled Detectable Nucleotide" and Ser. No. 07/567,039 (filed on Aug. 13, 1990) for "Saccharide Specific Binding System Labeled Nucleotides" issued as U.S. Pat. No. 5,241,060 (Aug. 31, 1993) and U.S. Pat. No. 5,260,433 (Nov. 9, 1993), respectively.

BACKGROUND OF THE INVENTION

It is known to produce nucleotides or polynucleotides which are radioactively labeled, such as with isotopes or hydrogen ($^3$H), phosphorus ($^{32}$P), carbon ($^{14}$C) or iodine ($^{125}$I). Such radioactively labeled compounds are useful to detect, monitor, localize and isolate nucleic acids and other molecules of scientific or clinical interest. Unfortunately, however, the use of radioactively labeled materials presents hazards due to radiation. Also due to the relatively short half life of the radioactive materials employed to label such compounds or materials, the resulting labeled compounds or materials have a corresponding relatively short shelf life.

It has been proposed to chemically label compounds of interest, such as nucleotides and polynucleotides, so as to overcome or avoid the hazards and difficulties associated with such compounds or materials when radioactively labeled. In the article by P. R. Langer, A. A. Waldrop and D. C. Ward entitled "Enzymatic Synthesis of Biotin-Labeled Polynucleotides: Novel Nucleic Acid Affinity Probes", in *Proc. Natl. Acad. Sci.*, USA, Vol. 78, No. 11, pp. 6633–6637, November, 1981, there are described analogs of dUTP and UTP that contain a biotin molecule bound to the C-5 position of the pyrimidine ring through an alkylamine linker arm. The biotin-labeled nucleotides are efficient substrates for a variety of DNA and RNA polymerases in vitro. Polynucleotides containing low levels of biotin substitution (50 molecules or fewer per kilobase) have denaturation, reassociation and hybridization characteristics similar to those of unsubstituted controls. Biotin-labeled polynucleotides, both single and double stranded, are selectively and quantitatively retained on avidin-Sepharose, even after extensive washing with 8M urea, 6M guanidine hydrochloride or 99% formamide. In addition, biotin-labeled nucleotides can be selectively immunoprecipitated in the presence of antibiotin antibody and *Staphylococcus aurea*, Protein A. These unique features of biotin-labeled polynucleotides suggest that they are useful affinity probes for the detection and isolation of specific DNA and RNA sequences. It is indicated in the article that the subject matter of the article is comprised in a pending U.S. patent application.

The disclosure of this article and above-referred pending patent application are herein incorporated and made part of this disclosure.

The patent application referred to in the above-identified article is U.S. patent application Ser. No. 255,223 filed Apr. 17, 1981. Ser. No. 06/255,223 was abandoned in favor of continuation application, U.S. patent application Ser. No. 06/496,915, filed on May 23, 1983, now U.S. Pat. No. 4,711,955. A related divisional application of the aforementioned Ser. No. 06/496,915 was filed as U.S. patent application Ser. No. 07/130,070 (on Dec. 8, 1987), and has since issued on Jul. 12, 1994 as U.S. Pat. No. 5,328,824. Two related continuation applications of the aforementioned Ser. No. 07/130,070 were filed on Feb. 26, 1992 (as Ser. No. 07/841,910) and on May 20, 1992 as (Ser. No. 07/886,660). The former, Ser. No. 07/841,910, has been allowed, and the latter, Ser. No. 07/886,660, issued as U.S. Pat. No. 5,449,767 on Sep. 12, 1995. Therefore, the disclosures of all three aforementioned U.S. Pat. Nos. 4,711,955, 5,328,824 and 5,449,767 are herein incorporated by reference and made part of the instant disclosure. The disclosures of this pending U.S. patent application Ser. No. 255,223 are herein incorporated and made part of this disclosure. In the above-identified pending U.S. patent application the subject matter of the above-identified article is disclosed and additionally it is disclosed that compounds having the structure:

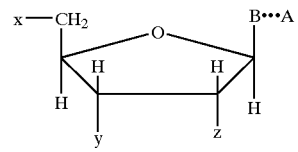

wherein B represents a purine, deazapurine, or pyrimidine moiety covalently bonded to the $C^{1'}$-position of the sugar moiety, provided that when B is purine or 7-deazapurine, it is attached at the $N^9$-position of the purine or deazapurine, and when B is pyrimidine, it is attached at the $N^1$-position;

wherein A represents a moiety consisting of at least three carbon atoms which is capable of forming a detectable complex with a polypeptide when the compound is incorporated into a double-stranded ribonucleic acid, deoxyribonucleic acid duplex, or DNA-RNA hybrid;

wherein the dotted line represents a chemical linkage joining B and A, provided that if B is purine the linkage is attached to the 8-position of the purine, if B is 7-deazapurine, the linkage is attached to the 7-position of the deazapurine, and if B is pyrimidine, the linkage is attached to the 5-position of the pyrimidine; and wherein each of x, y, and z represents

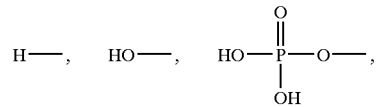

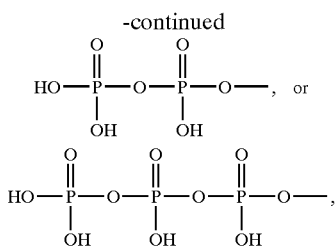

are widely useful as probes in biomedical research and recombinant DNA technology.

Particularly useful are compounds encompassed within this structure which additionally have one or more of the following characteristics: A is non-aromatic; A is at least $C_5$; the chemical linkage joining B and A includes an α-olefinic bond; A is biotin or iminobiotin; and B is a pyrimidine or 7-deazapurine.

These compounds may be prepared by a process which involves:

(a) reacting a compound having the structure:

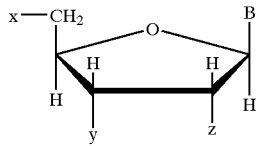

with a mercuric salt in a suitable solvent under suitable conditions so as to form a mercurated compound having the structure:

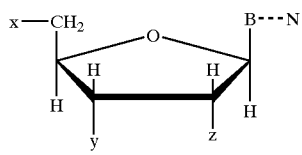

(b) reacting said mercurated compound with a chemical moiety reactive with the —$Hg^+$ portion of said mercurated compound and represented by the formula \*\*\*N, said reaction being carried out in an aqueous solvent and in the presence of $K_2PdCl_4$ under suitable conditions so as to form a compound having the structure:

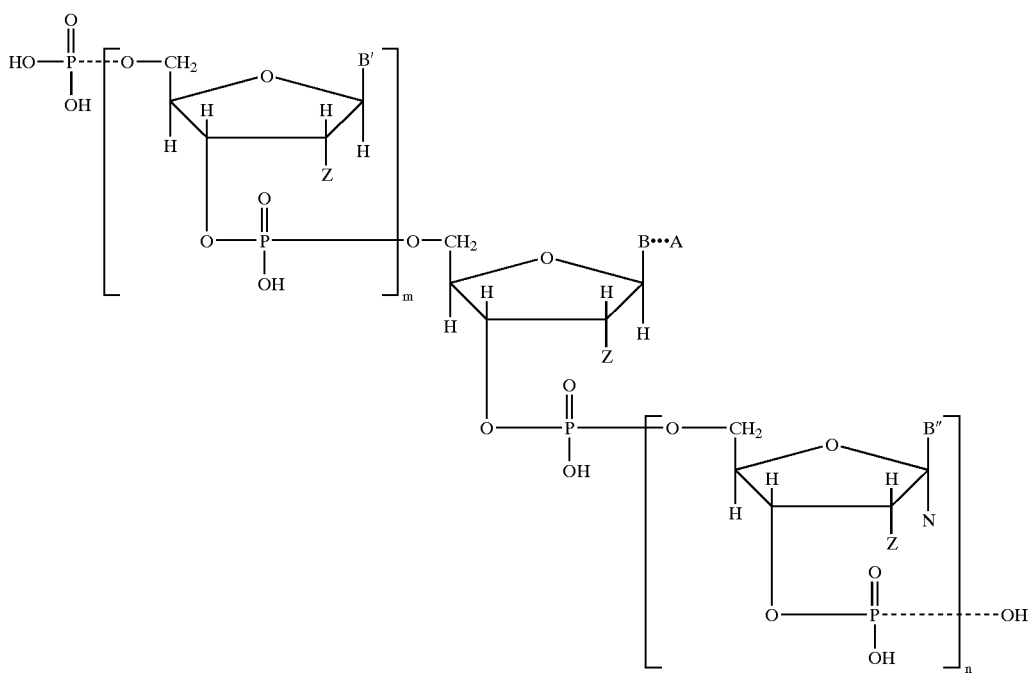

wherein N is a reactive terminal functional group or is A; and (c) recovering said compound as said modified nucleotide when N is A, or when N is a reactive terminal group, reacting said compound with a compound having the structure M-A, wherein M represents a functional group reactive with N in an aqueous solvent under suitable conditions, so as to form said modified nucleotide, which is then recovered.

This invention also provides compounds having the structure:

wherein each of B, B', and B" represents a purine, 7-deazapurine, or pyrimidine moiety covalently bonded to the $C^{1'}$-position of the sugar moiety, provided that whenever B, B', or B" is purine or 7-deazapurine, it is attached at the $N^9$-position of the purine or 7-deazapurine, and whenever B, B', or B" is pyrimidine, it is attached at the $N^1$-position;

wherein A represents a moiety consisting of at least three carbon atoms which is capable of forming a detectable complex with a polypeptide when the compound is incorporated into a double-stranded duplex formed with a complementary ribonucleic or deoxyribonucleic acid molecule.

wherein the dotted line represents a chemical linkage joining B and A, provided that if B is purine the linkage is attached to the 8-position of the purine, if B is 7-deazapurine, the linkage is attached to the 7-position of the deazapurine, and if B is pyrimidine, the linkage is attached to the 5-position of the pyrimidine;

wherein z represents H— or HO—; and wherein m and n represent integers from 0 up to about 100,000.

These compounds can be prepared by enzymatic polymerization of a mixture of nucleotides which include the modified nucleotides of this invention. Alternatively, nucleotides present in oligo- or polynucleotides may be modified using chemical methods.

Nucleotides modified in accordance with the practices of this invention and oligo- and polynucleotides into which the modified nucleotides have been incorporated may be used as probes in biomedical research, clinical diagnosis, and recombinant DNA technology. These various utilities are based upon the ability of the molecules to form stable complexes with polypeptides which in turn can be detected, either by means of properties inherent in the polypeptide or by means of detectable moieties which are attached to, or which interact with, the polypeptide.

Some uses include detecting and identifying nucleic acid-containing etiological agents, e.g. bacteria and viruses; screening bacteria for antibiotic resistance; diagnosing genetic disorders, e.g. thalassemia and sickle cell anemia; chromosomal karyotyping; and identifying tumor cells.

Several essential criteria must be satisfied in order for a modified nucleotide to be generally suitable as a substitute for a radioactively-labeled form of a naturally occurring nucleotide. First, the modified compound must contain a substituent or probe that is unique, i.e., not normally found associated with nucleotides or polynucleotides. Second, the probe must react specifically with chemical or biological reagents to provide a sensitive detection system. Third, the analogs must be relatively efficient substrates for commonly studied nucleic acid enzymes, since numerous practical applications require that the analog be enzymatically metabolized, e.g., the analogs must function as substrates for nucleic acid polymerases. For this purpose, probe moieties should not be placed on ring positions that sterically, or otherwise, interfere with the normal Watson-Crick hydrogen bonding potential of the bases. Otherwise, the substituents will yield compounds that are inactive as polymerase substrates. Substitution at ring positions that alter the normal "anti" nucleoside conformation also must be avoided since such conformational changes usually render nucleotide derivatives unacceptable as polymerase substrates. Normally, such considerations limit substitution positions to the 5-position of a pyrimidine and the 7-position of a purine or a 7-diazapurine.

Fourth, the detection system should be capable of interacting with probe substituents incorporated into both single-stranded and double-stranded polynucleotides in order to be compatible with nucleic acid hybridization methodologies. To satisfy this criterion, it is preferable that the probe moiety be attached to the purine or pyrimidine through a chemical linkage or "linker arm" so that it can readily interact with antibodies, other detector proteins, or chemical reagents.

Fifth, the physical and biochemcial properties of polynucleotides containing small numbers of probe substituents should not be significantly altered so that current procedures using radioactive hybridization probes need not be extensively modified. This criterion must be satisfied whether the probe is introduced by enzymatic or direct chemical means.

Finally, the linkage that attaches the probe moiety should withstand all experimental conditions to which normal nucleotides and polynucleotides are routinely subjected, e.g., extended hybridization times at elevated temperatures, phenol and organic solvent extraction, electrophoresis, etc.

All of these criteria are satisfied by the modified nucleotides described herein.

These modified nucleotides have the structure:

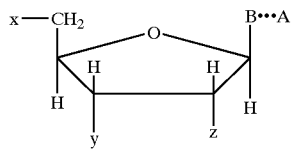

wherein B represents a purine, 7-deazapurine, or pyrimidine moiety covalently bonded to the $C^{1'}$-position of the sugar moiety, provided that when B is purine or 7-deazapurine, it is attached at the $N^9$-position of the purine or 7-deazapurine, and when B is pyrimidine, it is attached at the $N^1$-position;

wherein A represents a moiety consisting of at least three carbon atoms which is capable of forming a detectable complex with a polypeptide when the compound is incorporated into a double-stranded ribonucleic acid, deoxyribonucleic acid duplex, or DNA-RNA hybrid;

wherein the dotted line represents a linkage group joining B and A, provided that if B is purine the linkage is attached to the 8-position of the purine, if B is 7-deazapurine, the linkage is attached to the 7-position of the deazapurine, and if B is pyrimidine, the linkage is attached to the 5-position of the pyrimidine; and wherein each of x, y and z represents

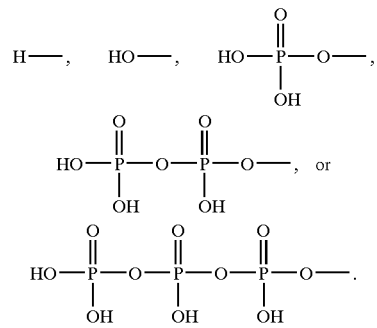

These compounds are widely useful as probes in biomedical research and recombinant DNA technology.

Although in principal all compounds encompassed within this structural formula may be prepared and used in accordance with the practices of this invention, certain of the compounds are more readily prepared or used or both, and therefore are presently preferred.

Thus, although purines, pyrimidines and 7-deazapurines are in principal useful, pyrimidines and 7-deazapurines are preferred since purine substitution at the 8-position tends to render the nucleotides ineffective as polymerase substrates. Thus, although modified purines are useful in certain respects, they are not as generally useful as pyrimidines and 7-deazapurines. Moreover, pyrimidines and 7-deazapurines useful in this invention must not be naturally substituted at the 5- or 7-positions, respectively. As a result, certain bases such as thymine, 5-methylcytosine, and 5-hydroxymethylcytosine are not useful. Presently preferred bases are cytosine, uracil, deazaadenine and deazaguanine.

A may be any moiety which has at least three carbon atoms and is capable of forming a detectable complex with a polypeptide when the modified nucleotide is incorporated into a double-stranded duplex containing either deoxyribonucleic or ribonucleic acid.

A therefore may be any ligand which possesses these properties, including haptens which are only immunogenic when attached to a suitable carrier, but are capable of interracting with appropriate antibodies to produce complexes. Examples of moieties which are useful include:

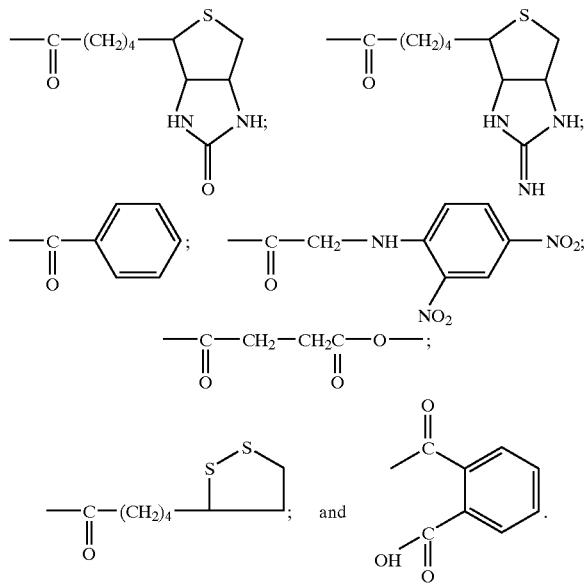

Of these the preferred A moieties are biotin and iminobiotin.

Moreover, since aromatic moieties tend to intercalate into a base-paired helical structure, it is preferred that the moiety A be nonaromatic. Also, since smaller moieties may not permit sufficient molecular interaction with polypeptides, it is preferred that A be at least $C_5$ so that sufficient interaction can occur to permit formation of stable complexes. Biotin and iminobiotin satisfy both of these criteria.

The linkage or group joining moiety A to base B may include any of the well known bonds including carbon-carbon single bonds, carbon-carbon double bonds, carbon-nitrogen single bonds, or carbon-oxygen single bonds. However, it is generally preferred that the chemical linkage include an olefinic bond at the α-position relative to B. The presence of such an α-olefinic bond serves to hold the moiety A away from the base when the base is paired with another in the well known double-helix configuration. This permits interaction with polypeptide to occur more readily, thereby facilitating complex formation. Moreover, single bonds with greater rotational freedom may not always hold the moiety sufficiently apart from the helix to permit recognition by and complex formation with polypeptide.

It is even more preferred that the chemical linkage group be derived from a primary amine, and have the structure —$CH_2$—NH—, since such linkages are easily formed utilizing any of the well known amine modification reactions. Examples of preferred linkages derived from allylamine and allyl-(3-amino-2-hydroxy-1-propyl) ether groups have the formulae —CH=CH—$CH_2$—NH— and

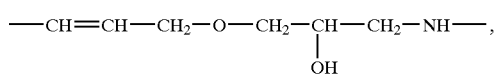

respectively.

Although these linkages are preferred, others can be used, including particularly olefin linkage arms with other modifiable functionalities such as thiol, carboxylic acid, and epoxide functionalities.

The linkage groups are attached at specific positions, namely, the 5-position of a pyrimidine, the 8-position of a purine, or the 7-position of a deazapurine. As indicated previously, substitution at the 8-position of a purine does not produce a modified nucleotide which is useful in all the methods discussed herein. It may be that the 7-position of a purine, which is occupied by a nitrogen atom, could be the point of linkage attachment. However, the chemical substitution methods employed to date and discussed herein are not suitable for this purpose.

The letters x, y, and z represent groups attached to the 5', 3', and 2' positions of the sugar moiety. They may be any of

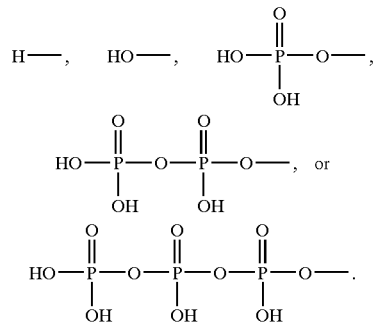

Although conceivable, it is unlikely that all of x, y, and z will simultaneously be the same. More likely at least one of x, y, and z will be a phosphate-containing group, either mono-, di-, or tri-phosphate and at least one will be HO— or H—. As will be readily appreciated, the most likely identity of z will be HO— or H— indicating ribonucleotide or deoxyribonucleotide, respectively. Examples of such nucleotides include 5'-ribonucleoside monophosphates, 5'-ribonucleoside diphosphates, 5'-ribonucleoside triphosphates, 5'-deoxyribonucleoside monophosphates, 5'-deoxyribonucleoside diphosphates, 5'-deoxyribonucleoside triphosphates, 5'p-ribonucleoside-3'p, and 5'p-deoxyribonucleoside-3'p. More specific examples include modified nucleotides of this type in which A is biotin or iminobiotin, the chemical linkage is —CH=CH—$CH_2$—NH— or

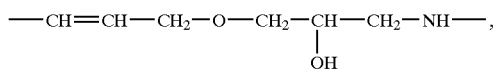

and B is uracil or cytosine.

The general synthetic approach adopted for introducing the linker arm and probe moiety onto the base is discussed hereinabove. (See especially, J. L. Ruth and D. E. Bergstrom, J. Org. Chem., 43, 2870, 1978; D. E. Bergstrom and M. K. Ogawa, J. Amer. Chem. Soc. 100, 8106, 1978; and C. F. Bigge, P. Kalaritis, J. R. Deck and M. P. Mertes, J. Amer. Chem. Soc. 102, 2033, 1980.) However, the olefin substituents employed herein have not been used previously. To facilitate attachment of probe moiety A, it has been found particularly desirable to employ olefins with primary amine functional groups, such as allylamine [AA] or allyl-(3-amino-2-hydroxy-1-propyl) ether [NAGE], which permit probe attachment by standard amine modification reactions, such as,

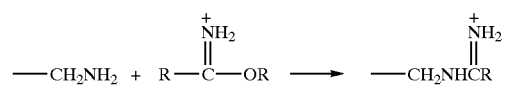

Imidate

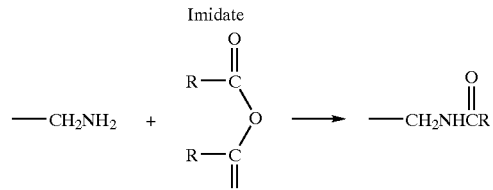

Anhydride

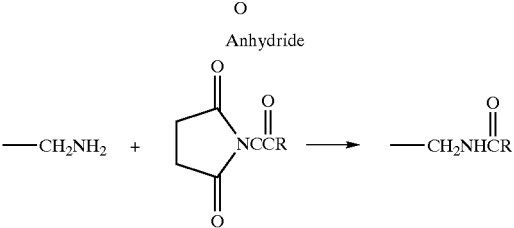

NHS-ester (N-hydroxysuccinimide)

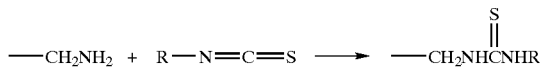

Isothiocyanate

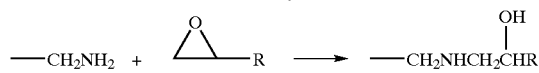

Epoxide

Because of ease of preparation it has been found preferable to use NHS-esters for probe addition. However, olefin linker arms with other modifiable functional groups, such as thiols, carboxylic acids, epoxides, and the like, can also be employed. Furthermore, both linker arm and probe can be added in a single-step if deemed desirable.

Specifically, modified nucleotides having the structure:

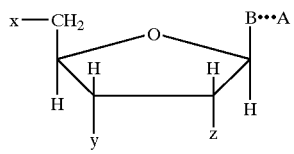

wherein B represents a purine, 7-deazapurine, or pyrimidine moiety covalently bonded to the $C^{1'}$-position of the sugar moiety, provided that when B is purine or 7-deazapurine, it is attached at the $N^9$-position of the purine or deazapurine, and when B is pyrimidine, it is attached at the $N^1$-position;

wherein A represents a moiety consisting of at least three carbon atoms which is capable of forming a detectable complex with a polypeptide when the compound is incorporated into a double-stranded ribonucleic acid, deoxyribonucleic acid duplex, DNA-RNA hybrid;

wherein the dotted line represents a chemical linkage joining B and A, provided that if B is purine, the linkage is attached to the 8-position of the purine, if 7-deazapurine, the linkage is attached to the 7-position of the deazapurine, and if B is pyrimidine, the linkage is attached to the 5-position of the pyrimidine; and wherein each of x, y, and z represents

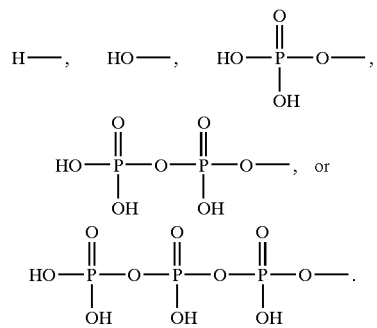

can be prepared by:

(a) reacting a compound having the structure:

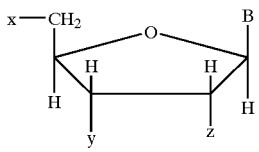

with a mercuric salt in a suitable solvent under suitable conditions so as to form a mercurated compound having the structure:

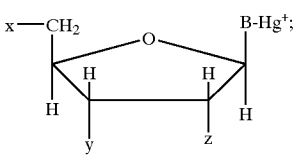

(b) reacting said mercurated compound with a chemical moiety reactive with the —Hg$^+$ portion of said mercurated compound and represented by the formula ***N, said reaction being carried out in an aqueous solvent and in the presence of $K_2PdCl_4$ under suitable conditions so as to form a compound having the structure:

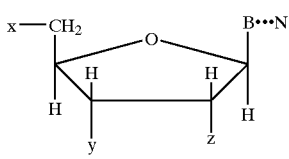

wherein N is a reactive terminal functional group or is A; and (c) recovering said compound as said modified nucleotide when N is A, or when N is a reactive terminal group, reacting said compound with a compound having the structure M-A, wherein M represents a functional group reactive with N in an aqueous solvent under suitable conditions, so as to form said modified nucleotide, which is then recovered.

The following schema is illustrative:

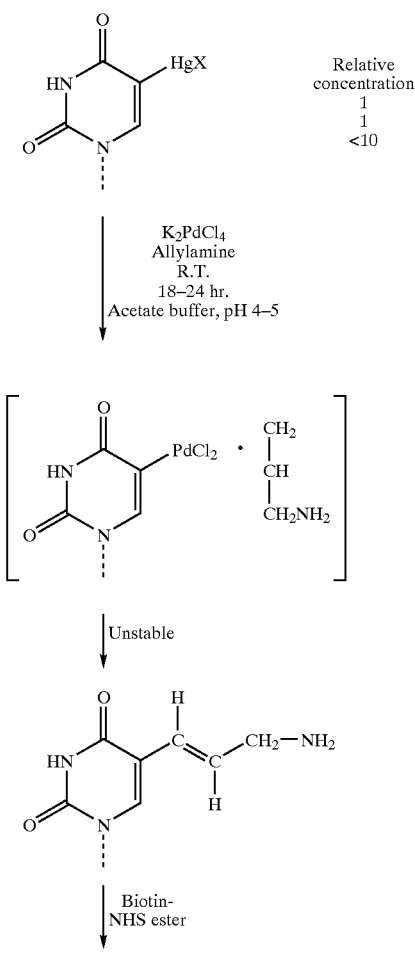

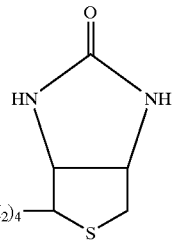

Although the reactions can be carried out at hydrogen ion concentrations as low as pH 1, or as high as pH 14, it is preferred to operate in the range from about 4 to 8. This is especially true when dealing with unstable compounds such as nucleoside polyphosphates, polynucleotides, and nucleotide coenzymes which are hydrolyzed at pH's outside this range. Similarly, it is preferred to operate at a temperature in the range from about 20° C. to 30° C. to avoid possible decomposition of labile organic substrates. However, the reactions can be carried out at temperatures from about 5° C. to 100° C. As is usual with chemical reactions, higher temperatures promote the reaction rate and lower temperatures retard it. Thus, in the temperature range from 5° C. to 100° C., the optimum reaction time may vary from about 10 minutes to 98 hours. In the preferred temperature range, reaction times normally vary from about 3 to 24 hours.

The preferred procedure for maintaining the pH in the desired range is through the use of buffers. A variety of buffers can be employed. These include, for example, sodium or potassium acetate, sodium or potassium citrate, potassium citrate-phosphate, tris-acetate and borate-sodium hydroxide buffers. The concentration of buffer, when employed, can vary over a wide range, up to about 2.0 molar.

While a particular advantage of the mercuration and palladium catalyzed addition reactions is that they can be carried out in water, small amounts of an organic solvent can be usefully included as a solubility aid. The organic solvents usually chosen are those which are miscible with water. These may be selected from ethers, alcohols, esters, ketones, amides, and the like such as methanol, ethanol, propanol, glycerin, dioxane, acetone, pyridine and dimethylformamide. However, since it has been observed that the presence of alcohols, such as methanol, often results in alkoxy-addition across the olefin double bond, any organic solvent used as a solubility aid should be chosen carefully. Introduction of alkoxy substituents to the α- or β-exocyclic carbon atoms often results in the production of compounds which are utilized much less efficiently as enzyme substrates.

Although various mercuric salts may be utilized, the presently preferred salt is mercuric acetate. Also, as indicated previously, the compounds may be prepared by first adding a linker arm and then the moiety A, or by adding a linker arm to which A is already attached. Thus, the chemical moiety represented by the formula ***N may be any one of the numerous entities which ultimately result in production of the desired compounds.

Examples include —CH=CH—CH$_2$—NH$_2$,

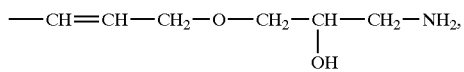

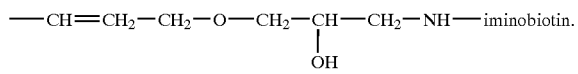

The amounts of the reactants employed in these reactions may vary widely. However, in general the amounts of unmercurated compound, mercurated compound, and palladium-containing compound will be substantially stoichiometric whereas the mercuric salt and compound *N will be present in molar excess, e.g. 5–20 moles of *N or of mercuric salt per mole of mercurated compound or unmercurated compound, respectively. In practice, amounts will vary depending upon variations in reaction conditions and the precise identity of the reactants.

Having the biotin probe directly attached to nucleotide derivatives that are capable of functioning as enzyme substrates offers considerable versatility, both in the experimental protocols that can be performed and in the detection methods (microscopic and non-microscopic) that can be utilized for analysis. For example, biotin nucleotides can be introduced into polynucleotides which are in the process of being synthesized by cells or clone cell extracts, thus making it possible to detect and/or isolate nascent (growing) polynucleotide chains. Such a procedure is impossible to do by any direct chemical modification method. Furthermore, enzymes can be used as reagents for introducing probes such as biotin into highly selective or site-specific locations in polynucleotides; the chemical synthesis of similar probe-modified products would be extremely difficult to achieve at best.

The synthesis of nucleotides containing biotin or iminobiotin was achieved as detailed in the examples set forth hereinafter. Pyrimidine nucleoside triphosphates containing either of these probes attached to the C-5 carbon atom were good to excellent substrates for a wide variety of purified nucleic acid polymerases of both prokaryotic and eukaryotic origin. These include DNA polymerase I of E. coli, bacteriophage T4 DNA polymerase, DNA polymerase α and β from murine (A-9) and human (HeLa) cells, and the DNA polymerase of Herpes simplex virus. Confirming data were obtained with E. coli DNA polymerase I using either the nick-translation condition of Rigby, et al. (P. W. J. Rigby, M. Dieckmann, C. Rhodes and P. Berg, J. Mol. Biol. 113, 237, 1977) or the gap-filling reaction described by Bourguignon et al. (G. J. Bourguignon, P. J. Tattersall and D. C. Ward, J. Virol. 20, 290, 1976). Bio-dUTP has also been found to function as a polymerase substrate both in CHO cells, permeabilized by treatment with lysolecithin according to the method of Miller, et al. (M. R. Miller, J. C. Castellot, Jr. and A. B. Pardee, Exp. Cell Res. 120, 421, 1979) and in a nuclear replication system prepared from Herpes simplex infected BHK cells. Although biotinyl ribonucleoside triphosphates were found to function as substrates for the RNA polymerases of E. coli and bacteriophage T7, they are not utilized as efficiently as their deoxyribonucleotide triphosphate counterparts. Indeed, they are incorporated poorly, if at all, by the eukaryotic RNA polymerases examined (HeLa cell RNA polymerase III, calf thymus RNA polymerase II and mouse cell RNA polymerase II). While this limited range of substrate function does restrict the utility in some in vivo or in vitro transcription studies, biotin-labeled RNA probes can be prepared enzymatically from DNA templates using E. coli or T7 RNA polymerases or by 3' end-labeling methods using RNA ligase with compounds such as biotinyl-pCp. The AA- and NAGE-derivatives of UTP are, however, substrates for the eukaryotic RNA polymerases mentioned above. With the availability of antibodies to these analogs, the isolation of nascent transcripts by immunological or affinity procedures should be feasible.

The enzymatic polymerization of nucleotides containing biotin or iminobiotin substituents was not monitored directly, since neither of these probes were radiolabeled. However, two lines of experimental evidence clearly show that the biotinyl-nucleotides were incorporated. The first is that polynucleotides synthesized in the presence of biotin-nucleotides are selectively retained when chromatographed over avidin or streptavidin affinity columns. (Tables I and II) For example, whereas normal DNA, nick translated with $^{32}$P-dAMP, is quantitatively eluted upon the addition of 0.5 M NaCl, the vast majority of biotinyl-DNA or iminobiotinyl-DNA remains bound to the resin even after extensive washing with high salt, urea, guanidine-HCl, formamide or 50 mM NaOH. The small fraction of the radiolabel eluted by these washing conditions is not retained when applied to the resin a second time, suggesting that radioactivity is associated with DNA fragments which are free of biotin substitution. The second line of evidence is that only biotin-labeled polynucleotides are immunoprecipitated when treated with purified anti-biotin IgG followed by formalin-fixed Staphylococcus aureus. (Table III) It is clear from the data in these tables that extremely small amounts of biotin can be detected by this method. These results also show that the biotin molecule can be recognized by avidin, streptavidin or specific antibodies while the DNA is still in its native, double-stranded form, a condition that is absolutely essential if the antibody-binding or avidin-affinity approaches are to be useful in probe detection employing hybridization techniques.

TABLE I

SELECTIVE RETENTION OF BIOTINIZED DNA ON AVIDIN-SEPHAROSE

| | | % DNA Retained on Resin | |
|---|---|---|---|
| Eluent | | Bio-DNA (1%) | T-DNA |
| Load - | 3 × 10$^5$ cpm 10 mM Tris 7.5 + 0.2M NaCl | 100 | 100% |
| (1) | 0.5M NaCl | 100 | 0.1 |
| (2) | 1.0M NaCl | 99.7 | <0.01 |
| (3) | 8M Urea | 100 | <0.01 |
| (4) | 6M guanidine-HCl | 95.2 | <0.01 |
| (5) | 99% formamide | 94.7 | <0.01 |
| (6) | 2 mM Biotin | 97.6 | <0.01 |
| (7) | 50 mM NaOH | 89.5 | <0.01 |

TABLE II

Affinity Chromatography of Iminobiotin-dUTP and Iminobiotinized - DNA on Streptavidin-Sepharose

| | | % Retained on SA-Sepharose | | |
|---|---|---|---|---|
| Eluent | | T-DNA | $^3$H-1B-dUTP | IB-DNA |
| Load - | 10 mM Tris-HCl, 8.3 50 mM NaCl | 8.7 | 100 | 99.7 |

TABLE II-continued

Affinity Chromatography of Iminobiotin-dUTP and Iminobiotinized-DNA on Streptavidin-Sepharose

| | | % Retained on SA-Sepharose | | |
|---|---|---|---|---|
| Eluent | | T-DNA | ³H-1B-dUTP | IB-DNA |
| (1) | 0.1M NaCl | <0.1 | 100 | 99.7 |
| (2) | 1.0M NaCl | <0.01 | 100 | 99.4 |
| (3) | 8M Urea | <0.01 | 97.5 | 98.5 |
| (4) | 6M guanidine-HCl | <0.01 | 97.0 | 97.0 |
| (5) | 50 mM NH₄-acetate, pH 4.0 | <0.01 | <0.01 | 96.5 |
| (6) | 50 mM NH₄-acetate, pH 4.0 2 mM biotin | <0.01 | <0.01 | <0.01 |

TABLE III

SELECTIVE IMMUNOPRECIPITATION OF BIO-DNA WITH ANTI-BIOTIN IgG and *STAPH AUREUS*

| DNA* | Antibody | CPM in Immuno ppt. | CPM in Supernatant |
|---|---|---|---|
| T-DNA | — | 70 | 4867 |
| T-DNA | Anti-Bio IgG | 87 | 5197 |
| T-DNA | Non-immune IgG | 55 | 5107 |
| Bio-DNA | — | 53 | 3886 |
| Bio-DNA | AnAi-Bio IgG | 3347 | 736 |
| Bio-DNA | Non-immune IgG | 60 | 3900 |

*N.T. pBR-322 DNA, ³²p-labeled; 1% Biotin substitution.
Specific activity, 2 × 10⁷ cpm/μg
Biotin detection 0.001–0.01 pmoles.

Thus, it is possible to prepare novel compounds having the structure:

wherein each of B, B', and B" represents a purine, deazapurine, or pyrimidine moiety covalently bonded to the $C^{1'}$-position of the sugar moiety, provided that whenever B, B', or B" is purine or 7-deazapurine, it is attached at the $N^9$-position of the purine or deazapurine, and whenever B, B', or B" is pyrimidine, it is attached at the $N^1$-position;

wherein A represents a moiety consisting of at least three carbon atoms which is capable of forming a detectable complex with a polypeptide when the compound is incorporated into a double-stranded duplex formed with a complementary ribonucleic or deoxyribonucleic acid molecule.

wherein the dotted line represents a linkage group joining B and A, provided that if B is purine, the linkage is attached to the 8-position of the purine, if B is 7-deazapurine, the linkage is attached to the 7-position of the deazapurine, and if B is pyrimidine, the linkage is attached to the 5-position of the pyrimidine;

wherein z represents H— or HO—; and wherein m and n represent integers from 0 up to about 100,000.

Of course, it should be readily understood that in general m and n will not simultaneously be 0 since, in that event, the compound becomes merely a modified nucleotide as described previously. In general B' and B" will vary within the same oligo- or polynucleotide, being alternatively uracil, cytosine, thymine, guanine, adenine, or the like. Also, in general, the variation will correspond to the ordered sequence of nucleotides which codes for the synthesis of peptides according to the well known Genetic Code. However, it is intended that the structure shown also embrace polynucleotides such as poly C, poly U, poly r(A-U), and poly d(A-U) as well as calf thymus DNA, ribosomal RNA of *E. coli* or yeast, bacteriophage RNA and DNA (R17, fd), animal viruses (SV40 DNA), chromosomal DNA, and the

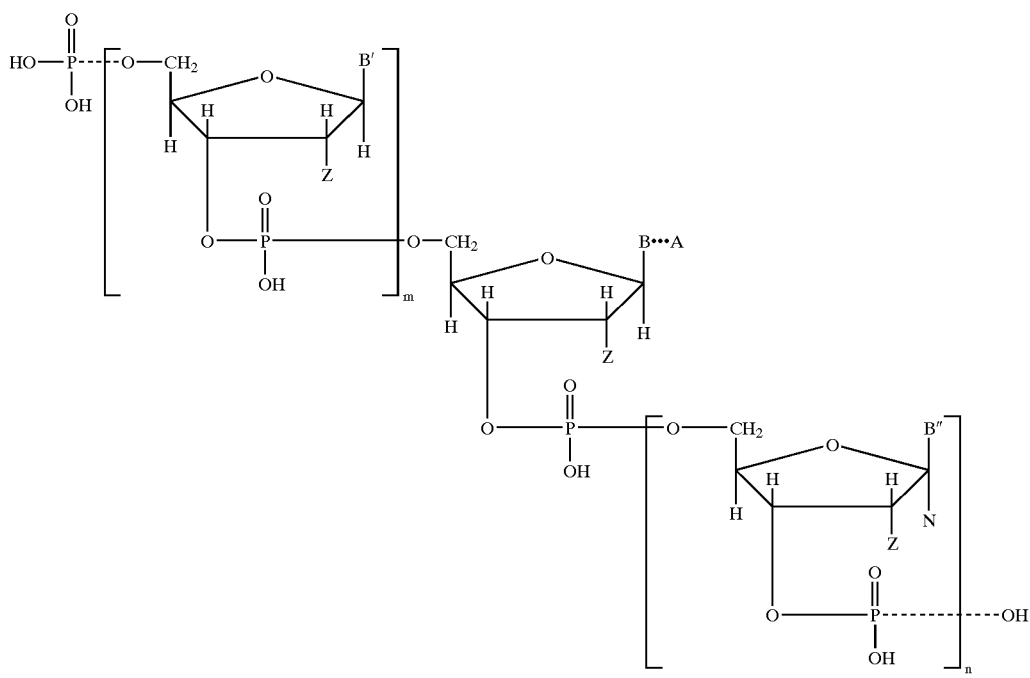

like, provided only that the polynucleotides be modified in accordance with this invention.

It is also to be understood that the structure embraces more than one modified nucleotide present in the oligomer or polymer, for example, from two to thirty modified nucleotides. The critical factor in this regard is that the number of modifications not be so great that the polynucleotide is rendered ineffective for the intended use.

Finally, it should be understood that modified oligo- and polynucleotides can be joined to form larger entities having the same structure so long as terminal groups are rendered compatible or reactive.

These compounds can be made by enzymatic polymerization of appropriate nucleotides, especially nucleotide triphosphates in the presence of a nucleic acid template which directs synthesis under suitable conditions. Such conditions can vary widely depending upon the enzyme employed, amounts of nucleotides present, and other variables. Illustrative enzymes include DNA polymerase I of E. coli, bacteriophage T4 DNA polymerase, DNA polymerases α and β from murine and human (HeLa) cells, DNA polymerase from Herpes simplex virus, RNA polymerase of E. coli, RNA polymerase of bacteriophage T7, eukaryotic RNA polymerase including HeLA cell RNA polymerase III, calf thymus RNA polymerase II, and mouse cell RNA polymerase II.

Also, the compounds can be prepared by terminal addition to oligo- or polynucleotides to produce compounds in which m or n is 0 depending upon whether the addition is at the 5' or 3' position. Moreover, the compounds such as pCp or pUp in which the base is biotinized can be added to existing molecules employing the enzyme RNA ligase.

Modified oligo- and polynucleotides can also be prepared by chemical modification of existing oligo- or polynucleotides using the approach described previously for modification of individual nucleotides.

The various modified nucleotides, oligonucleotides, and polynucleotides of this invention may be detected by contacting the compounds with polypeptides which are capable of forming complexes therewith under suitable conditions so as to form the complexes, provided that the polypeptides include one or more moieties which can be detected when the complex or complexes is or are formed, generally by means of conventional detection techniques.

One polypeptide detector for the biotinyl-type probe is avidin. The avidin-biotin interaction exhibits one of the tightest non-covalent binding constants ($K_{dis}=10^{-15}$) seen in nature. If avidin is coupled to potentially demonstrable indicator molecules, e.g., fluorescent dyes (fluorescein, rhodamine), electron-dense reagents (ferritin, hemocyanin, colloidal gold), or enzymes capable of depositing insoluble reaction products (peroxidase, alkaline phosphatase) the presence, location and/or quantity of the biotin probe can be established.

Avidin has, unfortunately, one property that makes it less desirable as a biotin-indicator protein when used in conjunction with nucleic acids or chromatin material. It has been reported (M. H. Heggeness, Stain Technol., 52, 165, 1977; M. H. Heggeness and J. F. Ash, J. Cell. Biol., 73, 783, 1977; E. A. Bayer and M. Wilchek, Methods of Biochemical Analysis 26, 1, 1980) that avidin binds tightly to condensed chromatin or to subcellular fractions that contain large amounts of nucleic acid in a manner which is independent of its biotin-binding property. Since avidin is a basic glycoprotein with a pI of 10.5, its histone-like character or its carbohydrate moieties are most likely responsible for these observed non-specific interactions.

A preferred probe for biotin-containing nucleotides and derivatives is streptavidin, an avidin-like protein synthesized by the soil organism *Streptomyces avidinii*. Its preparation and purification is described in Hoffman, et al., Proc. Natl. Acad. Sci., 77, 4666 (1980). Streptavidin has a much lower pI (5.0), is non-glycosylated, and shows much lower non-specific binding to DNA than avidin, and therefore offers potential advantages in applications involving nucleic acid detection methodology.

A most preferred protein for biotin-like probe detection is monospecific rabbit IgG, antibiotin immunoglobulin. This compound was prepared by immunizing rabbits with bovine serum albumin conjugated biotin as described previously (M. Berger, Methods in Enzymology, 62, 319 [1979]) and purified by affinity chromatography. Although the association constant of immunoglobulin-haptens have values of $K_{assn}$ ($10^6$ to $10^{10}$) which are considerably lower than for avidin-biotin complexes, they are substantially equivalent to those observed with the avidin-iminobiotin complex. Furthermore, the anti-biotin antibodies have proven extremely useful in detecting specific polynucleotide sequences on chromosomes by in situ hybridization since little, if any, non-specific binding of the antibody to chromatin material occurs.

The modified polynucleotides of this invention are capable of denaturation and renaturation under conditions compatible with their use as hybridization probes. An analysis of the thermal denaturation profiles and hybridization properties of several biotin-substituted DNA and RNA polymers clearly indicates this. For example, pBR 322 DNA or λ DNA, nick translated to introduce approximately 10–100 biotin residues per kilobase, have Tm values essentially identical to that of the control, biotin-free DNAs. Furthermore, $^{32}$P-labeled, biotin-substituted, pBR 322 DNA, exhibited the same degree of specificity and autoradiographic signal intensity as control, thymidine-containing DNA, when used as a hybridization probe for detecting bacterial colonies containing the plasmid.

In DNA duplexes, such as MVM RF DNA, in which every thymidine residue in one strand (1250 in toto per 5 Kb) is replaced by a biotinyl-nucleotide, the Tm is only 5° C. less than that of the unsubstituted control. Although the Tm of poly d(A-bioU) in which each base pair contains a bio-dUMP residue is 15° C. lower than the poly d(A-T) control, the degree of cooperativity and the extent of hyperchromicity observed both during denaturation and renaturation were the same for the two polymers. A parallel analysis of RNA duplexes and DNA/RNA hybrids indicates that their Tm's also decrease as the biotin-content of the polymer increases. However, it is clear that a substantial number of biotin-molecules can be introduced without significantly altering the hybridization characteristics of the polymers.

These results strongly suggested that biotin-substituted polynucleotides could be used as probes for detecting and/or localizing specific polynucleotide sequences in chromosomes, fixed cells, or tissue sections. The general protocol for detecting the biotin-substituted probe is schematically illustrated as follows:

GENERAL PROTOCOL FOR PROBE DETECTION VIA IN SITU, COLONY, OR NORTHERN/SOUTHERN HYBRIDIZATION METHODS

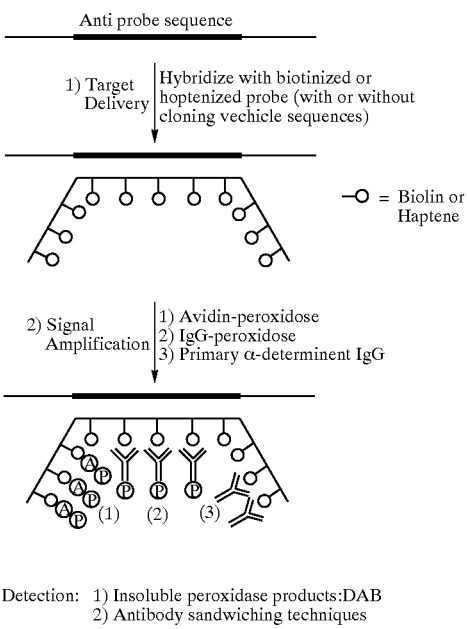

GENERAL PROTOCOL FOR PROBE DETECTION VIA IN SITU, COLONY, OR NORTHERN/SOUTHERN HYBRIDIZATION METHODS

Anti probe sequence

1) Target Delivery: Hybridize with biotinized or hoptenized probe (with or without cloning vechicle sequences)

−O = Biolin or Haptene

2) Signal Amplification:
1) Avidin-peroxidose
2) IgG-peroxidose
3) Primary α-determinent IgG 3) Detection:
1) Insoluble peroxidase products:DAB
2) Antibody sandwiching techniques This general scheme illustrates only procedures used for gene mapping (cytogenetics), and recombinant DNA-technologies. However, it can be equally well applied to the detection of nucleic acid sequences of bacterial, viral, fungal or parasite origin in clinical samples and this forms the basis of a powerful new approach to clinical diagnostics which does not rely on the use of radioisotopes.

Immunological and histochemical methods for the detection of biotin have shown that the basic approach is useable for a rapid method of gene mapping in situ hybridization and non-radioactive procedures for detecting specific nucleic acid sequences by blotting hybridization methods. Use may be made of this technology in development of new clinical diagnostic procedures.

Using this approach, it is possible to determine the presence of a specific deoxyribonucleic or ribonucleic acid molecule, particularly such a molecule derived from a living organism, e.g. bacteria, fungus, virus, yeast, or mammal. This in turn permits diagnosis of nucleic acid-containing etiological agents in a patient or other subject.

Moreover, it provides a method for screening bacteria to determine antibiotic resistance. Thus, for example, penicillin resistance in *Streptococcus pyogenes* or *Neisseris meningitidis*; tetracycline resistance in *Staphylococcus aureus, Candida albicans, Pseudomonas aeruginosa, Streptococcus pyogenes*, or *Neisseria gonorrhoeae*; and aminoglycoside resistance in *Mycobacterium tuberculosis* can be determined.

In these methods a polynucleotide is prepared which is complementary to the nucleic acid sequence which characterizes the organism or its antibiotic resistance and which additionally includes one or more modified nucleotides according to this invention. This polynucleotide is hybridized with nucleic acid obtained from the organism under scrutiny. Failure to hybridize indicates absence of the organism or of the resistance characteristic. Hybridized nucleic acid duplexes are then identified by forming a complex between the duplex and a suitable polypeptide which carries a detectable moiety, and detecting the presence of the complex using an appropriate detection technique. Positive detection indicates that the complex, the duplex and therefore the nucleic acid se-sequence of interest are present.

This approach can be extended to the diagnosis of genetic disorders, such as thalassemia and sickle cell anemia. The deoxyribonucleotide acid gene sequence whose presence or absence (in the case of thalassemia) is associated with the disorder can be detected following hybridization with a polynucleotide probe according to this invention based upon complex formation with a suitable detectable polypeptide.

The mapping of genes or their transcripts to specific loci on chromosomes has been a tedious and time-consuming occupation, involving mainly techniques of cell-fusion and somatic cell genetics. Although in situ hybridization has been employed successfully for mapping single-copy gene sequences in species that undergo chromosomes polytenization, such as *Drosophila*, detection of unique sequence genes in most higher eukaryotic chromosomes has been extremely difficult, if not impossible, using standard hybrization methods. The necessity for polynucleotide probes of very high specific radioactivity to facilitate autoradiographic localization of the hybridization site also results in rapid radiodecomposition of the probe and a concomitant increase in the background noise of silver grain deposition. The use of hybridization probes with low to moderate specific radioactivities requires exposure times of many days or weeks, even to detect multi-copy sequences, such as ribosomal RNA genes or satellite DNA. Since recombinant DNA technology has made feasible the molecular cloning of virtually every single-copy sequence found in eukaryotic cells, it would be extremely beneficial to have a rapid and sensitive method for mapping the chromosomal origin of such cloned genomic fragments.

Modified nucleotides may be used in a method of gene mapping by in situ hybridization which circumvents the use of radioisotopes. This procedure takes advantage of a thymidine analogue containing biotin that can be incorporated enzymatically into DNA probes by nick translation. After hybridization in situ the biotin molecules serve as antigens for affinity purified rabbit anti-biotin anti-bodies. Immunofluorescent antibody sandwiches made with fluorescein-labeled goat anti-rabbit IgG allow for rapid and specific cytogenetic localization of cloned gene sequences as green-yellow bands. This method offers four major advantages over conventional autoradiographic methods of in situ gene localization; less background noise, an increase in resolving power between bands; a decrease in the time required to determine the site of probe hybridization; and chemically stable hybridization probes. This method has been applied successfully to the localization of reiterated and unique DNA sequences in the polytene chromosome of *Drosophila milanogaster* and satellite DNA on mouse metaphase chromosomes.

Thus it has been found that polytene chromosomes could be used as a test system for establishing the efficacy of probes using the modified nucleotides according to the instant invention as detected by indirect immunofluorescence for in situ gene mapping. The probes included a variety of cloned *Drosophila* sequences obtained from Otto Schmidt and Dieter Söll, such as tRNA genes cloned in plasmid vectors with inserts of sizes ranging from about 5 to about 22 kilobases. Many of these clones have already been assigned to specific bands on the *Drosophila* chromosome map by conventional in situ hybridization methods employing radioisotopes.

DNA probes were nick translated in the presence of Bio-dUTP. Occasionally $^3$H dATP and/or $^3$H dCTP was included in the nick translation reaction mixture. This allowed both autoradiographic and immunofluorescent localization of a sequence on a single chromosome spread. In situ hybridization was performed as described in M. L. Pardue, and J. G. Gall, Methods in Cell Biol., 10, 1 (1975). After the final 2×SSC wash to remove unhybridized probe, the slides were rinsed with PBS (phosphate buffered saline) and incubated at 37° C. with 2.5 µg/ml Rabbit anti-biotin in PBS and 10 mg/ml BSA for 2–16 hours. This was followed by incubation of the slides with FITC labeled Goat anti-Rabbit IgG (Miles Laboratories, diluted 1:100 in PBS and 10 mg/ml BSA) for one–four hours. Evans Blue was often required as a red counterstain to see the chromosomes with fluorescent illumination.

When plasmids pBR 17D and pPW 539 containing 5 Kb and 22 Kb inserts, respectively, were hybridized by this method, it was found that the pattern of hybridization is reproducible from spread to spread and is observed unambiguously on greater than 90% of the chromosome spreads on a given slide.

The cloned transposable element pAC 104 is known to map at many sites along the *Drosophila* genome. Comparison of the autoradiograph and the fluorescent picture obtained by in situ hybridization of this probe illustrates a major advantage of this method, i.e., that where diffuse regions of silver grains appear on an autoradiograph, doublets or a series of bands are discernible by immunofluorescent labeling.

The other immediately obvious advantage of this method is the tremendous decrease in time required for gene assignments to be made by indirect immunofluorescence. An assignment of a DNA fragment to a specific band can be made within six hours of hybridization. This is in comparison to days or weeks required for autoradiographic exposure methods. This factor, in combination with increased resolution, makes the use of modified nucleotides detected by indirect immunofluorescence immediately preferable to more classical methods.

It has been shown that this immunological method also works with mammalian chromosomes wherein satellite DNA has been mapped to the centromeric regions of mouse metaphase chromosomes. The result provides a basic foundation for the development of a simple gene mapping procedure for single copy (unique) sequences in chromosomes from human and other mammals. Such a procedure should greatly facilitate our understanding of the genetic organization of the chromosome and make clinical cytogenetic diagnosis much more rapid and practical.

While a single-step "antibody sandwich" method in which the chromosome spread is challenged, post-hybridization, with rabbit anti-biotin IgG may succeed, this protocol may not generate sufficient fluorescence for unambiguous gene assignments. However, a much stronger fluorometric signal can be achieved by using the "haptene-antibody sandwich technique" described by Lamm, et al., (1972); Wofsy, et al., (1974). In this procedure the primary antibody, in our case monospecific, rabbit anti-biotin IgG, is chemically modified with a haptenization reagent, such as 2,4-dinitrofluorobenzene, preferably while the immunoglobulin is bound to an antigen affinity column (biotin-Sepharose™). As many as 15–20 haptene (DNP) groups can be coupled to the primary antibody without decreasing its antigen binding affinity or specificity (Wallace and Wofsy, 1979). If the primary antibody treatment of the test sample is followed by an incubation with a fluorescently labeled anti-hapten IgG antibody, rather than a fluorescently labeled anti-IgG, a 5–7 fold increase in fluorescence signal can be achieved. Since one also has available monospecific guinea pig anti-DNP IgG, we can haptenize this secondary antibody with biotin and thus generate two anti-hapten IgG populations, DNP-labeled anti-biotin IgG and biotin-labeled anti-DNP IgG. If these can be used alternately to achieve several rounds of hapten-antibody sandwiching and then followed with fluorescently labeled protein A from *Staphylococcus aureus*, which binds specifically to IgG molecules from many mammalian species, it could result in an enormous amplification of the primary antibody signal with its concomitant utility.

The protein streptavidin from *Streptomyces avidini* is a potential alternative to anti-biotin IgG as a vehicle to specifically direct a coupled visualization system [e.g., fluorescent probes (above) or histochemical reagents (below)] to the site of the hybridized biotin-containing polynucleotide. One of streptavidin's advantages over anti-biotin IgG is that its affinity for biotin is $K_{assn}=10^{15}$ whereas association constants for haptene-IgG interactions are $10^7$ to $10^{10}$. The fast reaction rate and extreme affinity mean that the time required to localize the biotinized probe will be minutes with streptavidin versus hours with immunologic reagents.

Initial evaluations of a streptavidin detection system are currently in progress. Polytene chromosomes hybridized with biotinized DNA probes will be incubated with streptavidin followed by a subsequent incubation with bovine serum albumin which has been doubly labeled with biotin and FITC (FITC, biotinyl-BSA). Since only one of the four streptavidin subunits is likely to be involved in binding at each biotinized DNA site, potentially one labeled BSA molecule can bind to each of the remaining three nonconjugated subunits of the streptavidin-biotinyl nucleotide complex. The fluorescence signal from this single streptavidin+FITC, biotinyl-BSA layer will be compared with a control using the basic "antibody sandwich method" described earlier.

If the "antibody sandwich" and streptavidin+FITC, biotinyl-BSA detection intensities are comparable, one can attempt to enhance the streptavidin+FITC, biotinyl-BSA system to single-copy copy sensitivity in a manner that parallels the multiple "haptene-antibody sandwich" approach. Since some of biotin groups on BSA will not be bound to the first layer of streptavidin, a second layer of streptavidin can be added until sufficient signal is obtained. For example, if in the second layer, only two streptavidin protomers bind to each first-layer BSA and each of these streptavidin protomers binds three FITC-biotinyl BSA molecules, then the second layer intensity will be twice as great as that from the first layer; for the third layer, with analogous binding stoichiometries, the fluorescent intensity will be 12-fold that of the first layer, so the total intensity will rapidly increase with successively added layers. There are plans to use a larger carrier protein such as thyroglobulin rather than BSA in order to maximize amounts of attached fluorescent and biotin probes. It may also be necessary to use a longer linker arm between the biotin probe and the carrier protein. A longer linker arm should sterically optimize the theoretical delivery of a biotinized fluorescent carrier molecule to each nonconjugated streptavidin subunit and maximize the number of streptavidin promoters in the subsequent layer which will bind to the biotinized fluorescent carrier. As before, appropriate controls will be done to insure that substitution of the carrier protein with fluorescent probes and biotin does not cause solubility and/or nonspecific binding problems.

The streptavidin-carrier protein delivery system has two significant advantages over the immunofluorescent approach in addition to its speed of delivery. First, only two protein components are needed to form the layers. Second, only the carrier protein needs to be modified and it is not necessary to maintain functional or even total structural integrity as long as the biotin groups are accessible to streptavidin.

An alternative to the fluorescence method for visualizing hybridized probes is to direct enzymes such as peroxidase, alkaline phosphatase of β-galactosidase to the hybridization site where enzymatic conversion of soluble substrates to insoluble colored precipitates permits light microscope visualization. The important advantage of this technique is that the histochemical methods are 10 to 100-fold more sensitive than fluorescence detection. In addition, the colored precipitates do not bleach with extensive light exposure thus avoiding one of the general disadvantages of fluorescent light microscopy. These enzymes can be coupled to the final antibody instead of fluorescent probes in the "haptene-antibody sandwich" technique using bifunctional reagents such as glutaraldehyde or in the case of peroxidase via oxidation of the peroxidase carbohydrate moieties to aldehydes and coupling of these residues with ε-amino groups of the desired protein. For the streptavidin-biotinized carrier protein method, an enzyme with biotinyl groups coupled to it could replace a fluorescently-biotinized carrier system. Alternately, the enzyme could be coupled via biotin to the last layer of streptavidin with amplification of streptavidin sites being built up in preceding layers using biotinized BSA or thyroglobulin. We will begin developing the necessary histochemical reagents and the appropriate substrate/insoluble product combinations for visualizing in situ hybridizations without background problems in the near future. The histochemical approaches to signal amplification should therefore be ready for trial in the summer of 1981.

Detecting and/or imaging very low levels of fluorescent light is possible using currently available image intensifiers or systems composed of lasers and photomultipliers. These methods permit the detection of light down to the level of individual photons. With suitable digital processing systems, images can be produced in which each point, i.e. each pixel, of the image is strictly proportional to the number of photons emitted by a point at the object. Using systems of this kind of flow systems in which the cells or parts of cells flow past a laser beam, one can obtain detection sensitivity increases for fluorescent material of factors between 100 and 1000 beyond that which can be detected by the eye. This increase is sufficient to detect the fluorescence of single copy genes.

In a preferred modification, analogs of dUTP and UTP that contain a biotin molecule covalently bound to the C-5 position of the pyrimidine ring through an allylamine linker arm have been synthesized. These biotinyl-nucleotides are efficient substrates for a variety of DNA and RNA polymerases in vitro. DNA containing low levels of biotin substitution (50 molecules or less/kilobase) has denaturation, reassociation and hybridization characteristics which are indistinguishable from that of unsubstituted control DNA.

Thus, this invention also provides a method of chromosomal karyotyping. In this method, modified polynucleotides are prepared which correspond to known genes and include modified nucleotides. These polynucleotides are hybridized with chromosomal deoxyribonucleic acid and the resulting duplexes contacted with appropriate polypeptides under suitable conditions to permit complex formation. The polypeptides include detectable moieties so that the location of the complexes can be determined and the location of specific genes thereby fixed.

Another embodiment of this invention involves detection of poly A-containing sequences using poly U in which some of the uracil bases have been modified to contain a probe. Yet another embodiment involves cyclic modified nucleotides in which two of x, y, and z are reacted to form the cyclic moiety

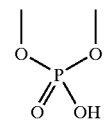

Such cyclic modified nucleotides may then be used to identify hormone receptor sites on cell surfaces which in turn can be used as a method of detecting cancer or tumor cells.

Finally, tumor cells can be diagnosed by preparing polynucleotides which are modified according to this invention and are complementary to the messenger ribonucleic acid synthesized from a deoxyribonucleic acid gene sequence associated with the production of polypeptides, such as α-fetal protein or carcinoembryonic antigen, the presence of which is diagnostic for specific tumor cells. Hybridization and detection of hybrid duplexes thus would provide a method for detecting the tumor cells.

The examples which follow are set forth to illustrate various aspects of the present invention but are not intended to limit in any way its scope as more particularly set forth in the claims.

EXAMPLES 1 AND 2

Synthesis of Biotinyl-UTP and Biotinyl-dUTP a) Preparation of Mercurated Nucleotides UTP (570 mg, 1.0 mmole) or dUTP 554 mg, 1.0 mmole) was dissolved in 100 ml of 0.1 M sodium acetate buffer pH 6.0, and mercuric acetate (1.59 gm, 5.0 mmoles) added. The solution was heated at 50° C. for 4 hours, then cooled on ice. Lithium chloride (392 mg, 9.0 mmoles) was added and the solution extracted six times with an equal volume of ethyl acetate to remove excess $HgCl_2$. The efficiency of the extraction process was monitored by estimating the mercuric ion concentration in the organic layer using 4,4'-bis (dimethylamino)-thiobenzophenone (A. N. Christoper, Analyst, 94, 392 (1969). The extent of nucleotide mercuration, determined spectrophotometrically following iodination of an aliquot of the aqueous solution as described by Dale et al. (R. M. K. Dale, D. C. Ward, D. C. Livingston, and E. Martin, Nucleic Acid Res. 2, 915 [1975]), was routinely between 90 and 100%. The nucleotide products in the aqueous layer, which often became cloudy during the ethyl acetate extraction, were precipitated by the addition of three volumes of ice-cold ethanol and collected by centrifugation. The precipitate was washed twice with cold absolute ethanol, once with ethyl ether, and then air dried. These thus prepared mercurated nucleotides were used for the synthesis of the allylamine-nucleotides without further purification.

b) Synthesis of Allylamine-dUTP and Allylamine-UTP

The mercurated nucleotides (of step a) were dissolved in 0.1 M sodium acetate buffer at pH 5.0, and adjusted to a concentration of 20 mM (200 OD/ml at 267 nm). A fresh 2.0 M solution of allylamine acetate in aqueous acetic acid was prepared by slowly adding 1.5 ml of allylamine (13.3 mmoles) to 8.5 ml of ice-cold 4 M acetic acid. Three ml (6.0 mmoles) of the neutralized allylamine stock was added to 25 ml (0.5 mmole) of nucleotide solution. One nucleotide equivalent of $K_2PdCl_4$, (163 mg, 0.5 mmole), dissolved in 4 ml of water, was then added to initiate the reaction. Upon addition of the palladium salt (Alfa-Ventron) the solution gradually turned black with metal (Hg and Pd) deposits appearing on the walls of the reaction vessel. After standing at room temperature for 18–24 hours, the reaction mixture was passed through a 0.45 mm membrane filter (nalgene) to remove most of the remaining metal precipitate. The yellow filtrate was diluted five-fold and applied to a 100 ml column of DEAE-Sephadex™ A-25 (Pharmacia). After washing with one column volume of 0.1 M sodium acetate buffer at pH 5.0, the products were eluted using a one liter linear gradient (0.1–0.6 M) of either sodium acetate at pH ~8–9, or triethylammonium bicarbonate (TEAB) at pH 7.5. The desired product was in the major UV-absorbing portion which eluted between 0.30 and 0.35 M salt. Spectral analysis showed that this peak contained several products, final purification was achieved by reverse phase—HPLC chromatography on columns of Partisil—ODS2, using either 0.5 M $NH_4H_2PO_4$ buffer at pH 3.3 (analytical separations), or 0.5 M triethylammonium acetate at pH 4.3 (preparative separations) as eluents. The 5'-triphosphates of 5-(3-aminopropen-1-yl) uridine (the allylamine adduct to uridine) were the last portions to be eluted from the HPLC column and they were clearly resolved from three, as yet uncharacterized, contaminants. These nucleotides were characterized by proton NMR elemental analysis [AA-dUTP ($C_{12} H_{16} N_3 O_{14} P_3 Na_4$.1 $H_2O$): theory C, 22.91; H, 2.88; N, 6.68; P, 14.77. Found, C, 23.10; H, 2.85; N, 6.49; P, 14.75. AA-UTP ($C_{12} H_{16} N_3 O_{15} P_3 Na_4$.4$H_2O$): Theory, C 20.61; H, 3.46; N, 6.01; P, 13.3. Found C, 20.67; H, 4.11; N, 5.39; P, 13.54] spectrally and chromatographically.

c) Biotination of AA-dUTP or AA-UTP

Biotinyl-N-hydroxysuccinimide ester (NHSB) was prepared from biotin (Sigma) as described previously (H. Heitzmann and F. M. Richards, Proc. Natl. Acad. Sci. USA. 71, 3537 [1974]). AA-dUTP.$H_2O$ (63 mg, 0.1 mmole) or AA-UTP.4$H_2O$ (70 mg, 0.1 mmole) was dissolved in 20 ml of 0.1 M sodium borate buffer at pH 8.5, and NHSB (34.1 mg, 0.1 mmole) dissolved in 2 ml of dimethyl formamide, was added. The reaction mixture was left at room temperature for four hours and then loaded directly onto a 30 ml column of DEAE-Sephadex™ A-25, preequilibrated with 0.1 M TEAB at pH 7.5. The column was eluted with a 400 ml linear gradient (0.1–0.9 M) of TEAB. Fractions containing biotinyl-dUTP or biotinyl-UTP, which eluted between 0.55 and 0.65 M TEAB, were desalted by rotary evaporation in the presense of methanol and redissolved in water. Occasionally a slightly cloudy solution was obtained: this turbidity, due to a contaminant in some TEAB solutions, was removed by filtration through a 0.45 mm filter. For long term storage, the nucleotides were converted to the sodium salt by briefly stirring the solution in the presence of Dowex™ 50 ($Na^+$ form). After filtration the nucleotide was precipitated by the addition of three volumes of cold ethanol, washed with ethyl ether, dried in vacuo over sodium hydroxide pellets, and stored in a dessicator at −20° C. For immediate use, the nucleotide solution was made 20 mM in Tris-HCl at pH 7.5, and adjusted to a final nucleotide concentration of 5 mM. Stock solutions were stored frozen at −20° C.

Elemental analysis of the bio-dUTP and bio-UTP products yielded the following results. Bio-dUTP ($C_{22} H_{30} N_5 O_{18} P_3 S_1 Na_4$.1 $H_2O$). Theoretical; C, 29.80; H, 3.38; N, 7.89; P, 10.47; S, 3.61. Found; C, 30.14 H, 3.22; N, 7.63; P, 10.31; S, 3.70. Bio-UTP ($C_{22} H_{30} N_5 O_{19} P_3 S_1 Na_4$.3 $H_2O$): Theoretical; C, 29.15; H, 3.19; N, 7.45; P, 9.89; S, 3.41. Found; C, 28.76; H, 3.35; N, 7.68; P, 9.81; S, 3.32.

The spectral properties of bio-dUTP and bio-UTP at pH 7.5 [λ max, 289 nm ($\epsilon$=7,100); λ max, 240 nm ($\epsilon$=10,700); λ min, 262 nm ($\epsilon$=4,300)] reflect the presence of an exocylic double-bond in conjugation with the pyrimidine ring. These nucleotides also give a strong positive reaction (an orange-red color) when treated with p-dimethylaminocinnamaldehyde in ethanolic sulfuric acid, a procedure used for biotin quantitation (D. B. McCormick and J. A. Roth, Anal. Biochem., 34, 326, 1970). However, they no longer react with ninhydrin, a characteristic reaction of the AA-dUTP and AA-UTP starting materials.

EXAMPLES 3 AND 4

Synthesis of Biotinyl-CTP and Biotinyl-dCTP

CTP and dCTP were a) mercurated, b) reacted with allylamine, and c) biotinized with NHS-biotin, essentially as described in Example 1. CTP (56.3 mg, 0.1 mmole) or dCTP (59.1 mg, 0.1 mmol) were dissolved in 20 ml of 0.1 M sodium acetate buffer at pH 5.0, and mercuric acetate (0.159 gm, 0.5 mmoles) added. The solution was heated at 50° C. for 4.5 hours then cooled on ice. Lithium chloride (39.2 mg, 0.9 mmoles) was added and the solution extracted 6 times with ethyl acetate. The nucleotide products in the aqueous layer were precipitated by the addition of three volumes of cold ethanol and the precipitate collected by centrifugation. The precipitate was washed with absolute ethanol, ethyl ether, and then air dried. These products were used without further purification for the synthesis of AA-CTP and AA-dCTP, respectively. The mercurated nucleotides were dissolved in 0.1 M sodium acetate buffer at pH 5.0 and adjusted to a concentration of 10 mM (92 OD/ml at 275 nm). 0.6 ml (1.2 mmole) of a 2.0 M allylamine acetate stock (prepared as described in Example 1) was added to 10 ml of nucleotide solution (0.1 mmole) followed by the addition of $K_2PdCl_4$ (32.6 mg, 0.1 mmole), dissolved in 1.0 ml of $H_2O$. After standing at room temperature for 24 hours, the solution was filtered through a 0.45 mM membrane to remove metal precipitates. The filtrate was diluted five-fold and loaded onto a 50 ml column of DEAE-sephadex A-25, preequilibrated with 50 mM TEAB at pH 7.5. The nucleotide products were fractionated by application of a 500 ml linear gradient (0.05–0.6 M) of TEAB at pH 7.5. The desired product was in the major UV absorbing portion which eluted between 0.28 and 0.38 M salt. The pooled samples were desalted by rotary evaporation, dissolved in 0.5 M triethylammonium acetate at pH 4.2, and final purification achieved by HPLC chromatography on columns of Partisil ODS-2, using 0.5 M triethylammonium acetate as the eluent. Appropriate fractions were pooled, lyophilized, and the products dissolved in $H_2O$. The nucleotides were converted to the $Na^+$ salt by stirring briefly in the presence of Dowex™ 50 ($Na^+$ form). After filtration, to remove the Dowex resin, the nucleotides were precipitated by the addition of 3 volumes of cold ethanol. The precipitate was washed with ether and then air dried. Analytical results: AA-dCTP ($C_{12}$ $H_{17} N_4 O_{13} P_3 Na_4 \cdot 2H_2O$); Theory, C, 22.29; H, 2.63; N, 8.67, P, 14.40. Found C, 22.16; H, 2.89; N, 8.77; P, 14.18. AA-CTP ($C_{12} H_{17} N_4 O_{14} Na_4 \cdot 2H_2O$); Theory C, 21.75; H, 2.57; N, 8.46; P, 14.01. Found, C, 22.03; H, 2.47; N, 8.69; P, 13.81; Spectral properties in 0.1 M Borate buffer at pH 8.0, $\lambda$ max 301 nm ($\epsilon$=6,400), $\lambda$ min 271 nm ($\epsilon$=3,950) $\lambda$ max 250 nm ($\epsilon$=9,700). Both AA-dCTP and AA-CTP give a positive ninhydrin test.

AA-CTP (6.6 mg, 0.01 mmole) or AA-dCTP (6.4 mg, 0.01 mmole) was dissolved in 5 ml of 0.1 M sodium borate buffer at pH 8.5, and NHS-biotin (3.4 mg, 0.01 mmole), dissolved in 0.2 ml of dimethylformamide, was added. After sitting at room temperature for 4 hours the sample was chromatographed on a 10 ml column of DEAE-Sephadex A-25, using a 150 ml linear gradient (0.1–0.9 M) of TEAB at pH 7.5, as eluent. Fractions containing biotinyl-CTP or biotinyl-dCTP, which eluted between 0.50 and 0.60 M TEAB, were pooled, desalted by rotary evaporation, and after being adjusted to a final concentration of 5 mM in 0.02 M Tris-HCl buffer at pH 7.5, were frozen at −20° C. The products give a strong positive reaction for biotin with p-dimethylaminocinnamldehyde in ethanolic sulfuric acid but give a negative test for primary amines when sprayed with ninhydrin. Further structural characterization of these products is in progress.

EXAMPLES 5 AND 6

Synthesis of Iminobiotinyl-UTP and Iminobiotinyl-dUTP

Iminobiotin hydrobromide was prepared from biotin as described previously (K. Hofmann, D. B. Melville and V. du Vigneaud, J. Biol. Chem., 141, 207–211, 1941; K. Hofmann and A. E. Axelrod, Ibid., 187, 29–33, 1950). The N-hydroxysuccinimide (NHS) ester of iminobiotin was prepared using the protocol previously described for the synthesis of NHS-Biotin (H. Heitzmann and F. M. Richards, Proc. Nat. Acad. Sci. USA, 71, 5537, 1974). AA-UTP (7.0 mg, 0.01 mmole) or AA-dUTP (6.3 mg, 0.01 mmole), prepared as detailed in example 1 (part b), was dissolved in 5 ml of 0.1 M sodium borate buffer at pH 8.5, and NHS-iminobiotin (3.5 mg, 0.01 mmole), dissolved in 0.5 ml of dimethylformamide, was added. The reaction mixture was left at room temperature for 12 hours and then loaded directly onto a 10 ml column of DEAE-Sephadex A-25, preequilibrated with 0.05 M TEAB at pH 7.5. The column was eluted with a 150 ml linear gradient (0.05–0.6 M) of TEAB. Fractions containing iminobiotin-UTP or iminobiotin-dUTP, which eluted between 0.35 and 0.40 M TEAB, were desalted by rotary evaporation in the presence of methanol and dissolved in $H_2O$. The products contained a small amount of allylamine-nucleotide adduct as an impurity, as judged by a weak positive result in the ninhydrin test. Final purification was achieved by affinity chromatography on avidin-sepharose. Fractions of the impure product, made 0.1 M in soldium borate buffer at pH 8.5, were applied to a 5 ml column of avidin-sepharose and washed with 25 ml of the same buffer. The column was then washed with 50 mM ammonium acetate buffer at pH 4.0, which eluted the desired iminobiotin-nucleotide product in a sharp peak. The nucleotide was precipitated by the addition of 3 volumes of cold ethanol, washed with ethylether, dried in vacuo over sodium hydroxide pellets and stored in a dessicator at −20° C. Products were characterized by elemental analysis, as well as by spectral and chromatographic properties.

EXAMPLES 7 AND 8

Synthesis of NAGE-UTP and NAGE-dUTP

Allyl (3-amino-2-hydroxy-)propyl ether, abbreviated NAGE, was prepared from allyl glycidyl ether (Age) (obtained from Aldrich Chemical Co.). 10 ml of Age (84 mmole) was added slowly (in a fume hood) to 50 ml of 9 M ammonium hydroxide and the mixture allowed to stand at room temperature for six hours. Excess ammonia was removed by rotary evaporation under reduced pressure to yield a viscous yellow oil. Analysis of this product by proton NMR showed that it possessed the required structure. 5-mercuri-dUTP (0.1 mmole) or 5-mercuri-UTP (0.2 mmole) was dissolved in 2–4 ml of 0.2 M sodium acetate buffer at pH 5.0, and a 16 fold molar excess of NAGE adjusted to pH 5.0 with acetic acid prior to use, was added. The final reaction volumes (4.3 and 8.4 ml) had nucleotide concentrations of 43 and 42 mM, respectively. One equivalent of $K_2PdCl_4$ (0.1 or 0.2 mmoles) was added to initiate the reaction. After standing at room temperature for 18 hours, the reaction mixtures were filtered through 0.45; $\mu$mM membranes the samples diluted five-fold, and chromatographed on columns of DEAE-Sephadex A-25, using linear gradients (0.1–0.6 M) of sodium acetate. Fractions containing the desired products, as judged by their UV spectra and characteristic HPLC elution profiles on Partisil ODS-2, were pooled, diluted, and further purified by rechromatography on DEAE-Sephadex using shallow gradients (0.1–0.5 M) of ammonium bicarbonate at pH 8.5. Under these conditions the majority of the NAGE-dUTP (or NAGE-UTP) could be cleanly separated from residual impurities. Proton NMR spectra were obtained at this stage of purification after the nucleotides were lyophilized and redissolved in $D_2O$. For elemental analysis, the products were converted to their sodium salt form. Typical analytical results: Nage-dUTP ($C_{15} H_{22} N_3 O_{16} P_3 Na_4 \cdot 2 H_2O$), Theory, C, 24.99; H, 3.63; N, 5.83; P, 12.88. Found, C, 25.39; H, 3.71; N, 5.63; P, 12.88

EXAMPLE 9

Uses of Labeled DNA Sequences

I. Karyotyping (a) Select from a human gene library some 100 to 200 clones. Label them as described above, and for each clone locate its place or places of hybridization visually or with a low-light-level video system. For those clones which correspond to a unique sequence gene this determines the location of the cloned DNA on a particular human chromosome. Obtain several clones for each chromosome. Each of these labeled clones can be used to identify particular chromosomes. They can also be used in combination to identify each of the 46 chromosomes as being one of the 22 autosomal pairs of the X or the Y. By allowing one set of labeled clones to hybridize to the chromosomes and then adding a fluorescent stain to the label, the set of clones and their locations can be visualized and will flouresce with a particular color. A second set of labeled clones could then be used and reacted with a second fluorescent dye. The same process can be repeated a number of times. Thus one can, if desired, have several sets of fluorescent labels attached to the cellular DNA at different but specific locations on each of the chromosomes. These labels could be used for visual or computerized automatic karyotyping.

(b) For automatic karyotyping, one could use one set of clones to identify the approximate location of each of the 46 chromosomes by finding sets of spots corresponding to the number of labeling sites on each chromosome. Thus, it is possible by computer analysis of the digitized images to determine if the chromosomes are suitably spread for further analysis. If they are suitably spread then one can use computer analysis to identify each of the individual chromosomes by the location and distribution of the labelled spots on each one.

By using the fact that the fluorescent spots can be placed at specific locations on each chromosome, one can carry out either manual or automatic karyotyping very much more effectively than without such labels.

II. Diagnosis of Genetic Disorders

By selecting the clones which bind specifically to a particular chromosome, such as number 23, it is possible to count the number of copies of the particular chromosome in a cell even if the chromosomes are not condensed at metaphase. Thus when fetal cells are obtained for prenatal diagnosis of trisomy 21, the diagnosis can be done even if the chromosomes are not condensed at metaphase. If necessary, two sets of labels can be used—one which would be specific for chromosome 23 and one for some other chromosome. By measuring in each cell the ratio of the two labels, which might be of different colors, it is possible to identify the cells which show an abnormal number of chromosomes number 23. This procedure could be used either on slides with a low-light-level video system or in a flow cytometer system using laser excitation. It can be used to determine any abnormal chromosome number.

III. Microorganism Detection and Identification

The labeling of specific sequences of DNA as described above permits identification and counting of individual bacteria. In order to identify the individual bacteria to which a particular fragment of DNA hybridizes the sensitivity must be such that a single labelled structure can be detected. This can be done using a low-light-level video system and computer summation of images, or by using some other device for intensifying the light image. A flow system can also be used if the sensitivity can be made sufficiently grand. If one immobilized the bacteria on a slide their location could be found and the number of such fluorescent spots counted. This would provide a count of all of those bacteria which contain DNA which can hybridize whith the specific clone utilized. If the clone is selected as being specific for a particular strain or bacteria, then one can count the number of organisms of that strain. In addition, any antibiotic resistance for which a particular gene has been identified could be characterized in a similar way using, as a probe, the DNA sequence which is contained in the antibiotic resistance gene. In addition, a probe could be used which is specific for a resistance plasmid containing one or more antibiotic resistance genes. In addition to individual bacteria, groups of bacterial cells of a particular strain can be detected and their number estimated if they are located in a small spot so that the total fluorescence specific to the hybridized DNA in the spot can be measured. In this way the number of organisms containing a specific DNA sequence can be measured in a mixture of bacteria.

By way of additional background with respect to the utilization of the biotin-polynucleotides of the above-identified Langer et al article in *Proc. Natl. Acad. Sci. USA*, the publication by P. R. Langer-Safer, M. Levine and D. C. Ward in *Genetics* entitled "An Immunlogical Method for Mapping Genes on *Drosophila* Polytene Chromosomes", describes a method employing biotinated nucleotides as a probe for the localization of DNA sequences hybridized in situ to *Droso-phila* polytene chromosomes. In this application these probes are detected using affinity purified rabbit antibiotin antibody as the primary antibody and fluorescenated goat antirabbit antibody as the secondary antibody. The disclosures of this Langer-Safer et al publication in *Genetics* are also incorporated and made part of this disclosure.

Other techniques employing biotin-labeled reagents with avidin or enzyme-labeled avidin reagents are known for the detection and determination of ligands in a liquid medium, see U.S. Pat. No. 4,228,237. Also, it is known to effect gene enrichment based on avidin-biotin interaction, particularly as applied to *Drosophila* ribosomal RNA genes, see the J. Manning, M. Pellegrini and N. Davidson publication in *Biochemistry*, Vol. 16, No. 7, pages 1364–1369 (1977). Other publications of background interest with respect to the practices of this invention are the D. J. Eckermann and R. H. Symons article entitled "Sequence at the Site of Attachment of an Affinity-Label Derivative of Puromycin on 23-S Ribosomal RNA of *Escherichia coli* Ribosomes", *J. Biochem*, 82, 225–234 (1978); the article by S. B. Zimmerman, S. R. Kornberg and A. Kornberg entitled "Glucosylation of Deoxyribonucleic Acid-II -Glucosyl Transferases" from T2- and T6-Infected *Escherichia coli* in *The Journal of Biological Chemistry*, Vol. 237, No. 2, February 1962, and the article by J. Josse and A. Kornberg "III. α- and β-Glucosyl Transferases from T4-Infected *Escherichia coli*", also appearing in *The Journal of Biological Chemistry*, Vol. 237, No. 6, June 1962.

Of further interest in connection with the practices of this invention are the publications appearing in the *J. Biol. Chem.*, Vol. 236, No. 5, May 1961, pages 1487–1493; the same publication; Vol. 237, No. 4, pages 1251–1259 (1962); the same publication Vol. 239, No. 9, pages 2957–2963 (1964). Of special interest is the article appearing *The Journal of Histochemistry and Cytochemistry*, Vol. 27, No. 8, pages 1131–1139 (1979) and in the publication *Nucleic Acids Research*, Vol. 5, No. 9, 1977, pages 2961–2973. Also of interest is the article appearing in the publication *Biochimica et Biophysica Acta* by A. De Waard entitled "Specificity Difference Between the Hydroxymethylcytosine β-Glucosyl-Transferases Induced by Bacteriophages T2, T4 and T6", pages 286–304, and also the article by T. W. North and C. K. Mathews entitled "T4 Phage-Coded Deoxycytidylate Hydroxymethylase: Purification and Studies in Intermolecular Interactions", published by Academic Press, 1977, pages 898–904 and the article by E. A. Bayer and M. Wilchek entitled "The Use of Avidin-Biotin Complex as a Tool in Molecular Biology in *Methods of Biochemical Analysis*," Vol. 26, pages 1–45 (1980).

Other techniques useful in the practices of this invention include nick translation of DNA employing DNA polymerase. A technique for effecting nick translation is disclosed in the article by P. W. Rigby, M. Dieckmann, C. Rhodes and P. Berg entitled "Labeling Deoxyribonucleic Acid to High Specific Activity in vitro by Nick Translation with DNA Polymerase" in *J. Mol. Biol.* (1977), 113, 237–251. With respect to the recovery of streptavidin, such as from a culture broth of *Streptomyces avidinii*, the article by K. Hofmann, S. W. Wood, C. C. Brinton, J. A. Montibeller and F. M. Finn entitled "Iminobiotin Affinity Columns and their Application to Retrieval of Streptavidin" in *Proc. Natl. Acad. Sci. USA*, Vol. 77, No. 8, pp. 4666–4668 (1980), discloses a suitable approach for the recovery of streptavidin from a strepavidin-containing material, such as from a culture broth. Streptavidin is useful as a reagent in one of the practices of this invention.

The publications cited in the aforementioned U.S. Pat. Nos. 4,711,955, 5,328,824 and 5,449,767 are also herein incorporated and made part of this disclosure.

SUMMARY OF THE INVENTION

In accordance with the practices of this invention nucleotides are modified, such as at the 5 position of pyrimidine or the 7 position of purine, preparatory for the preparation therefrom of nucleotide probes suitable for attachment to or incorporation into DNA or other nucleic acid material. In the practices of this invention nucleotides, i.e. nucleic acids, preferably are modified in a non-disruptive manner such that the resulting modified nucleotides are capable of incorporation into nucleic acids and once incorporated in nucleic acids the modified nucleotides do not significantly interfere with the formation or stabilization of the double helix formed of the resulting nucleic acids containing the modified nucleotides. The non-disruptive modification of nucleotides and nucleic acids incorporating such modified nucleotides is in contrast with those modifications of nucleotides which are characterized as a disruptive modification in the sense that the resulting disruptively modified nucleotides and nucleic acids containing the same block proper double helix formation. In the practices of this invention, the nucleotides are desirably modified at the 5 position of the pyrimidine or the 7 position of the purine. The nucleotides so modified are non-disruptively modified and nucleic acids containing such nucleotides are capable of forming a double helix arrangement.

Broadly, in another aspect of the practices of this invention various methods are useful for the tagging or labeling of DNA in a non-disruptive manner. For example, biotin is added on the end of a DNA or RNA molecule. The addition of biotin is accomplished by addition of a ribonucleotide. The 3',2' vicinal hydroxyl groups are oxidized by periodate oxidation and then reduced by a borohydride in the presence of biotin hydrazide. Alternatively, carbodiimide can also be used to couple biotin to the aldehyde group.

Another technique for tagging nucleic acid material such as DNA or RNA involves the addition of a large marker to the end of a DNA or RNA molecule. One example of this technique is the addition of a molecule, e.g. lysyl-glycine, where the amino groups are tagged with biotin. Another example would be to follow the procedure set forth hereinabove but employing carbodiimide as the cross-linking agent. Still another example of this technique would be to produce a biotinylated dA:dU double helical polymer and to ligate this polymer to the probe prepared in accordance with this invention.

Another technique for tagging DNA in a non-disruptive manner involves the isolation of dPyrTP having a putricine or spermidine on the 5 position from PS16 or phage-infected cells. If desired, dPyrTP is made from phage DNA and phosphorylated to dPyrTP followed by modification of the polyamine side chain by means of standard nucleophilic reagent NHS-biotin.

Another technique for tagging DNA in a non-disruptive manner involves the addition of glucose to 5-hydroxymethylcytosine (5 HMC) in DNA using T4 phage glycoslyating enzymes followed by screening by means of a lectin-based assay.

Still another method for tagging DNA in a non-disruptive manner involves 5-HMC-triphosphate made from the hydrolysis of T4-DNA followed by phosphorylation of the 5 HMCMP to 5 HMCTP. 5 HMCTP is then incorporated into DNA using polymerase I. Thus, any DNA can be modified to have non-disruptively incorporated therein 5 HMC.

A method for tagging DNA in a mildly disruptive manner involves reacting nucleic acids in the double helical form with alkylating reagents as for example benz(o)pyrene diol epoxide or aflatoxin. Under appropriate conditions the $N^2$ group of guanine, the $N^6$ group of adenine or the $N^4$ group of cytosine are alkylated. These modified nucleotides can be directly detected with antibodies or can be used as linking arms for the addition of a reporter molecule such as biotin.

BRIEF DESCRIPTION OF THE DRAWINGS

FIG. 3A is a graph that illustrates the recovery (measured as a percent) of tritium labeled T4 DNA using a Con A-sepharose column when mannose is included in the buffer, as described in Example XXII.

Figure 1:
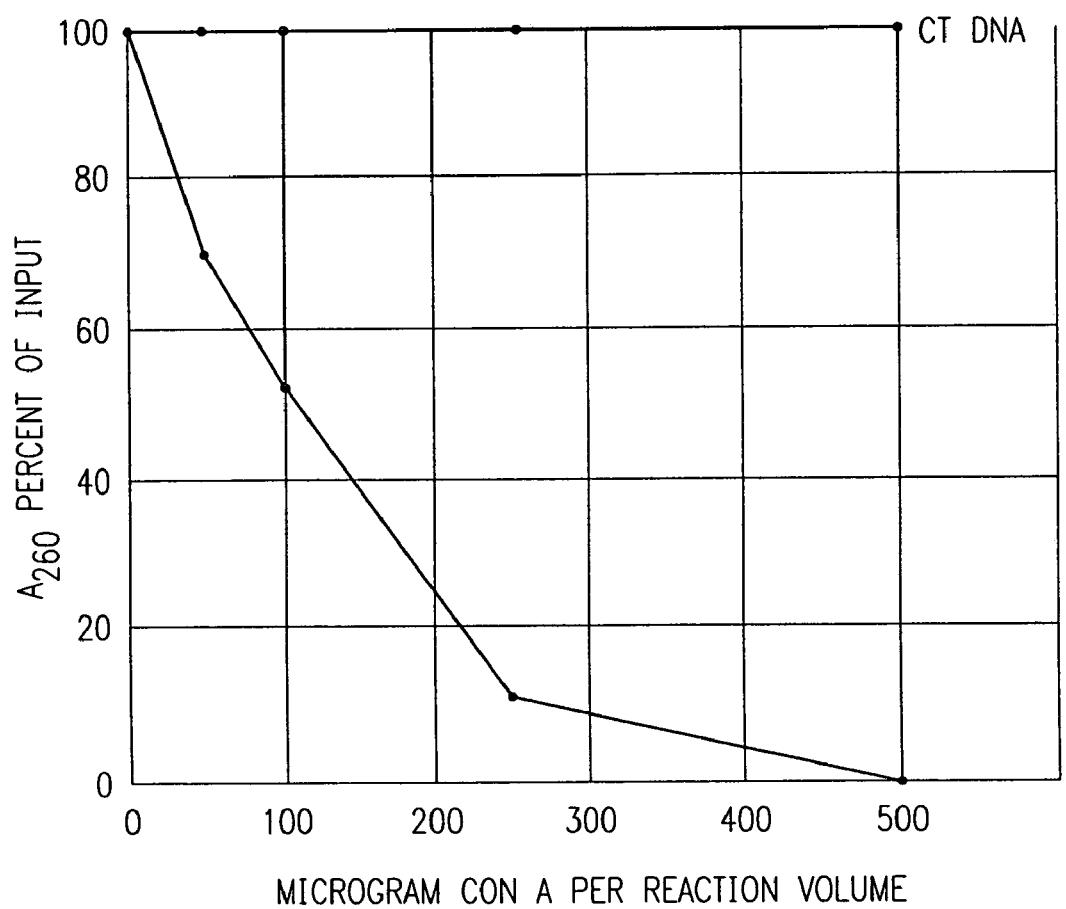
FIG. 1 is a graph that shows the results of a precipitation reaction of glucosylated DNA as described in Example XXI. Absorbance was measured at 260 nanometers for the reaction mixtures and control solutions.

The following examples are illustrative of various embodiments of the practices of this invention:

EXAMPLE I

Biotinyl-N-hydroxysuccinide ester (BNHS) was prepared according to a method of Becker et al, P.N.A.S. 68 2604 (1971). Biotin (0.24 g, 1.0 mmol) was dissolved in 5 ml dry dimethylformamide. Dicyclohexylcarbodiimide (0.21 g, 1.0 mmol) and N-hydroxysuccinimide (0.12 g, 1.0 mmol) were added and the solution stirred at room temperature for 15 hours. After filtration of the subsequent precipitate, the filtrate was evaporated at reduced pressure. The residue was washed twice with ethanol and recovered from hot isopropyl alcohol to yield a white crystalline product having a m.p. of 216–218° C.

EXAMPLE II

Biotinyl-1,6-diaminohexane amide was prepared as follows: A solution of 1,6-diaminohexane (320 mg, 2.0 mmol), dissolved in 50 ml water, was brought to pH 8.5 by addition of carbon dioxide. Biotinyl-N-hydroxysuccinimide ester (100 mg, 0.29 mmol), dissolved in 10 ml dimethylformamide, was added. After 18 hours at room temperature the mixture was evaporated and the residue washed with ether and subsequently dried in a dessicator.

EXAMPLE III

Polybiotinylaed poly-L-lysine was prepared by the following procedure. Polylysine (100 umol lysine) dissolved in 2 ml 0.1 M sodium borate, pH 8.5 was added to biotinyl-N-hydroxysuccimide ester (17.5 mg, 50 umol) dissolved in 0.5 ml dimethylformamide. After stirring at room temperature for 18 hours, the mixture was dialyzed against 10 mM tris buffer, pH 7.5.

EXAMPLE IV

Oligodeoxyribonucleotides were end-labeled using cytidine-5'-triphosphate and terminal transferase as follows. Purified phage DNA, alkali sheared with 0.2 N sodium hydroxide and diluted to 2 $A_{260}$ units/ml in potassium cacodylate (0.1 M), tris base (25 mm), cobalt chloride (1 mM) and dithiothreitol (0.2 M) were used. To this DNA solution (1 ml) was added cytidine-5'-triphosphate (10 mmol) and terminal transferase (200 units).

After incubating at 37° for 5 to 8 hours the reaction was stopped by the addition of neutralized phenol (100 ul), 0.5 M EDTA (100 ul) and 1% sodium dodecyl sulfate (100 ul). The DNA was purified by gel filtration chromatography through Sephadex G-100 followed by precipitation with ethanol.

EXAMPLE V

Biotin and polybiotinylated poly-L-lysine were coupled to oligoribonucleotides using a carbodiimide coupling procedure described by Halloran and Parker, *J. Immunol.*, 96 373 (1966). As an example, DNA (1 ug/ml), 1 ml) in tris buffer pH 8.2, sheared with 0.1 N sodium hydroxide was denatured by boiling for 10 minutes and quick cooling in an ice bath. Biotinyl-1,6-diaminohexane amide (2 mg, 6 umol) or polybiotinylated poly-L-lysine (2 mg) and 1-ethyl-3-diisopropylaminocarboimide HCl (10 mg, 64 umol) were added, and the pH readjusted to 8.2. After 24 hours at room temperature in the dark, the mixture was dialyzed against 10 mM tris buffered saline. DNA was precipitated ethanol.

EXAMPLE VI

Biotin, conjugated to cytochrome C, was prepared by the following procedure. To a solution of cytochrome C (10 mg) in 1 ml of 0.1 M sodium borate, pH 8.5 was added biotinyl-N-hydroxysuccinimide ester (10 mg, 29 umol) in 1 ml dimethyl formamide. After 4 hours at room temperature, the biotinylated protein was purified by gel filtration chromatography through a Sephadex G-50 column.

EXAMPLE VII

Formaldehyde coupling of cytochrome C-biotin and polybiotinylated poly-L-lysine to oligodeoxyribonucleotides were carried out using a method similar to that described by Manning et al, *Chromosoma*, 53, 107 (1975). Oligodeoxyribonucleotide fragments obtained by sodium hydroxide shearing of purified DNA (100 ug/ml in 10 mM triethanolamine, pH 7.8 were denatured by boiling for 10 minutes followed by quick cooling in ice. Cytochrome C-biotin 0.05 g ml or polybiotinylated poly-L-lysine solution (0.05 ml) dissolved 3 mg/ml in 10 mM triethanolamine, pH 7.8 was added to 1 ml at the denatured oligodeoxyribonucleotide solution along with 0.1 ml of 6% formaldehyde in 10 mM triethanolamine, pH 7.8. After stirring at 40° for 30 minutes the mixture was dialyzed against the same buffer. The oligodeoxyribonucleotide-biotin complex was finally purified by gel filtration chromatography on Sephadex G-100 followed by precipitation from ethanol.

EXAMPLE VIII

Double stranded polydeoxyadenylic acid:polybiotinylated deoxyuridylic acid was synthesized as follows. The double stranded oligonucleotide polydeoxyadenylic acid:polythymidylic acid (20 ug) of length 300 basic pairs, dissolved in 200 ul exonuclease III buffer consisting of Tris-HCl pH 8.0 (70 mM); magnesium chloride (1.0 mM) and dithiothreitol (10 mM) was incubated with 100 units exonuclease III for 20 minutes at 20° C. The partially digested oligonucleotide was immediately extracted with phenol, and the DNA was precipitated with 70% aqueous ethanol. The partially digested oligonucleotide was redissolved in 20 ul 5 mM tris-HCl pH 7.6 and incubated at 20° C. for 2 hours in a reaction containing 2'-deoxy-adenosine-5'-triphosphate (15 uM) thymidine-5'-triphosphate (the amount determines the degree of substitution) and biotinylated 5-(3-amino-1-propane) 2'-deoxyuridine-5'-triphosphate (5 uM), Klenow DNA polymerase I (200 units) dissolved in 0.1 mM potassium phosphate, pH 8.0 at a concentration of 0.2 units/ul. The biotinylated poly dA:poly dT, biotinyl dU was purified by gel filtration chromatography on Sephadex G-100. The DNA was enthanol precipitated and redissolved in 20 ul of solution containing sodium acetate pH 4.6 (30 mM), sodium chloride (50 mM), zinc sulfate (1 mM) and glycerol (5%). $S_1$ nuclease (200 units) was added, and the reaction was incubated at 37° for 10 minutes. The reaction was stopped with 1 ml ammonium acetate (4 M) and 6 ml ethanol. The DNA was repurified by G-100 gel filtration chromatography and ethanol precipitation.

EXAMPLE IX

Ligation of poly dA:poly dT, biotinyl dU to oligodeoxyribonucleotides was accomplished as follows: DNA fragments from alkali sheared purified DNA (as described in Example VIII) were digested with $S_1$ nuclease and repurified by phenol extraction and ethanol precipitation. Blunt ended DNA fragments (1 ug) and poly dA:poly dT, biotinyl dU (2 ug) were dissolved in 6 ul at a buffer containing tris-HCl pH 7.4 (66 mM), magnesium chloride (6.6 mM), adenosine triphosphate (24 mM) and dithiothreitol (1.0 mM), $T_4$ DNA ligase (50 units) was added, and the volume brought to 20 ul with water. The reaction was incubated 3 hours at 37° C. The DNA was purified by gel filtration chromatography through Sephadex G-100 and was ethanol precipitated.

EXAMPLE X

5-Hydroxymethyl-2'-deoxycytidylic acid was prepared by enzymatic hydrolysis of non glycosylated phage $T_4$ DNA. Purified phage DNA (2 mg), dissolved in 1 ml 50 mM tris pH 7.4 and 10 mM magnesium chloride, was incubated 20 hours with deoxyribonuclease I at 37°. The pH was adjusted to 9.0 and sodium chloride (20 mM) added. Snake venom phosphodiesterase (0.05 g units in 0.5 ml water) was added and incubation continued at 37° for 5 hours. An additional 0.05 units phosphodiesterase was added and incubation continued 18 hours. Nucleotides were separated by gel filtration chromatography through Sephadex G-50. 5-hydroxymethyl-2'-deoxycytidylic acid was purified by reverse phase high pressure liquid chromatography.

EXAMPLE XI 5-(4-aminobutylaminomethyl)-2'-deoxyuridylic acid was obtained by enzymatic hydrolysis of DNA from phage ØW-14. The phage was grown on *Pseudomonas acidovorans* 29 according to Kropinski and Warren, *Gen. Virol.* 6, 85 (1970), and the phage DNA purified according to Kropinski et al, *Biochem.* 12, 151 (1973). The DNA was enzymatically hydrolyzed with deoxyribonuclease I and snake venom phosphodiesterase using the procedure described elsewhere (Example X). 5-(4-aminobutylaminomethyl)-2'-deoxyuridylic acid was purified by reverse phase high-pressure liquid chromatography.

EXAMPLE XII

Biotinylated-5-(4-aminobutylaminomethyl)-2'-deoxyuridylic acid was prepared as follows: Biotinyl-n-hydroxysuccinimide ester (70 mg 0.2 m mol) dissolved in 1 ml dimethylformamide was added to 5-(4-aminobutylaminomethyl)-2'-deoxyuridylic acid in 20 ml 0.1 M sodium borate pH 8.5. After 4 hours the solution was concentrated to 0.5 ml by evaporation, and the biotinylated nucleotide was purified by reverse phase high pressure liquid chromatography.

EXAMPLE XIII 5-formyl-2'-deoxyuridine prepared according to Mertes and Shipchandler, *J. Heterocyclic Chem.* 1, 751 (1970). 5-hydroxymethyluricil (1 mmol) dissolved in 20 ml dimethylsulfonate was heated at 100° C. with manganese dioxide (2.5 mmol) for 15 minutes. The solvent was evaporated at reduced pressure. The residue was taken up in hot ethanol and recrystallized from ethanol to yield 5-formyluracil, 5-formyluracil (0.10 g) was silylated and dissolved in dry acetonitrile (2.5 ml), 2-deoxy-3,5-di-0-p-toluyl-D-ribofuranosyl chloride (Bhat, *Syn. Proc. in Nucleic Acid Chem.*, Vol. I, p. 521 (1968) (0.22 g) and molecular sieves (0.2 g) were added, and the mixture stirred at 25° C. for 40 hours under anhydrous conditions. The mixture was filtered and evaporated. The resulting oil was treated with anhydrous ethanol (2 ml) and chromatographed on silica gel to obtain the partially pure anomer which was recrystallized from ethanol (M.P. 195–196° C.) The toluyl groups were removed by reaction of the product in methanol benzene with sodium methoxide. The mixture was neutralized with Dowex 50 (H⁺). 5-formyl-2'-deoxyuridine was recrystallized from ethanol M.P. 175–176° C.

EXAMPLE XIV

Biotin was coupled to 5-formyl-2'-deoxyuridine as follows: To 5-formyl-2'-deoxyuridine (0.320 g, 1.0 mmol) dissolved in 300 ml 0.05 M sodium borate, was added biotinyl-1,6-diaminohexane amide (0.74 g, 2 mmol). After stirring one hour, sodium borohydride (0.2 g, 5 mmol) was added and stirring continued for an additional 4 hours followed by the addition of 8 ml 1M formic acid. The biotinated compound was purified by reverse phage HPLC eluting with methanol:0.5 M triethyl ammonium acetate, pH 4.0.

EXAMPLE XV

Biotin was coupled to 5-amino-2'-deoxyuridine as follows: 5-amino-2'-deoxyuridine (0.24 g, 1 mmol), biotin (0.25 g, 1 mmol) and dicyclohexylcarbodiimide (0.21 g, 1 mmol) were dissolved in dry dimethyl formamide and stirred at room temperature overnight. After filtration and evaporation of the solvent, the residue was washed with ether. The biotin-coupled product was purified by reverse phase high pressure liquid chromotography using a water methanol gradient.

EXAMPLE XVI 5-(oxy)acetic acid-2'-deoxyuridine was prepared according to a procedure of Deschamps and DeClerq, *J. Med. Chem.*, 21, 228 (1978). 5-hydroxy-2-deoxyuridine (282 mg, 1.15 mmol) was dissolved in 1.16 ml, 1N potassium hydroxide (1.16 mmol) after which iodoacetic acid (603 mg, 3.4 mmol) in 1 ml water was added. After reaction at room temperature for 48 hours 1N HCl (1.06 ml) was added. Concentration of this solution and addition of ethanol yielded a precipitate which was filtered, washed with cold ethanol and recrystallized from hot ethanol.

EXAMPLE XVII

Biotinyl-1,6-diaminohexane amide was coupled to 5-(oxy)acetic acid-2'-deoxyuridine as follows: Biotinyl-1,5-diaminohexane amide (0.74 g, 0.2 mmol), 5-(oxy)acetic acid-2'-deoxyuridine (0.60 g, 0.2 mmol) and Dicyclohexylcarbodiimide (0.41 g, 0.2 mmol) were dissolved in 5 ml dry dimethylformamide and remained overnight at room temperature. The reaction was subsequently filtered and the solvent removed by evaporation. The residue was washed with 0.1N HCl and ether. The biotinated uridine derivative was purified by reverse phase high pressure liquid chromatography using a water-methanol gradient.

EXAMPLE XVIII

Phosphorylation of 5-substituted pyrimidine nucleosides was accomplished by the general procedure described below for biotinated-5-(oxy)acetic acid-2'-deoxyuridine. The nucleoside (0.16 g, 0.5 mmol) was dried by repeated evaporation from dry pyridine and redissolved in 10 ml dry pyridine. Monomethoxytrityl chloride (0.30 g, 0.8 mmol) was added and the mixture stirred at room temperature in the dark for 18 hours. The solution was diluted with chloroform (200 ml) and extracted with 0.1 M sodium bicarbonate. The organic layer was dried and evaporated. The tritylated nucleoside was redissolved in dry pyridine (20 ml) and acetylated by reaction at room temperature with acetic anhydride (0.1 ml, 20 mmol). The mixture was cooled to 4° C. and methanol (40 ml) added. After stirring 10 hours at room temperature, the reaction was concentrated by evaporation. The compound was detritylated by dissolving in 1% benzene sulfonic acid in chloroform (20 ml). After evaporation of solvent the nucleoside was purified by chromatography on silica gel eluting with 2% methanol:chloroform. The 3'-acetylated nucleoside was dried by repeated evaporation of dry pyridine. A mixture of phosphorous oxychloride (100 ul, 1 mmol), 1-H-1,2,4-triazole (140 mg, 2.2 mmol) and triethylamine (260 ul, 2.0 mmol) was stirred in 5 ml anhydrous dioxane at 10°–15° C. for 30 minutes and at room temperature for 1 hour. This was added to the 3'-acetylated nucleoside, and the mixture stirred at room temperature for 1 hour after which it was cooled to 0° C. Water (5 ml) was added and the reaction stirred at room temperature for 18 hours. Barium chloride (100 mg, 5 mmol) was added and the barium salt of the nucleotide collected by filtration. The salt was washed with water and ether. The barium salt was converted to the sodium salt by stirring with Dowex 50 ($Na^+$ form) in 10 ml water for 4 hours at room temperature. 2 N sodium hydroxide (2N, 10 ml) was added and the reaction stirred for 15 minutes at room temperature after which it was neutralized by addition of excess Dowex 50 ($H^+$) form. The deacetylated nucleotide was concentrated by evaporation and purified by reverse phase high-pressure chromatography.

EXAMPLE XIX 5-substituted pyrimidine triphosphates were chemically prepared from their respective 5' monophosphates using a procedure of Michelson, *Biochem Biophys* Acta, 91, 1, (1964). The example of 5-hydroxymethyl-2'-deoxycytidine-5'-triphosphate will be given. The others were similarly prepared. 5-hydroxymethyl-2' deoxycytidylic acid (free acid) (0.63 g, 0.2 mmol) was converted to its tri-n-octylammonium salt by suspending in methanol and addition of tri-n-octylammonium hydroxide (0.74 g, 0.2 mmol). The suspension was refluxed until a clear solution was obtained and the solvent removed under vacuum. The salt was dried by dissolution in and subsequent evaporation from dry pyridine several times. To the salt, dissolved in dry dimethylformamide (0.1 ml) and dioxane (1 ml) was added diphenylphosphochloridate (0.1 ml) and tri-n-butylamine (0.2 ml). After 25 hours at room temperature, solvent was removed and ether was added to precipitate the nucleoside-5'-diphenylpyrophosphate. This was dissolved in dioxane (0.5 ml) and a solution of di(tri-n-butylammonium) pyrophosphate (0.5 mmol) in 1 ml pyridine was added. After 45 minutes at room temperature, the mixture was concentrated under vacuum to a small volume. The crude product was precipitated with ether. This was dissolved in 0.1 M phosphate buffer pH 8.0. The triphosphate was purified by chromatography on DEAE cellulose eluting with a gradient of 0.1 to 0.6 M triethylammonium bicarbonate ph 7.5.

EXAMPLE XX

DNA was labeled with 5-substituted pyrimidine triphosphates by nick translating DNA in the presence of the appropriate triphosphate. An example follows for labeling purified DNA with biotinylated 5-formyl-2'-deoxyuridine. DNA (20 ug/ml) was incubated at 14° C. in the presence of magnesium chloride (5 mM) 2'-deoxycytidine-5'-triphosphate (15 mM), 2'-deoxyadenosine-5'-triphosphate (15 uM), 2'-deoxyguanosine-5'-triphosphate (15 uM), biotinylated-5-formyl-2'-deoxyuridine-5'-triphosphase (20 uM), activated pancreatic deoxyribonuclease I (13 mg/ml), *E. coli* deoxyribonuclease acid, polymerase I (40 units/ml) and tris HCL, pH 7.4 (50 mM). After 2 hours the reaction was stopped by addition of 0.3 M EDTA (0.05 ml) followed by heating at 65° for 5 minutes. Labeled oligonucleotide was purified by gel filtration chromatography through Sephadex G-100 and precipitation from cold ethanol.

EXAMPLE XXI

| PRECIPITATION OF GLUCOSYLATED DNA BY CONCANAVALIN A | |
|---|---|
| Reaction mixtures (1.0 ml) were prepared in 1.5 ml eppendorf tubes as follows: | |
| Sodium potassium phosphate, pH 6.5 | 10 mM |
| NaCl | 150 mM |
| $MgSO_4$ | 5 mM |
| $CaCl_2$ | 1 mM |
| DNA (T4 of calf thymus) | 50 ug |
| Cancanavalin A (10 mg/ml) | 50–500 ug |

Reactions were started by the addition of concanavalin A (Con A). The solutions were mixed and left at room temperature for 60 minutes. The tubes were centrifuged at 1200 g for 15–20 minutes. The supernatants were diluted and the $A_{260}$ was measured.

Since Con A absorbs at 260 nanometers, control solutions lacking DNA but containing Con A were prepared. The Con A absorbance was substracted from the absorbence obtained in the complete reaction mixtures.

The results of this reaction are presented in accompanying FIG. 1.

EXAMPLE XXII

Binding of Glucosylated DNA to Concanavalin A

Phage T4 DNA and phage lamba DNA were labeled by incorporation of $H^3$-deoxyadenosine triphosphate into the DNA by nick translation according to the Rigby et al procedure. T4 DNA was nick translated to a specific activity of $5 \times 10^5$ cpm/microgram and an average double-standed size of 5 kilobases. Lambda DNA was nick translation to a specific activity of $3 \times 10^5$ cpm/microgram and an average double stranded size of 6.0 kilobases as determined by agarose gel electrophoresis. Unincorporated nucleotides were removed from the reaction mixtures by Bio-Gel P-60 chromatography.

Con A sepharose was prepared as described by the manufacturer (Pharmacia). One ml of settled gel contained 18 mg of bound Con A. One ml columns were prepared in sterile pasteur pippetes and were equilibrated with PBS (0.15 M NaCl; 0.01 M sodium potassium phosphate, pH 6.5).

$H^3$-DNA samples were prepared in 0.5 ml of buffer (as described in Example XXI but without Con A). T4 DNA solutions contained 176,000 cpm/0.5 ml, and DNA solutions contained 108,000 cp./0.5 ml. A 0.5 ml sample was applied to the column.

A 10.5 ml volume of buffer was passed through the column, and the eluate fractions (0.33 m) were collected and counted in a Beckman LSC-100 scintillation counter in a 3.5 ml reafluor cocktail (Beckman). The results (FIGS. 2A and 2B) show that non-glucosylated DNA was not bound whereas glucosylated T4 DNA was bound to the column. The bound T4 DNA was removed by washing the column with a higher pH buffer (Tris-HCl, pH 7.2–8.2).

Figure 3B:
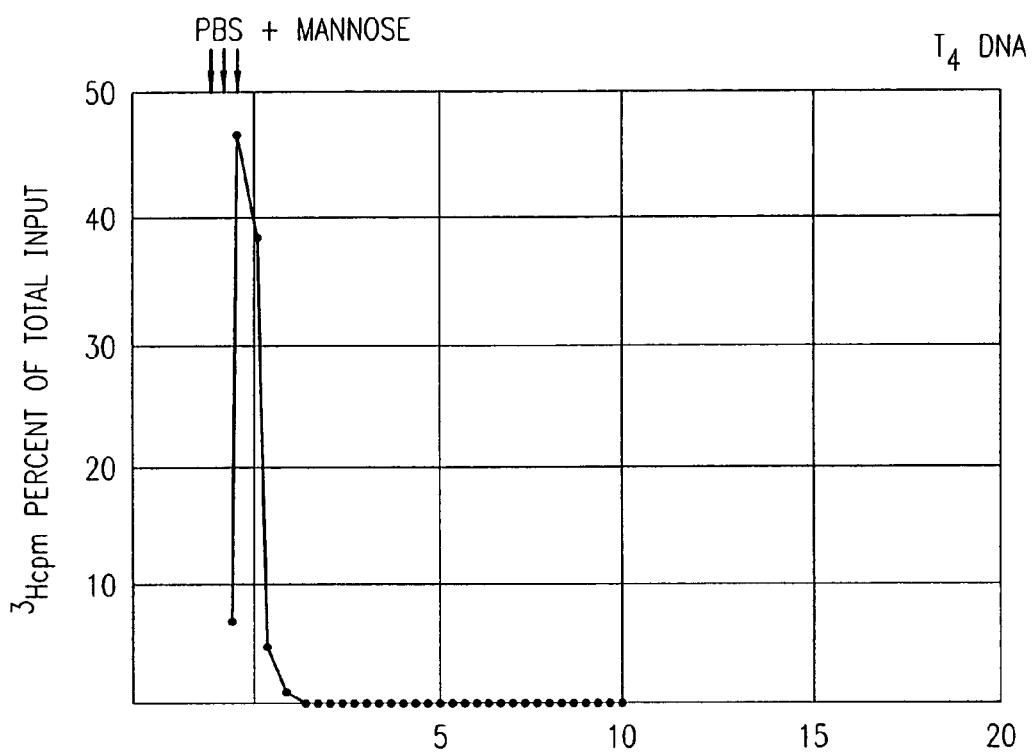
FIG. 3B is a graph that illustrates the recovery (measured as a percent) of tritium labeled T4 DNA using a Con A-sepharose column when mannose is included in the buffer, as described in Example XXII.
Figure 3B:
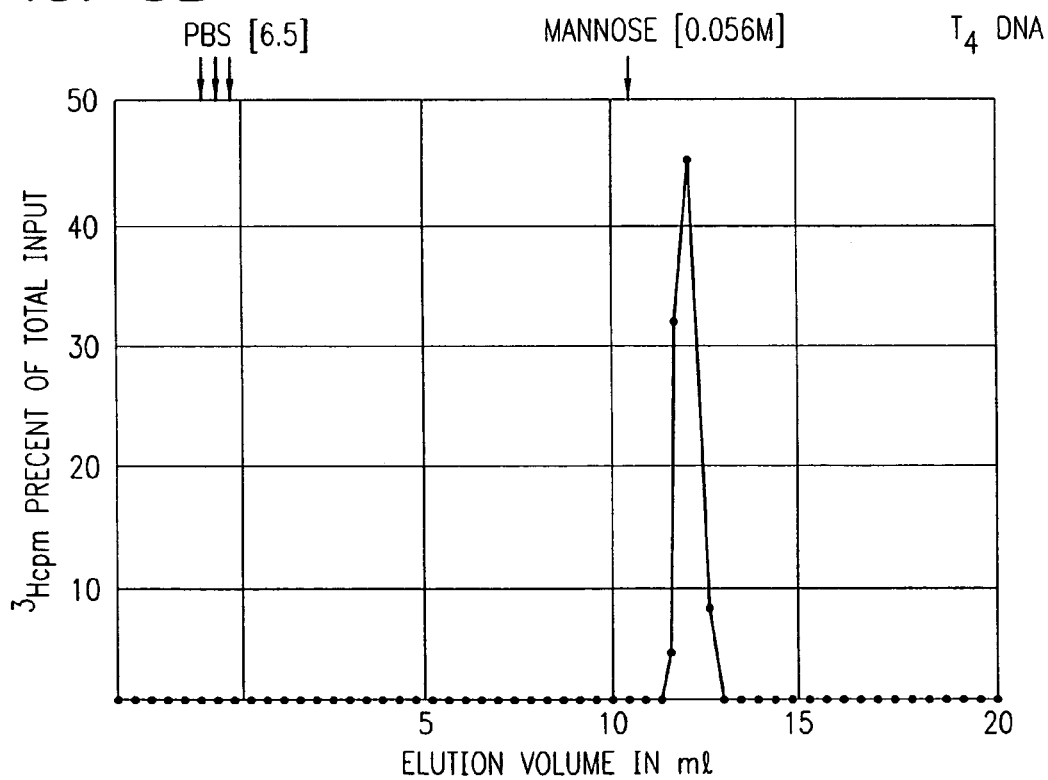

Furthermore, consistent with the interaction of glucose and Con A, mannose, when included in the buffer in which the DNA is applied to the column, prevents binding of glucosylated DNA to Con A sepharose. Also, mannose-containing buffer (PBS-containing 0.056 M mannose) removes bound T4 DNA from Con A sepharose (FIGS. 3A and 3B).

Further illustrative of the practices of this invention directed to nonradioactive methods or techniques of assaying for specific nucleic acids, the following example deals with the use of the sugar-lectin system. This example deals with the use of DNA which is not glycosylated in nature but rather has had a maltotriose group added thereto by way of nick translation described herein. The maltotriose modified dUTP and DNA modified therewith bind specifically to a column of concanvalin A covalently bound to sepharose. By this technique and in accordance with the practices of this invention, there is provided a means for specifically labeling any nucleic acid with sugars. As previously indicated herein, nick translation is only one of a number of techniques and approaches possible for the production of the modified nucleic acids in accordance with this invention.

EXAMPLE XXIII

Lambda DNA was nick translated as described herein wtih maltotriose coupled to 5-(3-amino-1-propenyl)-2'-deoxyuridine-5' triphosphate and $^3$H-2'-deoxyadenosine-5'-triphosphate. Under these conditions DNA was substituted to 40 percent of its thymidine residues with the maltotriose nucleotide and had a specific activity of $8\times10^5$ counts per minute (cpm) per microgram of DNA. A control sample of DNA substituted only with $^3$H-dATP had a specific activity of $6\times10^5$ cpm per microgram DNA. The nick translated DNA samples were purified free of reaction mixture components by Biogel P-60 chromatography as described herein.

Figure 2A:
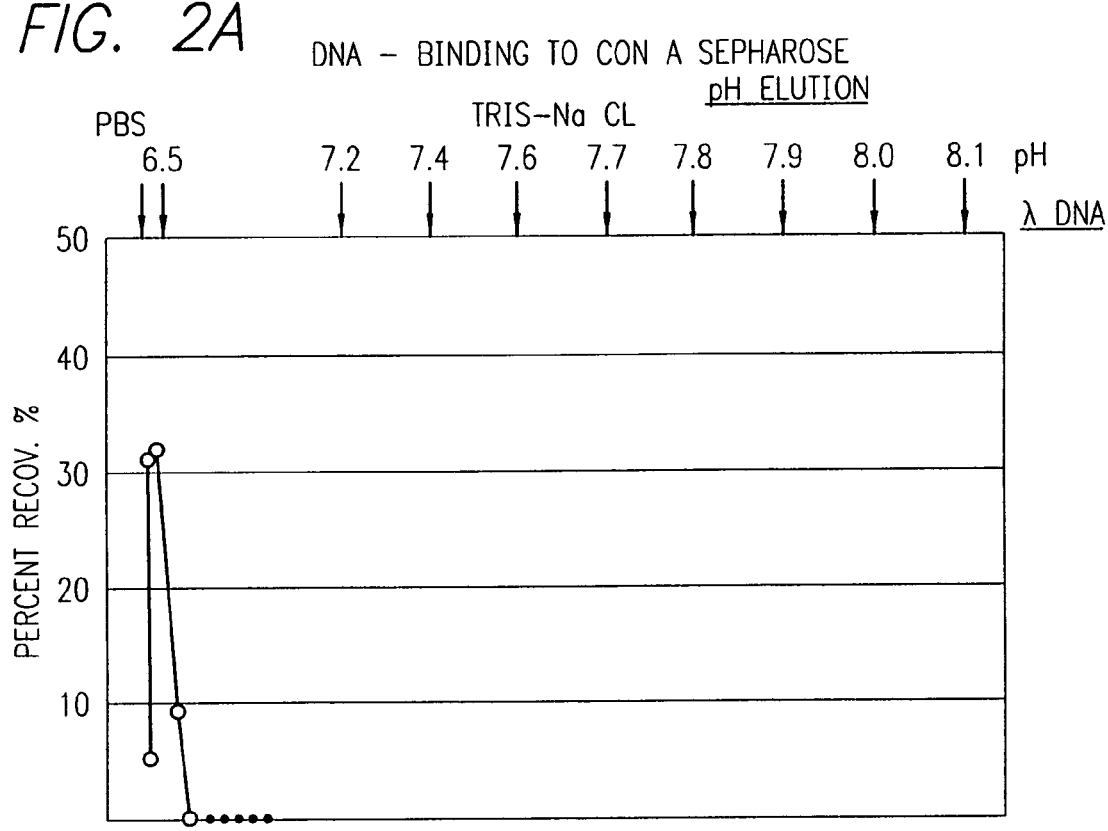
FIG. 2A is a graph that shows the recovery (measured as a percent) of tritium-labeled lambda DNA using a Con A-sepharose column as described in Example XXII. Non-glucosylated DNA was not bound whereas glucosylated DNA was bound to the column.
Figure 2B:
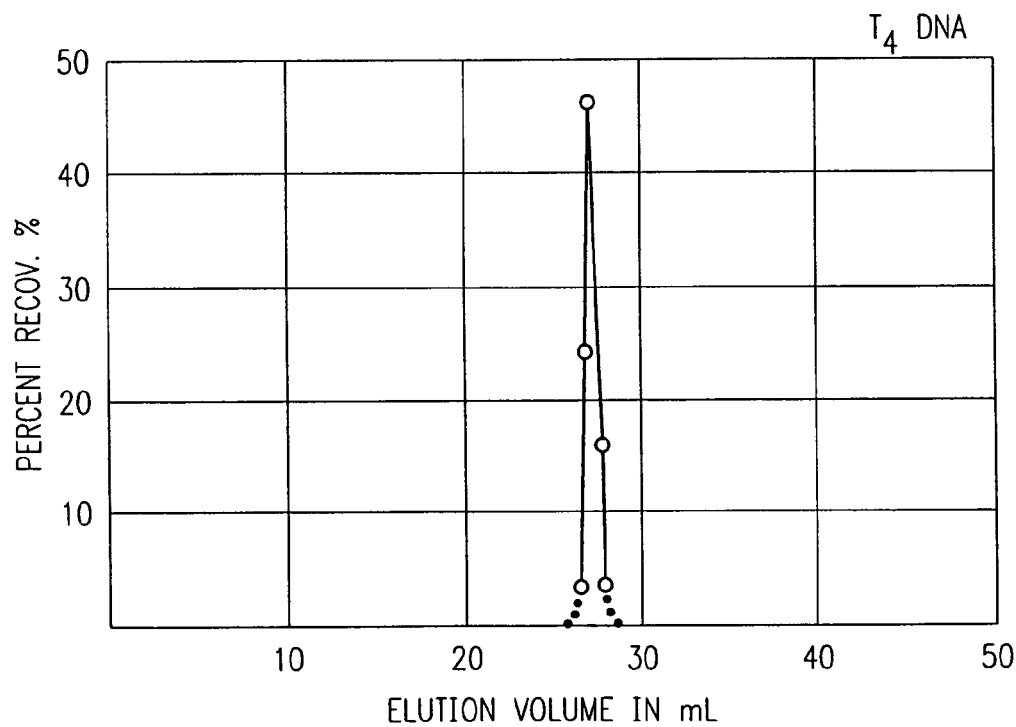
FIG. 2B is a graph that shows the recovery (measured as a percent) of tritium labeled T4 DNA using a Con A-sepharose column as described in Example XXII. Non-glucosylated DNA was not bound whereas glucosylated DNA was column bound.
Figure 4A:
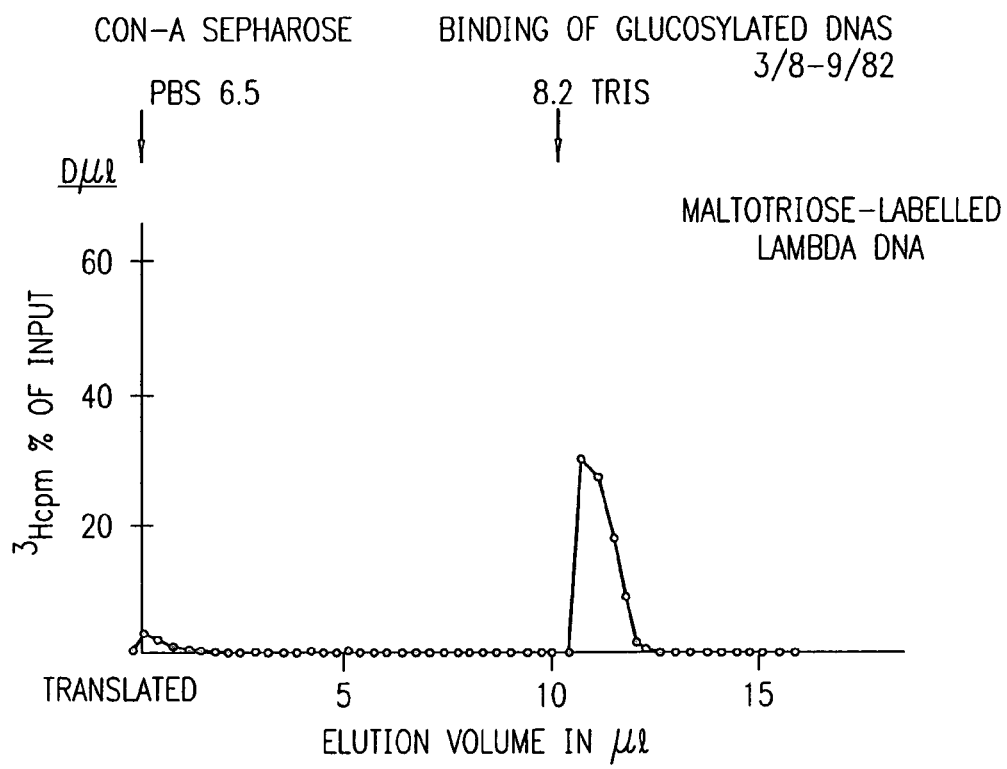
FIG. 4A is a graph that shows the retention of maltotriose labeled lambda DNA using a Con A-sepharose column as described in Example XXIII.
Figure 4B:
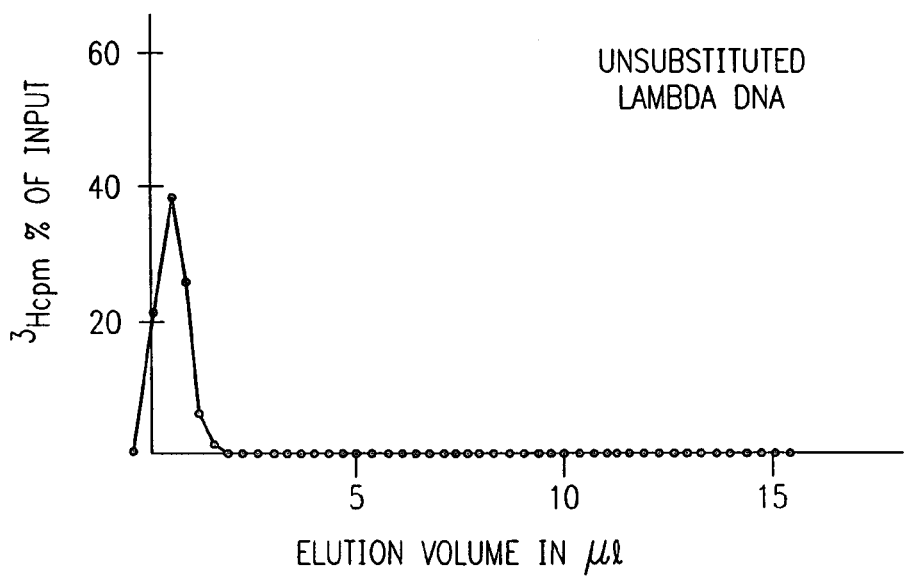
FIG. 4B is also a graph that shows the retention of unsubstituted tritiated lambda DNA using a Con A-sepharose column as described in Example XXIII.

The purified samples were applied to Con A-sepharose columns as described in FIGS. 2A and 2B. The maltotriose-labeled DNA was retained on the column when washed with PBS but was removed by subsequent elution with 10 mM Tris-HCl, pH 8.2 (FIG. 4A). The unsubstituted tritiated DNA did not bind to the column at pH 7.4 (FIG. 4B).

EXAMPLE XXIV

Potentially immunogenic heptenes may be introduced at the 5 position of uridine by a variety of methods in the literature. 5-(perfluorobutyl)-2'-deoxyuridine was synthesized using a method of Cech et al, *Nucl. Acids Res.* 2, 2183 (1979). Copper-bronze was prepared by reacting copper sulfite (5 g, 20 mmol) with zinc powder (2 g) in 20 ml water. The mixture was decanted, and the residue washed with water and then 5% hydrochloric acid and water. Just before use, the solid (2 g) was activated with 2% iodine in acetone (20 ml). After filtration the residue was washed with acetone:concentrated hydrochloric acid and then pure acetone. Activated copper-bronze (130 mg, 2 mmol) and 1-iodo-1',2,2',3,3',4,4'heptafluorobutane (1.3 mg, 4 mmol) were stirred in 3 ml dimethylsulfoxide at 110° C. for 1 hour. After cooling and filtration, 2'-deoxyuridine (245 mg, 1 mmol) was added, and the mixture heated at 110° C. for 1 hour. Water (5 ml) was added, and the mixture extracted with ether. The ether extracts were dried and evaporated under reduced pressure. The residue was chromatographed on a silica gel column eluting with ethylacetate.

EXAMPLE XXV

Tubericydin was substituted at the 5 position by derivitizing the 5-cyano compound, toyocamycin. An example is the synthesis of 4-amino-5 (tetrazol)-5-yl)-7-(β-D-ribofuranosyl) pyrrolo[2,3-d]pyrimidine using a procedure of Schram and Townsend, *J. Carbohydrate*, Nucleosides:Nucleotides 1, 38 (1974). Toyocamycin (1.0 g) dissolved in water (100 ml) and glacial acetic acid (13 ml) was heated to reflux. Sodium azide (7.5 g) was added in 1.25 g portions over 10 hours. The solution was cooled to 5° C. and the precipitated product collected, M.P. 276–277° C.

EXAMPLE XXVI

5-Cyano-2'-deoxyuridine was prepared according to Bleckley et al, *Nucl. Acids Res.* 2, 683 (1975). 5-Iodo-2'-deoxyuridine (1.0 g, 2.82 mmol) was dissolved in refluxing hexamethyldisilizane (HMDS) (10 ml). Excess HMDS was removed at reduced pressure, and the resulting oil was dissolved in dry pyridine (50 ml). Cuprous cyanide (350 mg, 3.8 mmol) was added, and the solution heated at 160° C. for 20 hours. Pyridine was removed at reduced pressure, and the residue extracted into toluene which was subsequently evaporated. The residue was heated in 50% aqueous ethanol at 100° for 2 hours. The product was purified by reverse-phase high pressure liquid chromatography and recrystallized from ethanol, M.P. 161° C.

EXAMPLE XXVII 4-amino-5-amino methylene-7-(β-D-2-deoxyfuranosyl) pyrrolo[2,3-d]pyrimidine dihydrochloride was obtained as follows. 4-amino-5-cyano-7-(β-D-2-deoxyfuranosyl)pyrrolo[2,3-d]pyrimidine (Toyocamycin) (0.2 g) was dissolved in hydrochloric acid (10 ml). 10% palladium on charcoal (0.1 g) was added as the mixture hydrogenated at 40 psi for 5 hours at room temperature. After filtration the water was evaporated at reduced pressure. The residue was triturated with ethanol, and the product recrystallized from 50% ethanol.

EXAMPLE XXVIII 5-amino-2'-deoxyuridine was prepared from 5-bromo-2'-deoxyuridine according to the procedure of Roberts and Visser, *J. Am. Chem. Soc.* 14:665–669 (1952). 5-bromo-2'-deoxyuridine (2 g, 6.2 mmol) dissolved in liquid ammonia (20 ml) was scaled in a glass tube and heated at 50° for 5 days. The tube was opened, and the ammonia was evaporated. 5-amino-2'-deoxyuridine was recrystallized from 5 ml water and 75 ml hot isopropyl alcohol.

EXAMPLE XXIX 5-(methylamino)-2'-deoxyuridine (0.2 g) was prepared as follows. 5-cyano-2'-deoxyuridine (0.2 g, 0.05 mol) was dissolved in 1 N hydrochloric acid (10 ml). 10% palladium on charcoal (0.1 g) was added, and the mixture hydrogenated at 40 p.s.i. for 10 hours at room temperature. The mixture was filtered and the water evaporated at reduced pressure. The residue was triturated with ether, and the product was recrystallized from 80% ethanol.

EXAMPLE XXX

Maltose triose was oxidized to the corresponding carboxylic acid by the following method. Maltose triose (0.5 g, 0.94 mmol) was dissolved in water (5 ml). Lead carbonate (0.42 g, 1.1 mmol) and bromine (0.17 ml), 3.3 mmol) were added, and the mixture was allowed to react at room temperature for six days after which no reducing sugar remained. The mixture was filtered, and silver carbonate (0.2 g) added. After refiltering, the filtrate was deionized by elution through Dowex 50 (H$^+$ form). Evaporation of water and drying in the presence of phosphorus pentoxide yielded the desired product.

EXAMPLE XXXI

Maltose triose was coupled to 5-(3-amino-1-propenyl)-2'-deoxyuridine-5'triphosphate by the following procedure. Oxidized maltose triose (190 mg, 0.18 mmol) was dissolved in dimethylformamide (0.8 ml) and cooled to 4° C. Isobutyl chloroformate (25 mg, 0.18 mmol) and tri-n-butylamine (43 ul, 0.38 mmol) were added, and the solution allowed to react at 4° C. for 15 minutes. 5-(3-amino-1-propenyl)-2'-deoxyuridine-5'-triphosphate (9.0 umol), dissolved in dimethyl formamide (1.2 ml) and 0.1 M sodium borate and cooled to 4° C., was added to the above solution. The mixture was incubated at 4° C. for 1 hour and at room temperature for 18 hours. It was then loaded on a DEAE-cellulose column and eluted with a gradient of 0.1 to 0.6 M triethylammonium bicarbonate, pH 7.5. The product was finally purified by reverse phase high pressure liquid chromatography.

Following are Examples XXXII and XXXIII. Example XXXII is a method of tagging allylamine modified dUTP with a fluorescein substituent. This is an example of creation of a self detecting nucleic acid probe. Example XXXIII is a method of labeling preformed double helical nucleic acids at the N$^2$ position of guanine and the N$^6$ position of adenine. Example XXXVII has the detector molecule linked to the probe. Chromosoma 84:1–18 (1982) and Exp. Cell Res. 128:485–490, disclose end labeling of RNA with rhodamine. However, the procedure of this invention is less disruptive and labels internal nucleotides.

EXAMPLE XXXII

Fluorescein was coupled to 5-(3-amino-1-propyl)-2'-deoxyuridine-5'-triphosphate (AA-dUTP) as follows. AA-dUTP (10 umol), dissolved in 2 ml sodium borate buffer (0.1 m), pH 9.0, was added to fluorescein isothiocyanate (10 mg, 25 umol) dissolved in 1 ml dimethylformamide. After four hours at room temperature the mixture was loaded onto a DEAE-cellulose column equilibrated in triethylammonium bicarbonate buffer, pH 7.5. The fluorescein coupled AA-dUTP was purified by elution with a gradient of from 0.1 to 0.6 m triethylammonium bicarbonate, pH 7.5.

EXAMPLE XXXIII

DNA may be modified by reaction with chemical alkylating agents. Lambda DNA was alkylated in N$^2$ position of guanine and N$^6$ position of adenine by reacting DNA with aromatic hydrocarbon 7-bromomethylbenz[a]anthracene. 7-bromomethylbenz[a]anthracene was obtained as follows. 7-methyl[a]anthracene in carbon disulfide solution was cooled in a freezing mixture and treated dropwise with a molar equivalent of bromine. After 30 minutes, the product in suspension was collected, and was washed with dry ether and recrystallized from benzene. The yield was 66% with melting point 190.5–191.5° C.

DNA, purified from phage Lambda, (1.6 mg) was solubilized in 5.0 ml of 20 mM potassium phosphate pH 6.5. To 4.0 ml of DNA solution was added 500 micrograms 7-bromomethylbenz[a]anthracene in dry acetone. After 30 minutes at 20°, the DNA was precipitated with two volumes of cold ethanol. The precipitate was washed successively with ethanol, acetone and ether to remove any unbound 7-bromomethylbenz[a]anthracene. Enzymatic hydrolysis of the DNA to nucleosides and subsequent chromatography of the products on Sephadex LH-20 columns, indicated that 18% of the adenine and 48% of the guanine in DNA were modified in N$^6$ and N$^2$ positions, respectively.

The modified DNA was made single stranded either by (1) heating to 100° for 5 minutes and rapid cooling or (2) incubating with equal volume of 0.1 M NaOH for 10 minutes and then dialyzing the solution for four hours against 1 ml tris-HCl pH 8.0 containing 0.5 ml EDTA to keep the DNA in single-stranded form.

EXAMPLE XXXIV

A DNA probe was ligated to a synthetic DNA composed of repeated sequences of *E. coli* lac operator DNA. After hybridization to detect antiprobe sequences, the hybridized DNA was detected by reaction with biotinylated lac repressor which was, in turn, detected by an enzyme linked immuno sorbent assay using goat antibiotin IGG to react with the biotin and a second antibody coupled to horse radish peroxidase. The lac polyoperator DNA has been described by Caruthers (Second Annual Congress for Recombinant DNA Research, Los Angeles, 1982), and it was ligated, in a blunt end ligation, using T4 ligase, to an adenovirus DNA probe. In situ hybridization of the polyoperator-labeled probe DNA was carried out as described by Gerhard et al (*Proc. Natl. Acad. Sci.* USA, 78, 3755 (1981). Biotinylated lac repressor was prepared as described by Manning et al (*Chromosoma*, 53, 107–117 (1075) and was applied to adenovirus infected cells, fixed to a glass slide, in Binding buffer composed of (0.01 MK Cl, 0.01 M tris (pH 7.6), 0.01 M MgSO$_4$, 10$^{-4}$ MEDTA, 10$^{-4}$ M DTT, 5% DMSO (dimethyl sulfoxide) and 50 ug/ml bovine serum albumin by J. Miller, *Experiments in Molecular Genetics*, Cold Spring Harbor Laboratory (1972). The slides were washed in binding buffer to remove unbound biotinylated lac repressor and then assayed for biotin using the horse radish peroxidase-linked double antibody procedure. This procedure could be adapted to create an affinity column where the probe could be bound to immobilized repressor protein and then removed by elution with a specific inducer, for example, isopropylthigalactoside or thiomethylgalactoside. The affinity of the repressor-operator complex is quite high 10$^{-11}$ M. When a specific inducer binds to the repressor the operator-repressor complex collapses.

EXAMPLE XXXV

5-Bromo-2'-deoxyuridine-5'-phosphate was prepared as follows: 2'-Deoxyuridine-5'-phosphate (6.2 g) was suspended in a mixture of 60 ml pyridine and 30 ml acetic acid. Bromine (0.84 ml) was added with stirring in an ice water bath and stirring continued for 20 hours at room temperature. The solution was concentrated by vacuum. After redissolution in a minimum of water a crude product was precipitated by addition of ethanol. The crude product was chromatographed on Dowex 50 (H$^+$) and eluted with water. The free acid product was precipitated from the concentrated eluent by addition of ethanol.

EXAMPLE XXXVI

Calf intestine alkaline phosphate was biotinylated as follows: The enzyme (1 mg, 7.7 mmol) was chromatographed on a G-50 column eluting with 0.1 M Hepes buffer pH 8.0 containing 0.1 M sodium chloride. The pooled fractions were reacted with N-biotinyl-6-amino-caproic acid-N-hydroxysuccinimide ester (0.675 mg, 0.77 umol) dissolved in 10 ml dimethylformamide at room temperature for 1 hour. Sodium periodate (0.1 M 125 ul) was added and stirring continued for 2 hours. The mixture as dialyzed at 4° overnight in 0.1 M. Hepes buffer pH 8.0 with 0.1 M NaCl after which the pH was adjusted to 7.4. Biotin hydrazide (0.1 M, 0.5 ml) dissolved in 0.1 M Hepes buffer pH 7.4 and 0.1 M NaCl was added and the reaction stirred for 30 minues at room temperature. The pH was adjusted to 8.0 with 0.2 M sodium carbonate and 0.5 ml of freshly prepared 0.1 M sodium borohydride in water was added, the solution was dialyzed against 0.1 M tris buffer pH 8.0 with 0.1 M NaCl.

EXAMPLE XXXVII

6-Cyano-2'-deoxyuridine-5'-phosphate was prepared similarly to a procedure of Veder et al, *J. Carbohydr. Nucleosides, Nucleotides*, 5, 261 (1978). 5-bromo-2'-deoxyuridine-5'-phosphoric acid (2.0 g, 15 mmol) dried by successive evaporation from pyridine was dissolved in 50 ml dimethylsulfide. Sodium cyanide (490 mg, 10 mmol) was added and the solution stirred at room temperature for 2 days. The solution was diluted with 400 ml water and the pH adjusted to 7.5. It was applied to a DEAE-cellulose column ($HCO_3^-$ form) washed with 2000 ml 0.02 M triethylammonium bicarbonate to yield the desired product.

EXAMPLE XXXVIII 6-(Methylamino)-2'-deoxyuridine-5'-phosphoric acid was prepared as follows: 6-Cyano-2'-deoxyuridine-5'-phosphoric acid (0.2 g, 60 mmol) was dissolved in 0.1 M hydrochloric acid. After addition of 10% palladium on charcoal (0.1 g), the mixture was hydrogenated at 40 psi for 20 hours at room temperature. The mixture was filtered, neutralized with lithium hydroxide and lyophilized. The product residue was extracted with ethanol.

EXAMPLE XXXIX

Horse radish peroxidase (20 mg) dissolved in 5 ml distilled water was added to 1.0 ml freshly prepared 0.1 M sodium periodate solution. After stirring at room temperature for 20 minutes it was dialyzed overnight at 4° C. against 1 mM sodium acetate pH 4.4. Biotin hydrazide (2.6 mg, 5×10–2 mmol) dissolved 2.0, 0.1 M Hepes buffer pH 7.4 with 0.1 M sodium chloride was brought to pH 8.0 with 0.2 M sodium carbonate and 0.5 ml of a freshly prepared 0.1 M sodium borohydride solution in water was added. After 2 hours at 4° C. the protein was purified on a Sephadex G-50 column eluting with 0.1 M Hepes and 0.1 M NaCl.

EXAMPLE XL

Carrot acid phosphatase has been mentioned by Brunngraber and Chargaff, *J. Biol Chem.*, (1967) 242, 4834–4840 as a byproduct of the purification of phosphotransferase and has been purified to a specific activity of 460 uM/mg/min at 37° C. with paranitrophenylphosphate as the substrate. The purification involved the steps of (a) absorption of nonspecific proteins by DEAE cellulose; (b) acid purification of the enzyme; (c) acetone fractionation; (d) concanvalin A affinity chromatography; (e) hydroxyapatite chromatography and (f) Sephadex G-100 fractionation. The specific activity of the enzyme subjected to the Sephadex G-100 fractionation due to loss of activity in the preceding affinity chromatography step (d) was 170 uM/mg/m. By changing elution conditions at step (d), these losses can be avoided with the result that the specific activity of the enzyme before the Sephadex G-100 fractionation can be improved to 340 uM/mg/m. The Sephadex G-100 fractionation step should yield an enzyme having a specific activity of 800 uM/mg/m or higher. Carrot acid phosphatase was biotinylated using a procedure of Wilchek et al *Biochemistry* 6, 247 (1967). To the enzyme (20 mg) dissolved 0.1 M NaCl, pH 5, was added biotin hydrazide (2.0 mg, 7×10$^{-3}$ mmol) and 1-ethyl-3-(3-dimethylaminopropyl) carbodiimide hydrochloride (1 mg, 7×10$^{-3}$ mmol) dissolved in 0.1 M NaCl, pH 5. After 2 hours at 4° C. the enzyme was chromatographed on Sephadex G-50 eluting with 0.1 M sodium acetate, pH 5.0.

Of special importance and significance in the practices of this invention is the utilization of self-signaling or self-indicating or self-detecting nucleic acids, particularly such nucleic acids which are capable of being incorporated in double-stranded DNA and the like. Such self-signaling or self-detecting nucleic acids can be created by covalently attaching to an allylamine substituent making up a modified nucleotide in accordance with this invention a molecule which will chelate specific ions, e.g. heavy metals, rare earths, etc. In general, the chelated ion can be detected either (a) by radioactive emission or (b) by using the ion to catalyze a chromogenic or fluorogenic reaction.

By way of example, a solution of 3,4-dinitro phenol is reduced to 3,4-diamino cyclohexane

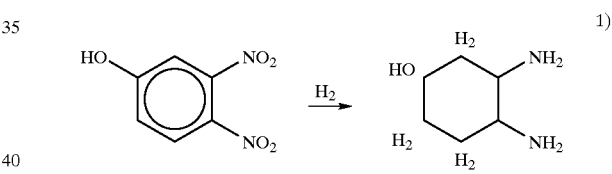

This material is then brominated

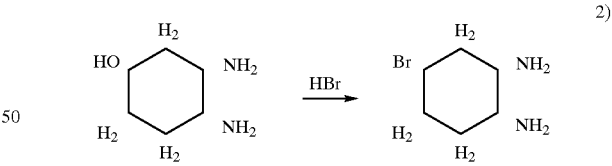

to form 3,4-diamino bromo cyclohexane (dABCH). This compound is reacted with halide (Cl, Br, I) substituted carboxymethyl compound to produce a tetra carboxymethyl derivative or dABCH (TCM-dABCH):

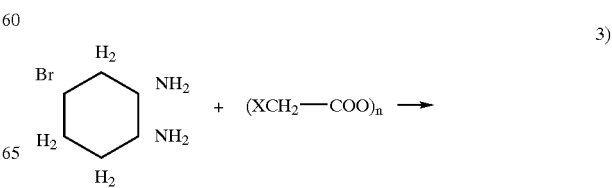

-continued

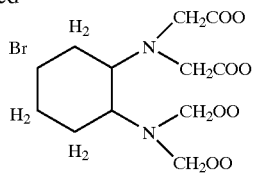

The bromine is substituted by an amino group using soluble ammonia:

4)

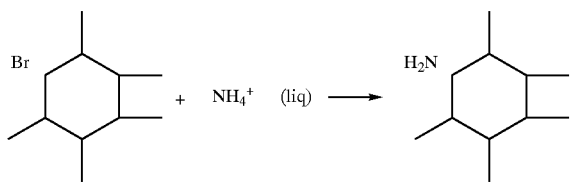

Then this compound is reacted with chloro thiophosgene to produce the isothiocyanate derivative of (TCM-dANCH).

5)

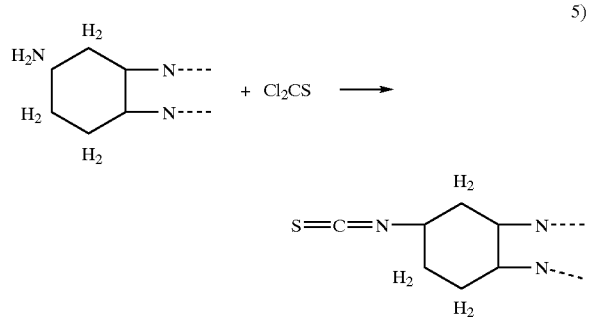

Finally, this compound is reacted with dUTP-allylamine derivative to produce modified dUTP.

6)

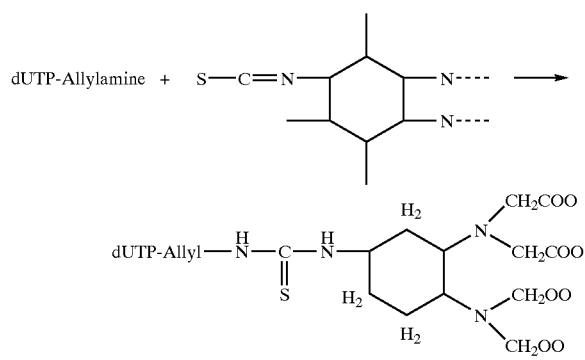

Cobalt or other heavy metal ions or other rare earth ions can be chelated to the compound after step 3 above. Or the nucleic acid can be substitued with this adduct and then the ion added. (Example, cobalt is added at pH 6 where the binding constant is $10^{-19}$M).

Cobalt can be assayed by radioactivity. It can also be detected by its ability to oxidize methylene blue to the leuco form in the presence of molecular oxygen. It can be used to oxidize soluble sulfhydro groups to disulfide bonds again in the presence of molecular oxygen.

This type of self-signaling molecule can be used to monitor any nucleic acid hybridization reaction. It is particularly important for detecting nucleic acids in gels (for example, sequencing gels).

With respect to its use in radioactivity, it can be used to tailor the isotype needed, i.e. if a weak or strong β or α emitter is needed, that isotope can be chelated. Examples of isotopes that can be used are listed immediately hereinafter.

| | | |
|---|---|---|
| Antimony-124 | Iodine-125 | Scandium-44 |
| Antimony-125 | Iodine-131 | Scandium-46 |
| Arsenic-74 | Iodine-132 | Selenium-75 |
| Barium-133 | Iridium-192 | Silver-110m |
| Barium-140 | Iron-55 | Silver-111 |
| Beryllium-7 | Iron-59 | Sodium-22 |
| Bismuth-206 | Krypton-85 | Strontium-85 |
| Bismuth-207 | Lead-210 | Strontium-89 |
| Cadmium-109 | Lutetium-177 | Strontium-90 |
| Cadmium-115m | Manganese-54 | Sulphur-35 |
| Calcium-45 | Mercury-197 | Tantaium-182 |
| Carbon-14 | Mercury-203 | Technetium-99 |
| Cerium-139 | Molybdenum-99 | Tellurium-125m |
| Cerium-141 | Neodymium-147 | Tellurium-132 |
| Cerium-144 | Neptunium-237 | Terbium-160 |
| Cesium-134 | Nickel-63 | Thallium-204 |
| Cesium-137 | Niobium-95 | Thorium-228 |
| Chlorine-36 | Osmium-185 + 191 | Thorium-232 |
| Chromium-51 | Palladium-103 | Thulium-170 |
| Cobalt-56 | Platinum-195m | Tin-113 |
| Cobalt-57 | Praseodymium-143 | Titanium-44 |
| Cobalt-58 | Promethium-147 | Tritium |
| Cobalt-60 | Protactinium-233 | Tungsten-185 |
| Erbium-169 | Radium-226 | Vanadium-48 |
| Europium-152 | Rhenium-186 | Vanadium-49 |
| Gadolinium-153 | Rubidium-86 | Ytterbium-169 |
| Gold-195 | Ruthenium-103 | Yttrium-88 |
| Gold-199 | Ruthenium-106 | Yttrium-90 |
| Hafnium-175 | | Yttrium-91 |
| Hafnium-175 + 181 | | Zinc-65 |
| Hafnium-181 | | Zirconium-95 |
| Hydrogen-3 see Tritium | | |

Streptavidin, a protein produced by a *Streptomyces avidinii* is a large molecular weight component of a synergistic pair of compounds which are both present in the culture filtrates of this microorganism. Each of the pair is inactive but in combination are active against gram-negative microorganisms. It has been found that the small component of this antibiotic prevents de novo synthesis of the vitamin biotin and thus, at least in synthetic media, show antimicrobial activity. In complex medium, however, the large component has to be included to exert the same effect on bacteria. This has been shown to be due to the presence of external biotin in the complex medium. The large molecular component has been found to bind external biotin and thus demonstrating the same kind of action as avidin from eggs and oviduct tissues of laying birds.

Streptavidin has been purified and shown to be a 60,000 dalton polypeptide. Like avidin, streptavidin contains four subunits and binds tightly four molecules of biotin. Unlike avidin, however, it is non-glycosylated and it has PI of 5.0 as compared to avidin with PI=10.5. Due to the difference in pI streptavidin does not have a tendency to non-specifically interact with DNA.

Preparation of Streptavidin

A semi-synthetic medium containing salt, 1% glucose, 0.1% asparagine, 0.05% yeast extract and trace elements was prepared. The cultures were grown at 26° C. for three days. Mycellium was removed by centrifugation and protein in the supernatant were absorbed to DEAE-cellulose in a batchwise process after pH was adjusted with 1M HCl to 7.2. DEAE-cellulose was filtered off and washed with 20 mM Tris-HCl (pH 7.2) until no absorbancy at 280 nm was recorded. Streptavidin was eluted with 20 mM Tris-HCl (pH 7.2) containing 0.5 M NaCl. Ammonium sulfate precipitation was used to further concentrate the streptavidin (50% w/v at 4° C.).

The precipitate was dissolved in water and dialyzed against 1.0 M NaCl, 50 mM $Na_2CO_3$. In the next step affinity column chromatography on iminobiotin sepharose was used. Eluted streptavidin from iminobiotin sepharose column was shown to be chromatographically pure by non-denaturing agarose-gel electrophoresis.

The final purification of streptavidin is accomplished by affinity purification through an iminobiotin-sepharose column. Iminobiotin is an analog of biotin in which the carbonyl of the urea moiety is substituted with an imine function. Iminobiotin will bind avidin and streptavidin at basic pH but the complex is dissociable at acidic pH.

Iminobiotin is prepared from biotin in several steps. Biotin is hydrolyzed by barium hydroxide to cis-3,4-diamino-2-tetrahydrothiophene-valeric acid which is reacted with cyanogen bromide to iminobiotin. The iminobiotin is coupled to amino sepharose via the N-hydroxysuccinimide ester of its hydrobromide salt.

The crude protein mixture from DEAE eluted *Streptomyces avidinii* incubation media is dissolved in 50 mM sodium carbonate and 1.0 M sodium chloride (pH 11) and applied to an iminobiotin column pre-equilibrated with this solution. The column is eluted at pH 11. Streptavidin is subsequently eluted with 50 mM ammonium acetate, pH 4.0 containing 0.5 M sodium chloride. The eluent is diaylzed three times against 1 mM Tris pH 7.4 and lyophilized to dryness.

In the practices of this invention avidin is useful as a detecting mechanism for labeled DNA, such as biotin-labeled DNA. However, avidin itself, such at about neutral pH, complexes with DNA with the result that any signal derivable from a complex between biotin-labeled DNA and avidin might be lost or be non-detectable in the background due to the complex formation between avidin and unlabeled DNA. This disadvantage of the use of avidin in the practices of this invention is not possessed by streptavidin which does not form a complex with DNA at about neutral pH but is capable of forming a complex with the biotin portion of biotin-labeled DNA.

In another aspect directed to the broad utility of avidin and streptavidin for detecting labeled compounds other than DNA, avidin and streptavidin are particularly effective as detecting mechanisms for labeled proteins, polysaccharides and lipids. By way of example, one can fix to a solid matrix a specific antigen and bind to this antigen an antibody directed against this antigen which itself has been biotinylated. Then one can assay for the presence of this biotinylated antibody by reacting it with avidin or streptavidin complexed with an enzyme, such as calf intestine alkaline phosphatase, or to which fluorescing molecule, as for example fluoroscein has been linked.

The use of the antigen-antibody system for detecting either antigen or antibody is well known. A comparable system is a system based on a glycosylated substrate or molecule and matching or appropriate lectin. In this system the lectin would carry a label, such as fluorescein or appropriate enzyme. In this glycosyl-lectin system the labeled lectin forms a complex with the glycosyl moiety, comparable to the antigen-antibody complex, and this complex comprising the glycosylated molecule and appropriate labeled lectin having the necessary glycosyl or sugar moiety specificity would then present itself eliciting the expected response from the label portion of the labeled lectin making up the glycosyl-lectin complex.

Another aspect of the practices of this invention which is particularly advantageous is to carry out the detection or hybridization in the liquid phase between the DNA sought to be detected and the DNA detecting probe. In this liquid phase system both the DNA molecule to be detected and the appropriate DNA detecting probe are not attached to any insoluble substrate or any insoluble chemical moiety. The advantages of the liquid phase detection system reside in the speed of hybridization or hybrid formation between the DNA to be detected and the appropriate DNA probe therefor. For example, in a solid-liquid system the time required to effect recognition and hybridization formation is about ten times greater than if it were carried out in a completely liquid system, i.e. both DNA to be detected and the detecting DNA are not attached to an insoluble moiety.

The probes prepared in accordance with the practices of this invention are adaptable for use in the detection of viruses and bacteria in fluids as indicated hereinabove. Where the fluids to be examined do not contain large amounts of protein, the viruses therein can be concentrated by absorption on hydroxyapatite and eluted in a small amount of phosphate buffer. When the fluid to be examined contains large amounts of protein, the viruses can be concentrated by high speed centrifugation.

If antibody were available, absorption on an affinity column and elution with acid would be preferable because it would be possible to process many probes in accordance with the practices of this invention at the same time. The bacteria to be examined is usually readily concentrated by centrifugation.

In accordance with the practices of this invention, the identification or characterization of the isolated particles, viruses and bacteria, would be hybridization of the characterizing or identifying DNA thereof with a specific single stranded DNA probe prepared in accordance with the practices of this invention. After hybridization, excess non-hybridized probe DNA would be digested with $S_1$ nuclease and exonclease I from *E. coli* at high salt content to suppress the nicking activity of the $S_1$ nuclease, see Vogt, *Methods in Enzymology*, Vol. 65, pages 248–255 (1980). This nuclease treatment would produce mononucleotides from the excess, non-hybridized single-stranded DNA probe but would leave the double-stranded, hybridized DNA intact. This would then be absorbed at high salt content on Dowex anion exchanger (the nucleotides and the small amount of oligonucleotides will not bind to the resin in high salt concentration). The resulting hybridized DNA would then be identified or characterized by various procedures applicable to the practices of this invention.

The special nucleotides of this invention include a phosphoric acid P moiety (also designated hereinbelow as "PM"), a sugar or monosaccharide S moiety (also designated hereinbelow as "SM"), a base B moiety (also designated hereinbelow as "BASE"), a purine or a pyrimidine and a signalling chemical moiety Sig covalently attached thereto, etiher to the P, S or B moiety (referred to hereinbelow as "PM," "SM" and "BASE," respectively). Following are structural formulas of various base B moieties (BASE) and nucleotides which are modified in accordance with the practices of this invention.

---

The major purines

Adenine
(6-aminopurine)

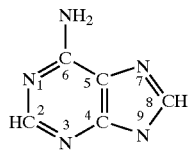

Guanine
(2-amino-6-oxypurine)

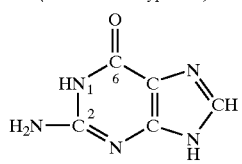

Two minor purines

2-Methyladenine

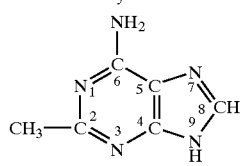

1-Methylguanine

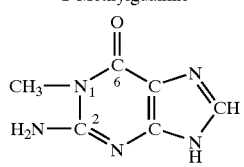

The major pyrimidines

Cytosine
(2-oxy-4-aminopyrimidine)

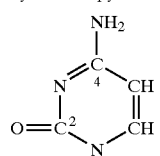

Uracil
(2,4-dioxypyrimidine)

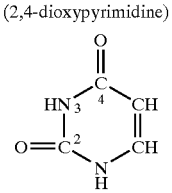

Thymine
(5-methyl-2,4-dioxypyrimidine)

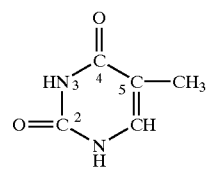

Two minor pyrimidines

5-Methylcytosine

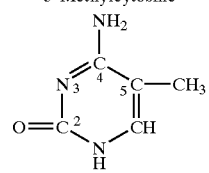

5-Hydroxymethylcytosine

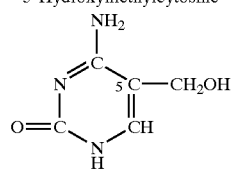

PYRIMIDINE

PURINE

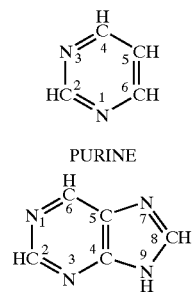

The major ribonucleotides and deoxyribonucleotides.

Ribonucleoside
5'-monophosphates

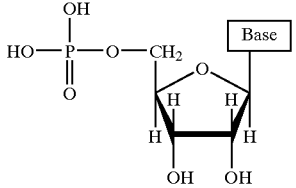

2'-Deoxyribonucleoside
5'-monophosphates

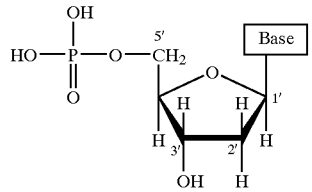

General Structure Names

Adenosine 5'-phosphoric acid
(adenylic acid; AMP)
Guanosine 5'-phosphoric acid
(guanylic acid; GMP)

-continued

Cytidine 5'-phosphoric acid
(cytidylic acid; CMP)
Uridine 5'-phosphoric acid
(uridylic acid; UMP)
Deoxyadenosine 5'-phosphoric acid
(deoxyadenylic acid; dAMP)
Deoxyguanosine 5'-phosphoric acid
(deoxyguanylic acid; dGMP)
Deoxycytidine 5'-phosphoric acid
(deoxycytidylic acid; dCMP)
Deoxythymidine 5'-phosphoric acid
(deoxythymidylic acid; dTMP)

The special nucleotides in accordance with this invention, as indicated hereinabove, in addition to the P, S and B moieties (PM, SM and BASE, respectively), include a chemical moiety Sig coavalently attached to the P, S and/or B moieties (PM, SM and BASE, respectively). Of special interest in accordance with the practices of this invention would be those nucleotides having the general formula, P-S-B-Sig (PM-SM-BASE-Sig) wherein P (PM) is the phosphoric acid moiety including mono-, di-, tri-, or tetraphosphate, S (SM) the sugar or monosaccharide moiety, B the base moiety (BASE), either a purine or a pyrimidine. The phosphoric acid moiety P (PM) is attached at the 3' and/or the 5' position of the S moiety (SM) when the nucleotide is a deoxyribonucleotide and at the 2', 3' and/or 5' position when the nucleotide is a ribonucleotide. The base B moiety (BASE) is attached from the N1 position or the N9 position to the 1' position of the S moiety (SM) when the base moiety is a pyrimidine or a purine, respectively. The Sig moiety is covalently attached to the B moiety (BASE) of the nucleotide and when so attached is capable of signalling itself or makes itself self-detecting or its presence known and desirably or preferably permits the incorporation of the resulting nucleotide P-S-B-Sig (PM-SM-BASE-Sig) into or to form a double-stranded helical DNA or RNA or DNA-RNA hybrid and/or to be detectable thereon.

Another special nucleotide in accordance with this invention is characterized by the general formula:

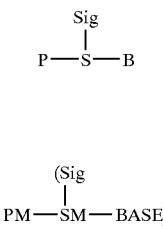

Such nucleotides in accordance with this invention would be characterized as ribonucleotides. The phosphoric acid moiety (PM) is attached at the 2', 3' and/or 5' position of the sugar S moiety (SM) and the base B (BASE) being attached from the N1 position or the N9 position to the 1' position of the sugar S moiety (SM) when said base (BASE) is a pyrimidine or a purine, respectively. The Sig chemical moiety is covalently attached to the sugar S moiety (SM) and said Sig chemical moiety when attached to said S moiety (SM) is capable of signalling itself or making itself self-detecting or its presence known and preferably permits the incorporation of the ribonucleotide into its corresponding double-stranded RNA or a DNA-RNA hybrid.

Such nucleotides

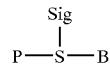

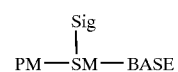

desirably have the Sig chemical moiety attached to the C2' position of the S moiety (SM) or the C3' position of the S moiety (SM).

Still further, nucleotides in accordance with the practices of this invention include the nucleotides having the formula,

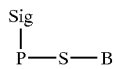

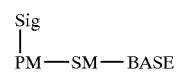

wherein P (PM) is the phosphoric acid moiety, S the sugar moiety (SM) and B (BASE) the base moiety. In these special nucleotides the P moiety (PM) is attached to the 3' and/or the 5' position of the S moiety SM when the nucleotide is deoxyribonucleotide and at the 2', 3' and/or 5' position when the nucleotide is a ribonucleotide. The base B (B) is either a purine or a pyrimidine and the B moiety (BASE) is attached from the N1 or the N9 position to the 1' position of the sugar moiety when said B moiety (BASE) is a pyrimidine or a purine, respectively. The Sig chemical moiety is covalently attached to the phosphoric acid P moiety (PM) via the chemical linkage

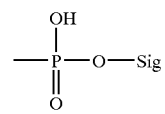

said Sig, when attached to said P moiety (PM) being capable of signalling itself or making itself self-detecting or its presence known and desirably the nucleotide is capable of being incorporated into a double-stranded polynucleotide, such as DNA, RNA or DNA-RNA hybrid and when so incorporated therein is still self-detecting.

It is pointed out that the special nucleotides in accordance with the practices of this invention described or defined hereinabove by the general formula P-S-B-Sig (PM-SM-BASE-Sig), also include nucleotides wherein the Sig chemical moiety is covalently attached to the B moiety (BASE) at the $N^6$ or 6-amino group position when the B moiety (BASE) is adenine or the $N^2$ or 2-amino group position when the B moiety (BASE) is guanine or the $N^4$ or 4-amino group position when the B moiety is cytosine. The resulting nucleotides containing the Sig moiety attached thereto are capable of signalling themselves or making themselves self-detecting or their presence known and being detectable is a double-stranded or DNA, RNA or DNA-RNA hybrid.

By way of summary, as indicated hereinabove with respect to the make-up of the various special nucleotides in accordance with this invention, the special nucleotides can be described as comprising a phosphoric acid moiety P (PM), a sugar moiety S (SM) and a base moiety B (BASE), a purine or pyrimidine, which combination of P-S-B (PM-SM-BASE) is well known with respect to and defines nucleotides, both deoxyribonucleotides and ribonucleotides. The nucleotides are then modified in accordance with the practices of this invention by having covalently attached thereto, to the P moiety (PM) and/or the S moiety (SM) and/or the B moiety (BASE), a chemical moiety Sig. The chemical moiety Sig so attached to the nucleotide P-S-B (PM-SM-BASE) is capable of rendering or making the resulting nucleotide, now comprising P-S-B (PM-SM-BASE) with the Sig moiety being attached to one or more of the other moieties, self-detecting or signalling itself or capable of making its presence known per se, when incorporated into a polynucleotide, especially a double-stranded polynucleotide, such as a double-stranded DNA, a double-stranded RNA or a double-stranded DNA-RNA hybrid. The Sig moiety desirably should not interfere with the capability of the nucleotide to form a double-stranded polynucleotide containing the special Sig-containing nucleotide in accordance with this invention and, when so incorporated therein, the Sig-containing nucleotide is capable of detection, localization or observation.

The Sig moiety employed in the make-up of the special nucleotides of this invention could comprise an enzyme or enzymic material, such as alkaline phosphatase, glucose oxidase, horseradish peroxidase, ribonuclease, acid phosphatase or B-galactosidase. The Sig moiety could also contain a fluorescing component, such as fluorescein or rhodamine or dansyl. If desired, the Sig moiety could include a magnetic component associated or attached thereto, such as a magnetic oxide or magnetic iron oxide, which would make the nucleotide or polynucleotide containing such a magnetic-containing Sig moiety detectable by magnetic means. The Sig moiety might also include an electron dense component, such as ferritin, so as to be available by observation. The Sig moiety could also include a radioactive isotope component, such as radioactive cobalt, making the resulting nucleotide observable by radiation detecting means. The Sig moiety could also include a hapten component or per se be capable of complexing with an antibody specific thereto. Most usefully, the Sig moiety is a polysaccharide or oligosaccharide or monosaccharide, which is capable of complexing with or being attached to a sugar or polysaccharide binding protein, such as a lectin, e.g. Concanavilin A. The Sig component or moiety of the special nucleotides in accordance with this invention could also include a chemiluminescent component.

As indicated in accordance with the practices of this invention, the Sig component could comprise any chemical moiety which is attachable either directly or through a chemical linkage or linker arm to the nucleotide, such as to the base B component (BASE) therein, or the sugar S component (SM) therein, or the phosphoric acid P component (PM) thereof.

The Sig component of the nucleotides in accordance with this invention and the nucleotides and polynucleotides incorporating the nucleotides of this invention containing the Sig component are equivalent to and useful for the same purposes as the nucleotides described in the above-identified U.S. patent application Ser. No. 255,223, now U.S. Pat. No. 4,711,955. More specifically, the chemical moiety A described in U.S. patent application Ser. No. 255,223 is functionally the equivalent of the Sig component or chemical moiety of the special nucleotides of this invention. Accordingly, the Sig component or chemical moiety of nucleotides of this invention can be directly covalently attached to the P, S or B moieties (PM, SM or BASE, respectively) or attached thereto via a chemical linkage or linkage arm as described in U.S. patent application Ser. No. 255,223, as indicated by the dotted line connecting B and A of the nucleotides of U.S. Ser. No. 255,223. The various linker arms or linkages identified in U.S. Ser. No. 255,223 are applicable to and useful in the preparatin of the special nucleotides of this invention.

A particularly important and useful aspect of the special nucleotides of this invention is the use of such nucleotides in the preparation of DNA or RNA probes. Some probes would contain a nucleotide sequence substantially matching the DNA or RNA sequence of genetic material to be located and/or identified. The probe would contain one or more of the special nucleotides of this invention. A probe having a desired nucleotide sequence, such as a single-stranded polynucleotide, either DNA or RNA probe, would then be brought into contact with DNA or RNA genetic material to be identified. Upon the localization of the probe and the formation of a double-stranded polynucleotide containing the probe and the matching DNA or RNA material to be identified, the resulting formed double-stranded DNA or RNA-containing material would then be observable and identified. A probe in accordance with this invention may contain substantially any number of nucleotide units, from about 5 nucleotides up to about 500 or more, as may be required. It would appear that 12 matching, preferably consecutive, nucleotide units would be sufficient to effect an identification of most of the DNA or RNA material to be investigated or identified, if the 12 nucleotide sequence of the probe matches a corresponding cooperative sequence in the DNA or RNA material being investigated or to be identified. As indicated, such probes may contain one or more of the special Sig-containing nucleotides in accordance with this invention, preferably at least about one special nucleotide per 5–10 of the nucleotides in the probe.

As indicated hereinabove, various techniques may be employed in the practices of this invention for the incorporation of the special nucleotides of this invention into DNA and related structures. One particularly useful technique referred to hereinabove involves the utilization of terminal transferase for the addition of biotinated dUMP onto the 3' ends of a polypyrimidine or to single-stranded DNA. The resulting product, such as a single-stranded or cloned DNA, which has biotinated dUMP attached to the 3' ends thereof, can be recovered by means of a Sepharose-avidin column wherein the avidin would complex with the biotinated dUMP at the ends of the DNA and be subsequently recovered. In accordance with the practices of this invention hybridization to mRNA could be accomplished in solution and the resulting hybrid recovered via a Sepharose-avidin column and the mRNA recovered therefrom. Similar techniques could be employed to isolate DNA-RNA hybrids. This technique employing terminal transferase for the addition of the special nucleotides in accordance with this invention is widely applicable and the resulting modified nucleotides containing the special nucleotides in accordance with this invention including the special biotinated nucleotides or the special glycosylated nucleotides could be selectively recovered via complexing with avidin upon a Sepharose-avidin column or complexing with a lectin, such as Concanavalin A or a Sepharose-Concanavalin A column.

Illustrative of the practices of this invention, biotinated dUTP was added to the 3' ends of d[pT]$_4$ as well as single and double stranded DNA employing terminal transferase and the resulting product was purified through G-50 Sepharose and separated on a Sepharose-avidin affinity column. It was found that 69% of the d[pT]$_4$ molecules were biotinated and recovered on the Sepharose-avidin column. The results of this experiment established that terminal transferase added biotinated dUMP to the 3' ends of a polypyrimidine.

The detection of nucleic acids to which specific molecules have been covalently attached can be effected through the use of many naturally occurring proteins to which small molecules are known to specifically bind. In this procedure the small molecules are bound to the nucleotide using the allyl amine side chain. These nucleotides are then incorporated into specific nucleic acids using a DNA or RNA polymerase or ligase reaction or a chemical linkage. After annealing this probe with a complementary antiprobe sequence, the presence of the probe is assayed for by the specific binding of the protein to the ligand covalently bound to the probe.

Examples of protein-ligand reactions that are appropriate for this type of detector system include:

1. Enzymes and allosteric effector or modulator molecules. An example of this is the enzyme threonine dehydratase which is a heterotropic enzyme in that the effector molecule, L-isoleucine, is different than the substrate, L-threonine, J. Monod, J. Wyman and J. P. Changeux (1965), *J. Mol. Biol.* 12:88–118.

2. Effector molecules involved in regulation. An example of this is the specific binding of 3',5-cyclic adenosine monophosphate to the cyclic AMP receptor protein, I. Pastan and R. Perlman, *Science* 169:339–344 (1969). Another example is the lactose repressor molecule and the inducer molecules isopropylthiogalactoside or thiomethylgalactoside. These two inducer molecules are called gratuitous inducers in that they are not metabolized by the enzymes they induce, W. Gilbert and B. Muller-Hill, *Proc. Natl. Acad. Sci.* (US), 70:3581–3584, (1973).

3. Hormone receptors and other receptors on the surface of the cell to which organic molecules will specifically bind. An example of this is the epinephrine-epinephrine receptor system in which epinephrine is bound in a steriospecific manner with a high affinity to the receptor. With this system, since the receptor protein is insoluble in water, it will be imbedded in a lipid bilayer structure as for instance a liposome. Suitable detector systems would include specific enzymes or fluorescent molecules inside or within the lipid bilayer.

4. Specific ligand binding proteins included in the transport of small molecules. An example of this is the periplasmic binding proteins of bacteria which have been shown to bind many amino acids, glucose, galactose, ribose and other sugars, Pardee, A. *Science,* 162:632–637, (1968); G. L. Hazelbaur, and J. Adler, *Nature New Bio.* 230: 101–104, (1971).

In the above-mentioned examples the ligand bound to the nucleic acid reacts with a naturally occurring protein. The specificity of this reaction resides in the ligand-binding site of the protein.

One further example of small molecule interaction with naturally occurring proteins involves the specific binding of coenzyme or other prosthetic molecules to enzymes. Examples of such coenzymes include thiamin pyrophosphate, flavine mononucleotide, flavine adenine dinucleotide, nicotinamide adenine dinucleotide, nicotinamide adenine dinucleotide phosphate, coenzyme A, pyridoxyl phosphate, biotin, tetrahydrofolic acid, coenzyme B$_{12}$, lipoic and ascorbic acid. Many of these molecules form covalent linkages with their apoenzymes. However, some, for example, coenzyme A, coenzyme B$_{12}$ and tetrahydrofolic acid, associate in a non-covalent but specific manner with their cognate apoenzymes. A specific coenzyme-apoenzyme system for use in this system is flavine adenine dinucleotide (FAD) and flavine adenine dinucleotide reductase isolated from *Escherichia coli*. With this system the binding of FAD is sufficiently strong to permit detection.

The special nucleotides of this invention and polynucleotides including such nucleotides, either single-stranded or double-stranded polynucleotides, DNA and/or RNA, comprising the components, phosphoric acid moiety P (PM), the sugar or monosaccharide moiety S (SM), the base moiety B (BASE), a purine or a pyrimidine, and the signalling or self-detecting moiety, Sig, covalently attached to either the P, S or B moieties (PM, SM or BASE), as indicated hereinabove, have many uses and utilities. For example, the nucleotides of this invention and polynucleotides containing the nucleotides of this invention are useful as immune-stimulating agents, as adjuvants in vaccines, as agents for the stimulation or induction from competent cells, such as lymphocytes, for the production of lymphokines, cytokines or cytokinins, interferon or other cellular products.

It is well known that double-stranded poly A:U is a stimulator or inducer for the production of interferon, although weakly so. Similarly, poly I:C is also known as a stimulator or inducing agent for the production of interferon.

The advantage of polynucleotides, such as double-stranded polynucleotides incorporating one or more nucleotides in accordance with this invention is that, in effect, such polynucleotides would be more effective and more powerful inducing or stimulating agents for the production of interferon and related materials from cells. For example, nucleotides in accordance with this invention containing the above-described components P, S, B and Sig (PM, SM, BASE and Sig, respectively), are suitably prepared so that the nucleotides and polynucleotides prepared therefrom are more resistant to nucleases. Similarly, such nucleotides and polynucleotides containing the same and suitably prepared which are more capable of contacting, stimulating and penetrating cellular surfaces or membranes, such as the cellular surfaces or membranes of lymphocytes and other cells so as to stimulate the same for the production of a desired cellular product, such as interferon.

Particularly useful among those special nucleotides in accordance with this invention having the formula P-S-B-Sig PM-SM-BASE-Sig and especially useful are those wherein the Sig component is at the 5 position of the pyrimidine or the 7 position of the purine or a deazapurine or the N$^2$ position of guinine or the N$^6$ position of adenine. Such nucleotides and polynucleotides incorporating the same, both single-stranded and double-stranded nucleotides, DNA and/or RNA are prepared in accordance with this invention to provide increased stability with respect to the double-stranded helix of DNA or RNA or DNA-RNA hybrid containing the same. Increased resistance to nucleases is also achievable as well as alterations or favorable changes in the hydrophobic properties or electrical or charge properties of the nucleotides and polynucleotides containing the same. Also, nucleotides and polynucleotides in accordance with this invention are prepared which, when administered to humans, have reduced pyrogenicity or exhibit less other whole body toxic responses. Additionally, the nucleotides and polynucleotides are prepared in accordance with this invention to provide a ligand, such as the component Sig, to which specific polypeptides can combine to create or bring about the formation of RNA complexes. It is seen therefore that the nucleotides of this invention include the P, S, B and Sig components (PM, SM, BASE and Sig) wherein the Sig is covalently attached to either the P, S or B moieties (PM, SM and BASE, respectively) open up or provide a whole array of chemical agents having special biological effects including therapeutic effects and cytotoxic effects.

The special nucleotides of this invention, including polynucleotides containing these nucleotides, in addition to being stimulating or inducing agents for the production of cellular materials or products, such as interferons, lymphokines and/or cytokines, are also useful for their chemotherapeutic effect and for the preparation of chemotherapeutic agents based thereon but also for their cytotoxic effects and the production of cytotoxic agents based thereon. The moiety Sig attached to the special nucleotides of this invention containing the other moieties or components P, S, B (PM, SM, BASE) provides a site per se for the attachment thereto, the Sig component, of special agents of known chemotherapeutic or cytotoxic effect. Such nucleotides could be introduced or administered to the subject being treated, e.g. human body or animal, so as to be incorporated into the DNA and/or RNA components of the body or cell so as to either interfere with the synthesis of the body or cellular DNA and/or RNA or to attack tumors or to, in effect, kill or otherwise interfere with the growth of undesired cells.

The administration of the nucleotides and/or polynucleotides containing the nucleotides to the body, human body or animal, can be effected by a number of suitable means. Particularly effective would be the intravenous introduction to the body of preparations containing the nucleotides of this invention and a suitable physiologically acceptable carrier or the nucleotides could be administered subcutaneously, transdermally, or intramuscularly or by direct introduction into the site where the chemotherapeutic or cytotoxic effect of the nucleotides is sought or desired to be effective. Not only could desired chemotherapeutic or cytotoxic effects be achieved systemically or locally but also, as indicated hereinabove, the special P, S, B and Sig-containing (PM, SM, BASE and Sig, respectively) nucleotides of this invention, including polynucleotides containing such nucleotides, are useful as immune-stimulating agents and adjuvants therefor. Accordingly, vaccines containing the special nucleotides and polynucleotides in accordance with this invention can be prepared having improved effectiveness and versatility.

Of special interest in the practices of this invention improved polynucleotides incorporating the special nucleotides of this invention are provided as inducers or simulating agents for the production of interferon. Such polynucleotides would be single-stranded or double-stranded ribonucleotides, dsRNA, having the structures,

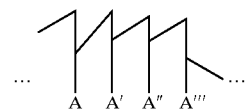

-continued

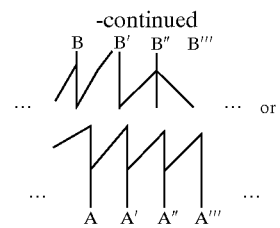

where A and B are complementary base pairs, such as a purine, a 7-deazapurine or pyrimidine modified by the addition of an organic moiety Sig in accordance with the disclosures of this invention on the 5 position of the pyrimidine ring or the 7 position of the purine ring or the $N^2$ of guanine, or the $N^6$ of adenine or the $N^4$ of cytosine as described herein. The modifications of the polynucleotides at these positions lead to relatively undisruptive or non-disruptive double-stranded nucleic acid molecules as measured by rates of association and melting points. In the special polynucleotides of this invention employed as inducers of interferon and other cellular or humoral factors or components, such as lymphokines or cytokines, the following groups would be attached thereto as indicated by the formulas,

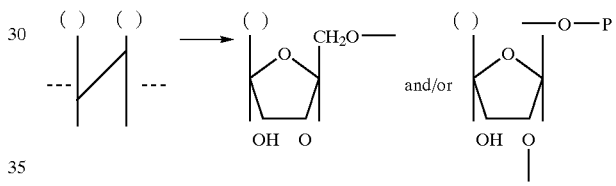

In the utilization of the special polynucleotides of this invention, such as the special dsRNA of this invention in the induction process for the production of interferon it has been demonstrated that DEAE-dextran facilitates this operation. It appears that since DEAE-dextran complexes with dsRNA and protects it for nuclease degradation, thereby enhancing interferon induction. It has also been noted that poly rC:rI is taken into cells more efficiently when complexed with DEAE-dextran. Accordingly in the practices of this invention the hydrophobic properties and the ionic or electron charge properties of the special dsRNA of this invention are important factors and capable of manipulation in the applicability of these materials to induce inteferon production. It has been observed that such conditions or factors which promote the induction of interferon also lead to and promote the induction of other cellular or humoral components, such as lymphokines and cytokines. It is apparent, therefore, that the special nucleotides of this invention act as immune modulators and stimulators of the immune response other than simply being effective as inducers of interferon production. Superior agents for the above in accordance with the practices of this invention would include nucleotides wherein the Sig moiety incorporates biotin or streptavidin or avidin.

Poly rI:poly rC complexed poly L-lysine exhibits adjuvant properties and such properties are enhanced and improved in accordance with the practices of this invention when the poly rI and poly rC components are modified to include one or more of the special nucleotides in accordance with this invention.

The preparation of DNA probes in accordance with another aspect of this invention can be carried out in a manner which does not require the preparation or utilization of the special nucleotides described herein. For example, double-stranded DNA can be reacted with a carcinogen or alkylating agent. After the carcinogen has reacted with or alkylated the double-stranded DNA, the resulting modified DNA is melted to produce a DNA hybridizing probe containing the reaction product of the DNA and the carcinogen or alkylating agent. When thus-modified or reacted DNA is employed as a hybridizing probe, any resulting formed double helix or double-stranded DNA would be assayed or searched out by means of a double antibody technique. The primary antibody would be an anti-carcinogen and the secondary antibody would be horseradish-peroxidase conjugated anti-peroxidase antibody. The advantage of this technique is that it would be easy to label the double-stranded DNA. This special approach is indicated hereinabove in the examples accompanying the description of this invention and is generally applicable for the preparation of DNA probes from double-stranded or double helical DNA. However, this procedure is a disruptive procedure involving the modification of the double helical deoxyribonucleotide polymer or DNA.

In the description of the special nucleotides and modified DNA employed or developed in the practices of this invention, mention has been made of mono, oligo and polysaccharides. It is pointed out that derivatives of mono, oligo and polysaccharides are also useful in the preparation of the special nucleotides of this invention. For example, it is possible to modify individual sugar moieties employed in the make-up of the special nucleotides and employ the resulting modified sugar moieties to effect or carry out additional chemical reactions. Such modified mono, oligo and polysaccharide moieties, when employed as the Sig moiety in the preparation of the special nucleotides of this invention, provide an added versatility with respect to the detection of the nucleotides or other compounds containing such modified saccharides either as the sugar S (SM) or as the Sig moiety thereof.

In another aspect of this invention the Sig moiety instead of being attached to a nucleotide could also be attached to proteins. Not only could such proteins be attached to nucleotides or polynucleotides but also such proteins could be identified per se whether attached to a nucleotide or polynucleotide or unattached. In accordance with the practices of this aspect of the invention, a suitable such protein adduct would have the formula,

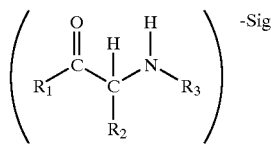

wherein $R_1$ is an OH or an amino acid or acids and $R_2$ is an amino acid side chain and $R_3$ is H or an amino acid or acids and Sig is attached to the $R_1$ and/or $R_2$ and/or $R_3$.

The invention claimed is:

1. An oligo- or polynucleotide which is complementary to a nucleic acid of interest or a portion thereof, said oligo- or polynucleotide comprising at least one modified nucleotide or modified nucleotide analog having the formula Sig-PM-SM-BASE wherein PM is a phosphate moiety, SM is a furanosyl moiety and BASE is a base moiety comprising a pyrimidine, a pyrimidine analog, a purine, a purine analog, a deazapurine or a deazapurine analog wherein said analog can be attached to or coupled to or incorporated into DNA or RNA wherein said analog does not substantially interfere with double helix formation or nucleic acid hybridization, said PM being attached to SM, said BASE being attached to SM, and said Sig being covalently attached to PM directly or through a non-nucleotidyl chemical linkage, and wherein said Sig comprises a non-polypeptide, non-nucleotidyl, non-radioactive label moiety which can be directly or indirectly detected when attached to PM or when said modified nucleotide is incorporated into said oligo- or polynucleotide or when said oligo- or polynucleotide is hybridized to said complementary nucleic acid of interest or a portion thereof, and wherein Sig comprises biotin, iminobiotin, an electron dense component, a magnetic component, a metal-containing component, a fluorescent component, a chemiluminescent component, a chromogenic component, a hapten or a combination of any of the foregoing.

2. The oligo- or polynucleotide of claim 1, wherein Sig comprises at least three carbon atoms.

3. The oligo- or polynucleotide of claim 1, wherein said magnetic component comprises magnetic oxide.

4. The oligo- or polynucleotide of claim 3, wherein said magnetic oxide comprises ferric oxide.

5. The oligo- or polynucleotide of claim 1, wherein said metal-containing component is catalytic.

6. The oligo- or polynucleotide of claim 1, wherein said fluorescent component comprises fluorescein, rhodamine or dansyl.

7. The oligo- or polynucleotide of claim 1, wherein said covalent attachment comprises

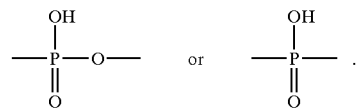

8. The oligo- or polynucleotide of claim 1, wherein said chemical linkage does not interfere substantially with the characteristic ability of Sig to form a detectable signal.

9. The oligo- or polynucleotide of claim 1, wherein said chemical linkage comprises a —CH$_2$NH— moiety.

10. The oligo- or polynucleotide of claim 1, wherein said chemical linkage comprises an allylamine group.

11. The oligo- or polynucleotide of claim 1, wherein said chemical linkage comprises any of the moieties:

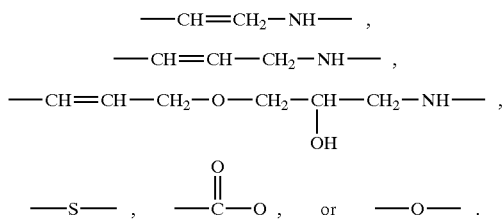

12. The oligo- or polynucleotide of claim 1, wherein said PM comprises a monophosphate, a diphosphate or a triphosphate.

13. The oligo- or polynucleotide of claim 1, wherein said Sig moiety is covalently attached to said PM through a phosphorous atom or phosphate oxygen.

14. The oligo- or polynucleotide of claim 1, wherein said Sig moiety is attached to the PM of a terminal nucleotide in said oligo- or polydeoxyribonucleotide.

15. The oligo- or polynucleotide of claim 14, wherein the furanosyl moiety of said terminal nucleotide comprises a hydrogen atom at the 2' position thereof.

16. The oligo- or polynucleotide of claim 14, wherein the furanosyl moiety of said terminal nucleotide comprises an oxygen atom at the 2' position thereof.

17. The oligo- or polynucleotide of claim 15, wherein the furanosyl moiety of said terminal nucleotide comprises a hydrogen atom at the 3' position thereof.

18. The oligo- or polynucleotide of claim 16, wherein the furanosyl moiety of said terminal nucleotide comprises an oxygen atom at the 3' position thereof.

19. The oligo- or polynucleotide of claim 1, wherein said furanosyl moiety comprises a ribose, a deoxyribose or a dideoxyribose.

20. The oligo- or polynucleotide of claim 1, wherein said pyrimidine analogs comprise thymidine analogs, uridine analogs, deoxyuridine analogs, cytidine analogs, deoxycytidine analogs or a combination of any of the foregoing.

21. The oligo- or polynucleotide of claim 20, wherein said uridine analogs comprise 5-bromo-2'-deoxyuridine-5'-phosphate.

22. The oligo- or polynucleotide of claim 20, wherein said deoxycytidine analogs comprise 5-hydroxymethyl-2'-deoxycytidylic acid.

23. The oligo- or polynucleotide of claim 1, wherein said purine analogs comprise adenosine analogs, deoxyadenosine analogs, guanosine analogs, deoxyguanosine analogs or a combination of any of the foregoing.

24. The oligo- or polynucleotide of claim 23, wherein said adenosine analogs comprise tubericidin and toyocamycin.

25. The oligo- or polynucleotide of claim 1, wherein said oligo- or polynucleotide comprises an oligo- or polydeoxyribonucleotide.

26. The oligo- or polynucleotide of claim 1, wherein said oligo- or polynucleotide comprises an oligo- or polydeoxyribonucleotide and further comprises at least one ribonucleotide.

27. The oligo- or polynucleotide of claim 1, wherein said oligo- or polynucleotide comprises an oligo- or polyribonucleotide.

28. The oligo- or polynucleotide of claim 1, wherein said oligo- or polynucleotide comprises an oligo- or polyribonucleotide and further comprises at least one deoxyribonucleotide.

29. An oligo- or polynucleotide which is complementary to a nucleic acid of interest or a portion thereof, said oligo- or polynucleotide comprising at least one modified nucleotide or a modified nucleotide analog having the structural formula:

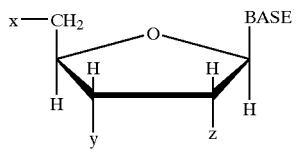

wherein BASE is a moiety comprising a pyrimidine, a pyrimidine analog, a purine, a purine analog, a deazapurine or a deazapurine analog, wherein said analog can be attached to or coupled to or incorporated into DNA or RNA, wherein said analog does not substantially interfere with double helix formation or nucleic acid hybridization, and wherein said BASE is attached to the 1' position of the furanosyl ring from the N1 position when said BASE is a pyrimidine or a pyrimidine analog, or from the N9 position when said BASE is a purine, a purine analog, a deazapurine or a deazapurine analog;

wherein x comprises H—, HO—, a mono-phosphate, a di-phosphate or a tri-phosphate;

wherein y comprises H—, HO—, a mono-phosphate, a di-phosphate or a tri-phosphate;

wherein z comprises H—, HO—, a mono-phosphate, a di-phosphate or a tri-phosphate; and wherein Sig is covalently attached directly or through a non-nucleotidyl chemical linkage to at least one phosphate comprising x, y, z, or a combination thereof, and wherein said Sig comprises a non-polypeptide, non-nucleotidyl, non-radioactive label moiety which can be directly or indirectly detected when attached to said phosphate or when said modified nucleotide is incorporated into said oligo- or polynucleotide or when said oligo- or polynucleotide is hybridized to said complementary nucleic acid of interest or a portion thereof, wherein Sig comprises biotin, iminobiotin, an electron dense component, a magnetic component, a metal-containing component, a fluorescent component, a chemiluminescent component, a chromogenic component, a hapten, or a combination of any of the foregoing.

30. The oligo- or polynucleotide of claim 29, wherein Sig comprises at least three carbon atoms.

31. The oligo- or polynucleotide of claim 29, wherein said magnetic component comprises magnetic oxide.

32. The oligo- or polynucleotide of claim 31, wherein said magnetic oxide comprises ferric oxide.

33. The oligo- or polynucleotide of claim 29, wherein said metal-containing component is catalytic.

34. The oligo- or polynucleotide of claim 29, wherein said fluorescent component comprises fluorescein, rhodamine or dansyl.

35. The oligo- or polynucleotide of claim 29, wherein said covalent attachment comprises

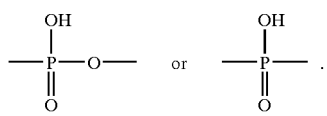

36. The oligo- or polynucleotide of claim 29, wherein said chemical linkage does not interfere substantially with the characteristic ability of Sig to form a detectable signal.

37. The oligo- or polynucleotide of claim 29, wherein said chemical linkage comprises a —CH₂NH— moiety.

38. The oligo- or polynucleotide of claim 29, wherein said chemical linkage comprises an allylamine group.

39. The oligo- or polynucleotide of claim 29, wherein said chemical linkage comprises any of the moieties:

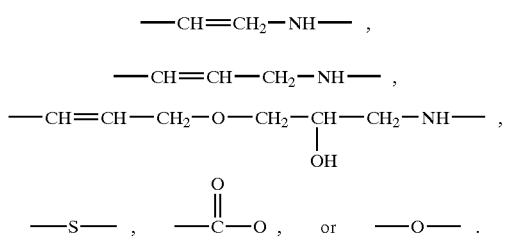

40. The oligo- or polynucleotide of claim 29, wherein said x comprises a monophosphate, a diphosphate or a triphosphate and y comprises a monophosphate.

41. The oligo- or polynucleotide of claim 29, wherein said Sig moiety is covalently attached to said phosphate through a phosphorus atom or phosphate oxygen.

42. The oligo- or polynucleotide of claim 29, wherein said x comprises a monophosphate.

43. The oligo- or polynucleotide of claim 29, wherein said Sig moiety is attached to the phosphate moiety of a terminal nucleotide in said oligo- or polynucleotide.

44. The oligo- or polynucleotide of claim 43, wherein z of said furanosyl moiety of said terminal nucleotide comprises a hydrogen atom.

45. The oligo- or polynucleotide of claim 43, wherein z of said furanosyl moiety of said terminal nucleotide comprises an oxygen atom.

46. The oligo- or polynucleotide of claim 44, wherein y of said furanosyl moiety comprises a hydrogen atom.

47. The oligo- or polynucleotide of claim 45, wherein y of said furanosyl moiety comprises an oxygen atom.

48. The oligo- or polynucleotide of claim 29, wherein said furanosyl moiety comprises a ribose, a deoxyribose or a dideoxyribose.

49. The oligo- or polynucleotide of claim 29, wherein said pyrimidine analogs comprise thymidine analogs, uridine analogs, deoxyuridine analogs, cytidine analogs, deoxycytidine analogs or a combination of any of the foregoing.

50. The oligo- or polynucleotide of claim 49, wherein said uridine analogs comprise 5-bromo-2'-deoxyuridine-5'-phosphate.

51. The oligo- or polynucleotide of claim 49, wherein said deoxycytidine analogs comprise 5-hydroxymethyl-2'-deoxycytidylic acid.

52. The oligo- or polynucleotide of claim 29, wherein said purine analogs comprise adenosine analogs, deoxyadenosine analogs, guanosine analogs, deoxyguanosine analogs, or a combination of any of the foregoing.

53. The oligo- or polynucleotide of claim 52, wherein said adenosine analogs comprise tubericidin or toyocamycin.

54. The oligo- or polynucleotide of claim 29, wherein said oligo- or polynucleotide comprises an oligo- or polydeoxyribonucleotide.

55. The oligo- or polynucleotide of claim 29, wherein said oligo- or polynucleotide comprises an oligo- or polydeoxyribonucleotide and further comprises at least one ribonucleotide.

56. The oligo- or polynucleotide of claim 29, wherein said oligo- or polynucleotide comprises an oligo- or polyribonucleotide.

57. The oligo- or polynucleotide of claim 29, wherein said oligo- or polynucleotide comprises an oligo- or polyribonucleotide and further comprises at least one deoxyribonucleotide.

58. The oligo- or polynucleotide of claim 29, having the structural formula:

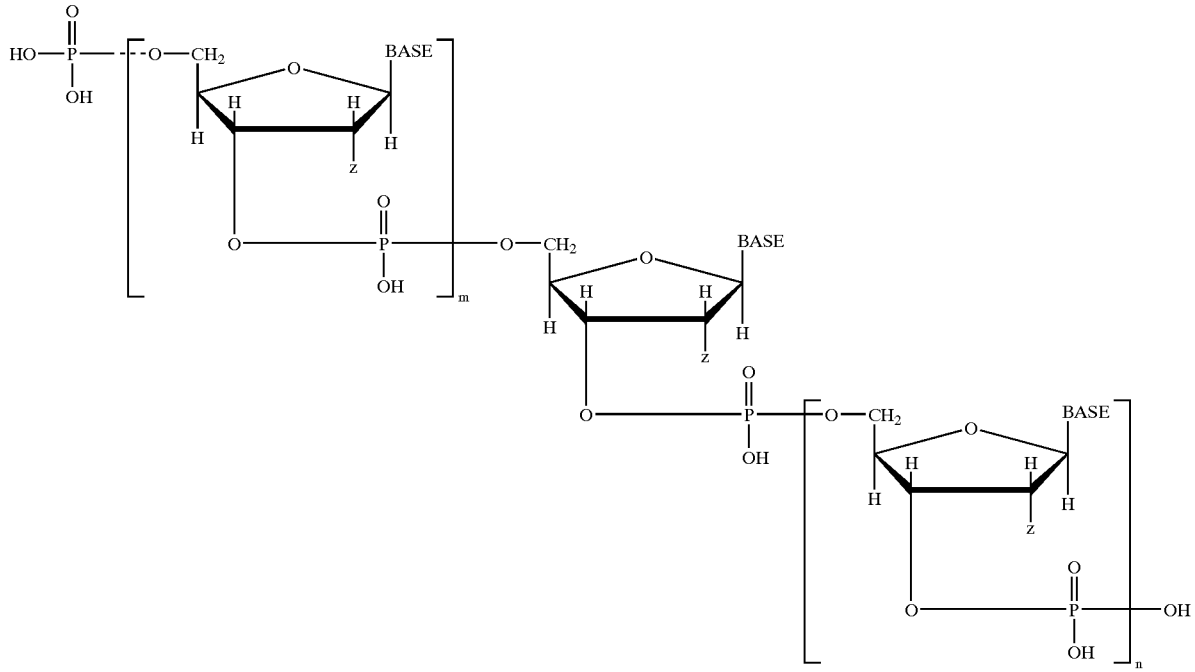

wherein m and n represent integers from 0 up to about 100,000, and wherein said Sig moiety is attached to at least one of the phosphate moieties in said structural formula.

59. An oligo- or polynucleotide which is complementary to a nucleic acid of interest or a portion thereof, said oligo- or polynucleotide comprising at least one modified nucleotide or a modified nucleotide analog having the formula Sig-PM-SM-BASE wherein PM is a phosphate moiety, SM is a furanosyl moiety and BASE is a base moiety comprising a pyrimidine, a pyrimidine analog, a purine, a purine analog, a deazapurine or a deazapurine analog, wherein said analog can be attached to or coupled to or incorporated into DNA or RNA, wherein said analog does not substantially interfere with double helix formation or nucleic acid hybridization, said PM is attached to SM, said BASE is attached to SM, said Sig is covalently attached to PM directly or via a non-nucleotidyl chemical linkage, and wherein said Sig comprises a non-polypeptide, non-nucleotidyl, non-radioactive label moiety which can be directly or indirectly detected when attached to PM or when said modified nucleotide is incorporated into said oligo- or polynucleotide, or when said oligo- or polynucleotide is hybridized to said complementary nucleic acid of interest or a portion thereof, provided that when said oligo- or polynucleotide is an oligoribonucleotide or a polyribonucleotide, and when Sig is attached through a chemical linkage to a terminal PM at the 3' position of a terminal ribonucleotide, said chemical linkage is not obtained through a 2',3' vicinal oxidation of a 3' terminal ribonucleotide previously attached to said oligoribonucleotide or polyribonucleotide, and wherein said Sig comprises biotin, iminobiotin, an electron dense component, a magnetic component, a metal-containing component, a fluorescent component, a chemiluminescent component, a chromogenic component, a hapten, or a combination of any of the foregoing.

60. The oligo- or polynucleotide of claim 59, wherein Sig comprises at least three carbon atoms.

61. The oligo- or polynucleotide of claim 59, wherein said magnetic component comprises magnetic oxide.

62. The oligo- or polynucleotide of claim 61, wherein said magnetic oxide comprises ferric oxide.

63. The oligo- or polynucleotide of claim 59, wherein said metal-containing component is catalytic.

64. The oligo- or polynucleotide of claim 59, wherein said fluorescent component comprises fluorescein, rhodamine or dansyl.

65. The oligo- or polynucleotide of claim 59, wherein said covalent attachment comprises

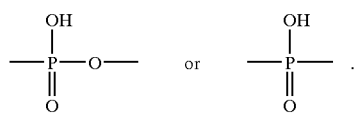

66. The oligo- or polynucleotide of claim 59, wherein said chemical linkage does not interfere substantially with the characteristic ability of Sig to form a detectable signal.

67. The oligo- or polynucleotide of claim 59, wherein said chemical linkage comprises a —CH₂NH— moiety.

68. The oligo- or polynucleotide of claim 59, wherein said chemical linkage comprises an allylamine group.

69. The oligo- or polynucleotide of claim 59, wherein said chemical linkage comprises any of the moieties:

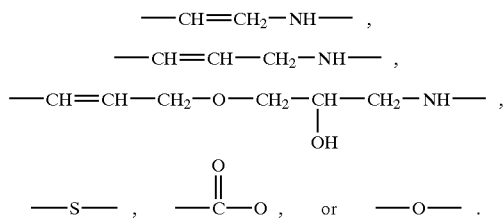

70. The oligo- or polynucleotide of claim 59, wherein said PM comprises a monophosphate, a diphosphate or a triphosphate.

71. The oligo- or polynucleotide of claim 59, wherein said Sig moiety is covalently attached to said PM through a phosphorus atom or phosphate oxygen.

72. The oligo- or polynucleotide of claim 59, wherein said Sig moiety is attached to the PM of a terminal nucleotide in said oligo- or polynucleotide.

73. The oligo- or polynucleotide of claim 72, wherein the furanosyl moiety of said terminal nucleotide has a hydrogen atom at the 2' position thereof.

74. The oligo- or polynucleotide of claim 72, wherein the furanosyl moiety of said terminal nucleotide has an oxygen atom at the 2' position thereof.

75. The oligo- or polynucleotide of claim 73, wherein the furanosyl moiety of said terminal nucleotide has a hydrogen atom at the 3' position thereof.

76. The oligo- or polynucleotide of claim 74, wherein the furanosyl moiety of said terminal nucleotide has an oxygen atom at the 3' position thereof.

77. The oligo- or polynucleotide of claim 59, wherein said furanosyl moiety comprises a ribose, a deoxyribose or a dideoxyribose.

78. The oligo- or polynucleotide of claim 59, wherein said pyrimidine analogs comprise thymidine analogs, uridine analogs, deoxyuridine analogs, cytidine analogs, deoxycytidine analogs or a combination of any of the foregoing.

79. The oligo- or polynucleotide of claim 78, wherein said uridine analogs comprise 5-bromo-2'-deoxyuridine-5'-phosphate.

80. The oligo- or polynucleotide of claim 78, wherein said deoxycytidine analogs comprise 5-hydroxymethyl-2'-deoxycytidylic acid.

81. The oligo- or polynucleotide of claim 59, wherein said purine analogs comprise adenosine analogs, deoxyadenosine analogs, guanosine analogs, deoxyguanosine analogs or a combination of any of the foregoing.

82. The oligo- or polynucleotide of claim 81, wherein said adenosine analogs comprise tubericidin and toyocamycin.

83. The oligo- or polynucleotide of claim 59, wherein said oligo- or polynucleotide comprises an oligo- or polydeoxyribonucleotide.

84. The oligo- or polynucleotide of claim 59, wherein said oligo- or polynucleotide comprises an oligo- or polydeoxyribonucleotide and further comprises at least one ribonucleotide.

85. The oligo- or polynucleotide of claim 59, wherein said oligo- or polynucleotide comprises an oligo- or polyribonucleotide.

86. The oligo- or polynucleotide of claim 59, wherein said oligo- or polynucleotide comprises an oligo- or polyribonucleotide and further comprises at least one deoxyribonucleotide.

87. An oligo- or polynucleotide which is complementary to a nucleic acid of interest or a portion thereof, said oligo- or polynucleotide comprising at least one modified nucleotide or a modified nucleotide analog having the structural formula:

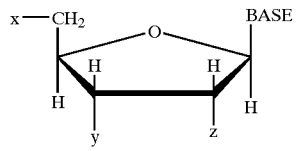

wherein BASE is a moiety comprising a pyrimidine, a pyrimidine analog, a purine, a purine analog, a deazapurine, a deazapurine analog, wherein said analog can be attached to or coupled to or incorporated into DNA or RNA wherein said analog does not substantially interfere with double helix formation or nucleic acid hybridization, and wherein BASE is attached to the 1' position of the furanosyl ring from the N1 position when BASE is a pyrimidine or a pyrimidine analog, from the N9 position of the furanosyl ring when BASE is a purine, a purine analog, a deazapurine or a deazapurine;

wherein x comprises H—, HO—, a mono-phosphate, a di-phosphate or a tri-phosphate;

wherein y comprises H—, HO—, a mono-phosphate, a di-phosphate or a tri-phosphate;

wherein z comprises H—, HO—, a mono-phosphate, a di-phosphate or a tri-phosphate; and wherein said Sig is covalently attached directly or through a non-nucleotidyl chemical linkage to at least one phosphate comprising of x, y and z, or a combination thereof, and wherein said Sig comprises a non-polypeptide, non-nucleotidyl, non-radioactive label moiety which can be directly or indirectly detected when so attached to said phosphate or when said modified nucleotide is incorporated into said oligo- or polynucleotide, or when said oligo- or polynucleotide is hybridized to said complementary nucleic acid of interest or a portion thereof, provided that when said oligo- or polynucleotide is an oligoribonucleotide or a polyribonucleotide and when Sig is attached through a chemical linkage to a terminal PM at the 3' position of a terminal ribonucleotide, said chemical linkage is not obtained through a 2',3' vicinal oxidation of a 3' terminal ribonucleotide previously attached to said oligoribonucleotide or polyribonucleotide, and wherein Sig comprises biotin, iminobiotin, an electron dense component, a magnetic component, a metal-containing component, a fluorescent component, a chemiluminescent component, a chromogenic component, a hapten, or a combination of any of the foregoing.

88. The oligo- or polynucleotide of claim 87, wherein Sig comprises at least three carbon atoms.

89. The oligo- or polynucleotide of claim 87, wherein said magnetic component comprises magnetic oxide.

90. The oligo- or polynucleotide of claim 89, wherein said magnetic oxide comprises ferric oxide.

91. The oligo- or polynucleotide of claim 87, wherein said metal-containing component is catalytic.

92. The oligo- or polynucleotide of claim 87, wherein said fluorescent component comprises fluorescein, rhodamine or dansyl.

93. The oligo- or polynucleotide of claim 87, wherein said covalent attachment comprises $$-\overset{\overset{\displaystyle OH}{|}}{\underset{\underset{\displaystyle O}{\|}}{P}}-O- \quad \text{or} \quad -\overset{\overset{\displaystyle OH}{|}}{\underset{\underset{\displaystyle O}{\|}}{P}}-.$$

94. The oligo- or polynucleotide of claim 87, wherein said chemical linkage does not interfere substantially with the characteristic ability of Sig to form a detectable signal.

95. The oligo- or polynucleotide of claim 87, wherein said chemical linkage comprises a —CH$_2$NH— moiety.

96. The oligo- or polynucleotide of claim 87, wherein said chemical linkage comprises an allylamine group.

97. The oligo- or polynucleotide of claim 87, wherein said chemical linkage comprises any of the moieties:

—CH=CH$_2$—NH— ,

—CH=CH—CH$_2$—NH— ,

—CH=CH—CH$_2$—O—CH$_2$—CH(OH)—CH$_2$—NH— ,

—S— , —C(=O)—O , or —O— .

98. The oligo- or polynucleotide of claim 87, wherein said x comprises a monophosphate, a diphosphate or a triphosphate and y comprises a monophosphate.

99. The oligo- or polynucleotide of claim 87, wherein said Sig moiety is covalently attached to said phosphate through a phosphorus atom or phosphate oxygen.

100. The oligo- or polynucleotide of claim 87, wherein said x comprises a monophosphate.

101. The oligo- or polynucleotide of claim 87, wherein said Sig moiety is attached to the phosphate moiety of a terminal nucleotide in said oligo- or polynucleotide.

102. The oligo- or polynucleotide of claim 101, wherein z of said furanosyl moiety of said terminal nucleotide comprises a hydrogen atom.

103. The oligo- or polynucleotide of claim 101, wherein z of said furanosyl moiety of said terminal nucleotide comprises an oxygen atom.

104. The oligo- or polynucleotide of claim 102, wherein y of said furanosyl moiety comprises a hydrogen atom.

105. The oligo- or polynucleotide of claim 103, wherein y of said furanosyl moiety comprises an oxygen atom.

106. The oligo- or polynucleotide of claim 87, wherein said furanosyl moiety comprises a ribose, a deoxyribose or a dideoxyribose.

107. The oligo- or polynucleotide of claim 87, wherein said pyrimidine analogs comprise thymidine analogs, uridine analogs, deoxyuridine analogs, cytidine analogs, deoxycytidine analogs or a combination of any of the foregoing.

108. The oligo- or polynucleotide of claim 107, wherein said uridine analogs comprise 5-bromo-2'-deoxyuridine-5'-phosphate.

109. The oligo- or polynucleotide of claim 107, wherein said deoxycytidine analogs comprise 5-hydroxymethyl-2'-deoxycytidylic acid.

110. The oligo- or polynucleotide of claim 87, wherein said purine analogs comprise adenosine analogs, deoxyadenosine analogs, guanosine analogs, deoxyguanosine analogs, or a combination of any of the foregoing.

111. The oligo- or polynucleotide of claim 110, wherein said adenosine analogs comprise tubericidin or toyocamycin.

112. The oligo- or polynucleotide of claim 87, wherein said oligo- or polynucleotide comprises an oligo- or polydeoxyribonucleotide.

113. The oligo- or polynucleotide of claim 112, wherein said oligo- or polynucleotide comprises an oligo- or polydeoxyribonucleotide and further comprises at least one ribonucleotide.

114. The oligo- or polynucleotide of claim 87, wherein said oligo- or polynucleotide comprises an oligo- or polyribonucleotide.

115. The oligo- or polynucleotide of claim 87, wherein said oligo- or polynucleotide comprises an oligo- or polyribonucleotide and further comprises at least one deoxyribonucleotide.

116. The oligo- or polynucleotide of claim 87, having the structural formula:

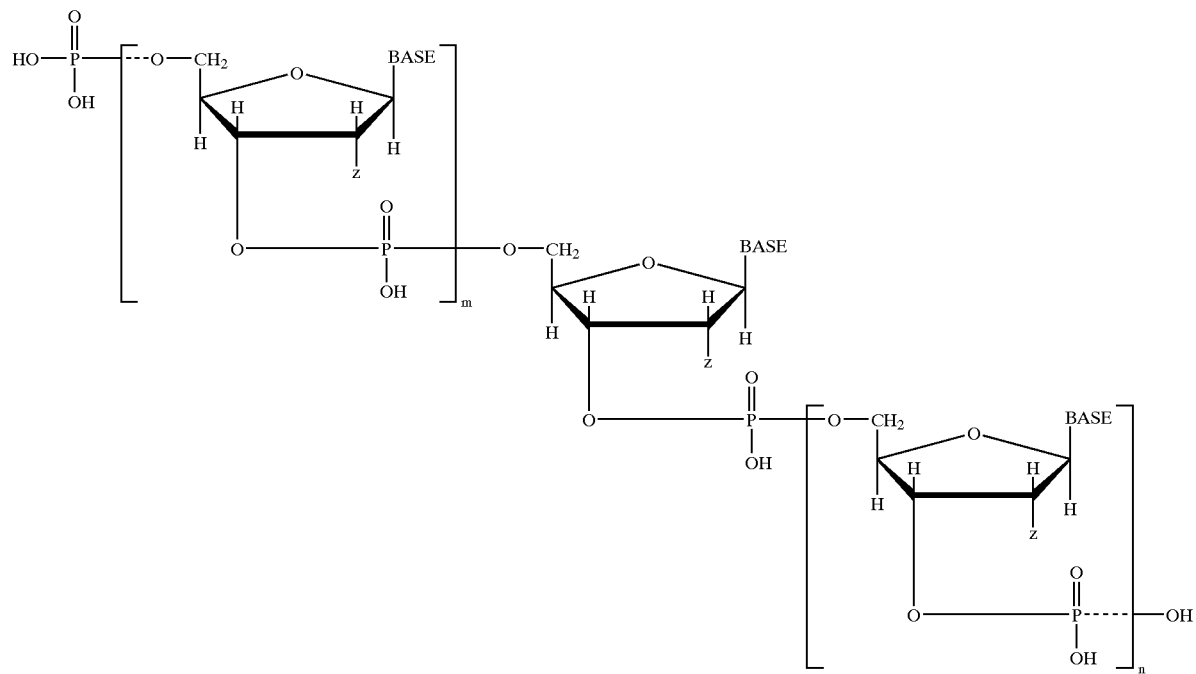
wherein m and n represent integers from 0 up to about 100,000, and wherein said Sig moiety is attached to at least one of the phosphate moieties in said structural formula.
* * * * *